US012760095B2

(12) United States Patent
Qian et al.

(10) Patent No.: US 12,760,095 B2
(45) Date of Patent: Oct. 13, 2026

(54) ANTI-CLDN18.2 ANTIBODIES AND DIAGNOSTIC USES THEREOF

(71) Applicant: SUZHOU TRANSCENTA THERAPEUTICS CO., LTD., Suzhou (CN)

(72) Inventors: Xueming Qian, Suzhou (CN); Xinlai Yao, Suzhou (CN); Huanhuan Guo, Suzhou (CN); Hongjun Li, Suzhou (CN); Yi Gu, Suzhou (CN)

(73) Assignee: SUZHOU TRANSCENTA THERAPEUTICS CO., LTD., Suzhou (CN)

( * ) Notice: Subject to any disclaimer, the term of this patent is extended or adjusted under 35 U.S.C. 154(b) by 906 days.

(21) Appl. No.: 17/927,740

(22) PCT Filed: May 24, 2021

(86) PCT No.: PCT/CN2021/095411

§ 371 (c)(1),
(2) Date: Nov. 25, 2022

(87) PCT Pub. No.: WO2021/238831

PCT Pub. Date: Dec. 2, 2021

(65) Prior Publication Data

US 2023/0331836 A1 Oct. 19, 2023

(51) Int. Cl.

*C07K 16/28* (2006.01)
*A61P 35/00* (2006.01)
*C12N 15/63* (2006.01)
*G01N 33/575* (2026.01)

(52) U.S. Cl.

CPC .............. *C07K 16/28* (2013.01); *A61P 35/00* (2018.01); *C12N 15/63* (2013.01); *G01N 33/57557* (2026.01); *C07K 2317/31* (2013.01); *C07K 2317/565* (2013.01); *C07K 2317/92* (2013.01)

(58) Field of Classification Search

CPC .............. C07K 16/28; C07K 2317/565; C07K 2317/52; C07K 16/30; C07K 2317/33; A61K 2039/505

See application file for complete search history.

(56) References Cited

U.S. PATENT DOCUMENTS

| | | | | |
|---|---|---|---|---|
| 2007/0071675 | A1 | 3/2007 | Wu et al. | |
| 2012/0164160 | A1 | 6/2012 | Sahin et al. | |
| 2018/0117174 | A1* | 5/2018 | Sahin | A61K 47/6863 |
| 2018/0282389 | A1 | 10/2018 | Sahin et al. | |
| 2020/0031898 | A1 | 1/2020 | Sahin et al. | |

FOREIGN PATENT DOCUMENTS

| | | | |
|---|---|---|---|
| CN | 1714150 | A | 12/2005 |
| CN | 104321345 | A | 1/2015 |
| CN | 109762067 | A | 5/2019 |
| CN | 110862454 | A | 3/2020 |
| EP | 3283521 | A1 | 2/2018 |
| RU | 2678127 | C2 | 1/2019 |
| WO | 01/77342 | A1 | 10/2001 |
| WO | 2004047863 | A2 | 6/2004 |
| WO | 2013167259 | A1 | 11/2013 |
| WO | 2014146672 | A1 | 9/2014 |
| WO | 2016165762 | A1 | 10/2016 |
| WO | 2016166122 | A1 | 10/2016 |
| WO | 2019173420 | A1 | 9/2019 |
| WO | 2019174617 | A1 | 9/2019 |
| WO | 2019219089 | A1 | 11/2019 |
| WO | 2020082209 | A1 | 4/2020 |

OTHER PUBLICATIONS

The Search Report for the counterpart Chinese patent application 202180041601.5, mailed on Aug. 22, 2025.

Liang'e Xu et al. Advances of CLDN18.2 protein in the therapy of malignant tumors, Chin J Clin Oncol 2019. vol. 46. No. 6, doi:10.3969/j.issn.1000-8179.2019.06.223.

Office Action of the Russian Application No. 2022129468, issued on Nov. 29, 2024 and English Translation thereof.

Roitt I. et al., "Immunology", Moscow, "Mir", 2000, pp. 110-111.

Pakula A.A. et al. Genetic analysis of protein stability and function, Anna. Rev. Genet, 1989, vol. 23, pp. 289-310.

Chen C. et.al., Enhancement and destruction of antibody function by somatic mutation: unequal occurrence is controlled by V gene combinatorial associations, The EMBO J., v. 14, n. 12, 1995, pp. 2784-2794.

P. B. Dirks, Brain Tumor Stem Cells: Bringing Order to the Chaos of Brain Cancer. Journal of Clinical Oncology, 2008, 26(17), 2916-2924. DOI:10.1200/jco.2008.17.6792.

López-Lázaro, M. The migration ability of stem cells can explain the existence of cancer of unknown primary site. Rethinking metastasis. Oncoscience, 2015, 2, 467. doi:10.18632/oncoscience.159.

B. Tran and M.A. Rosenthal, Survival comparison between glioblastoma multiforme and other incurable cancers, Journal of Clinical Neuroscience, 2010, vol. 17, Is. 4, p. 417-421.

(Continued)

*Primary Examiner* — Laura B Goddard

*Assistant Examiner* — Alyssa Rae Stonebraker

(74) *Attorney, Agent, or Firm* — Junhe Law Office P.C.; James J. Zhu

(57) ABSTRACT

The present disclosure provides herein novel monoclonal anti-CLDN18.2 antibodies or antigen-binding fragments thereof which specifically recognize CLDN18.2 without cross-reacting with CLDN18.1. The present disclosure further provides isolated polynucleotides encoding such anti-CLDN18.2 antibodies or antigen-binding fragments thereof, vectors comprising such isolated polynucleotides, host cells comprising such vectors, pharmaceutical compositions and kits comprising such anti-CLDN18.2 antibodies or antigen-binding fragments thereof, and the diagnostic uses thereof.

21 Claims, 12 Drawing Sheets

Specification includes a Sequence Listing.

(56) References Cited

OTHER PUBLICATIONS

Derksen P. W. B. et al. Illegitimate WNT signaling promotes proliferation of multiple myeloma cells //Proceedings of the National Academy of Sciences.—2004, 101(16), p. 6122-6127, see p. 6122.
Rudikoff S et al: "Single amino acid substitution altering antigen-binding specificity", Proceedings of the National Academy of Sciences, National Academy of Sciences, vol. 79, No. 6, Mar. 1, 1982 (Mar. 1, 1982), pp. 1979-1983, XP002986051, ISSN: 0027-8424, DOI: 10.1073/PNAS.79.6.197.
Extended European Search Report of the European Application No. 21812540.9, issued on Jun. 7, 2024.
International Search Report of PCT/CN2021/095411, mailed on Aug. 23, 2021.
First Office Action of the Taiwanese Application No. 110118625, issued on Jul. 29, 2024.
Shen, J., Vil, M. D., Jimenez, X., lacolina, M., Zhang, H., & Zhu, Z. (2006). Single variable domain-IgG fusion. A novel recombinant approach to Fc domain-containing bispecific antibodies. The Journal of biological chemistry, 281(16), 10706-10714. https://doi.org/10.1074/jbc.M513415200.
Torres, M., & Casadevall, A. (2008). The immunoglobulin constant region contributes to affinity and specificity. Trends in immunology, 29(2), 91-97. https://doi.org/10.1016/j.it.2007.11.004.
The Second Office Action for the counterpart Russian patent application, mailed on Apr. 24, 2025.

* cited by examiner

| Ab. | GC182 | 69H2F7E6 | 14G11G2D2 |
|---|---|---|---|
| EC50 (ng/mL) | / | 14.34 | 26.95 |

| Ab. | GC182 | 69H2F7E6 | 14G11G2D2 |
|---|---|---|---|
| EC50 (ng/mL) | / | 13.87 | 12.75 |

| Ab. | GC182 | 69H2F7E6 | 14G11G2D2 |
|---|---|---|---|
| EC50 (ng/mL) | / | / | / |

| Sample ID | KD (M) | kon(1/Ms) | koff(1/s) |
|---|---|---|---|
| 69H2F7E6 | 1.48E-09 | 4.71E+05 | 6.95E-04 |
| 14G11G2D2 | 2.13E-10 | 5.22E+05 | 1.11E-04 |
| GC182 | / | / | / |

14G11G2D2

69H2F7E6 GC182

| SED ID NO. | Sequences |
|---|---|
| 1 | RNYFH |
| 2 | RSSQNIVHSNGNTYLE |
| 3 | WIYPGGFDIEYSEKFKG |
| 4 | KVSNRFS |
| 5 | NYGSTFGY |
| 6 | FQGSHVPFT |
| 7 | TYYIH |
| 8 | $X_1X_2YX_3H$ |
| 9 | WIYPRGGNTVYNEKFKG |
| 10 | KISNRFS |
| 11 | NYRSTFGY |
| 12 | $WIYPX_4GX_5X_6X_7X_8YX_9EKFKG$ |
| 13 | QVQLQQSGPELVRPGASVKISCKASGYRFTRNYFHWVKQRPGQGLE WIGWIYPGGFDIEYSEKFKGKATLTTDTSSSTAYMLLTSLTSEDSAVY YCAINYGSTFGYWGQGTLVTVSV |
| 14 | DVLMTQTPLSLPVSLGDQASISCRSSQNIVHSNGNTYLEWYLQRPGQS PKLLIYKVSNRFSGVPDRFSGSGSGTDFTLKINRVEAEDLGVYYCFQG SHVPFTFGSGTKLEIK |
| 15 | QVQLQQSGPELMKPGASLQISCKASGYFFTTYYIHWVKQRPGQGLE WIGWIYPRGGNTVYNEKFKGKATLTSDTSSSTAYMQLSSLTSEDSAV YYCAINYRSTFGYWGQGTLVTVSA |
| 16 | DVLMTQTPLSLPVSLGDQASISCRSSQNIVHSNGNTYLEWYLQKPGQS PKLLIYKISNRFSGVPDRFSGSGSGTDFTLKISRVEAEDLGVYYCFQGS HVPFTFGSGTKLEIK |
| 17 | AKTTPPSVYPLAPGSAAQTNSMVTLGCLVKGYFPEPVTVTWNSGSLS SGVHTFPAVLQSDLYTLSSSVTVPSSTWPSQTVTCNVAHPASSTKVDK KIVPRDCGCKPCICTVPEVSSVFIFPPKPKDVLTITLTPKVTCVVVDISK DDPEVQFSWFVDDVEVHTAQTKPREEQINSTFRSVSELPIMHQDWLN GKEFKCRVNSAAFPAPIEKTISKTKGRPKAPQVYTIPPPKEQMAKDKV SLTCMITNFFPEDITVEWQWNGQPAENYKNTQPIMDTDGSYFVYSKL NVQKSNWEAGNTFTCSVLHEGLHNHHTEKSLSHSPGK |
| 18 | RADAAPTVSIFPPSSEQLTSGGASVVCFLNNFYPKDINVKWKIDGSER QNGVLNSWTDQDSKDSTYSMSSTLTLTKDEYERHNSYTCEATHKTST SPIVKSFNRNEC |
| 19 | DQWSTQDLYN |

Figure 11

| | |
|---|---|
| 20 | MAVTACQGLGFVVSLIGIAGIIAATCMDQWSTQDLYNNPVTAVFNYQGLWRSCVRESSGFTECRGYFTLLGLPAMLQAVRALMIVGIVLGAIGLLVSIFALKCIRIGSMEDSAKANMTLTSGIMFIVSGLCAIAGVSVFANMLVTNFWMSTANMYTGMGGMVQTVQTRYTFGAALFVGWVAGGLTLIGGVMMCIACRGLAPEETNYKAVSYHASGHSVAYKPGGFKASTGFGSNTKNKKIYDGGARTEDEVQSYPSKHDYV |
| 21 | MSTTTCQVVAFLLSILGLAGCIAATGMDMWSTQDLYDNPVTSVFQYEGLWRSCVRQSSGFTECRPYFTILGLPAMLQAVRALMIVGIVLGAIGLLVSIFALKCIRIGSMEDSAKANMTLTSGIMFIVSGLCAIAGVSVFANMLVTNFWMSTANMYTGMGGMVQTVQTRYTFGAALFVGWVAGGLTLIGGVMMCIACRGLAPEETNYKAVSYHASGHSVAYKPGGFKASTGFGSNTKNKKIYDGGARTEDEVQSYPSKHDYV |
| 22 | QIQLVQSGPELKKFGETVKISCKASGYTFTDYSIHWVKQAPGKGLKWMGWINTETGVPTYADDFKGRFAFSLETSASTAYLQINNLKNEDTATYFCARRTGFDYWGQGTTLTVSS |
| 23 | DIVMTQAAFSIPVTLGTSASISCRSSKNLLHSDGITYLYWYLQRPGQSPQLLIYRVSNLASGVPNRFSGSESGTDFTLRISRVEAEDVGVYYCVQVLELPFTFGGGTKLEIK |
| 24 | NYX$_{10}$STFGY |
| 25 | KX$_{11}$SNRFS |
| 26 | ATCMDQWSTQDLYNNPVTAVFNYQGLWRSCVRESSGFTECRGYFTLLGLPAMLQAVRA |
| 27 | DMWSTQDLYDNPVTSVFQYEGLWRSCVRQSSGFTECRPYFTILGLPAML |

Figure 11 (continued)

ANTI-CLDN18.2 ANTIBODIES AND DIAGNOSTIC USES THEREOF

FIELD OF THE INVENTION

The present disclosure generally relates to novel anti-CLDN18.2 antibodies and diagnostic uses thereof.

BACKGROUND

The Claudin-18 (CLDN18) molecule (Genbank accession number: splice variant 1 (CLDN18A1 or CLDN18.1): NP_057453, NM_016369, and splice variant 2 (CLDN18A2 or CLDN18.2): NM_001002026, NP_001002026) is an integral transmembrane protein with a molecular weight of approximately 27.9/27.72 kD. CLDN18 proteins are located within the tight junctions of epithelia and endothelia that organize a network of interconnected strands of intramembranous particles between adjacent cells. CLDN18 and occludin are the most prominent transmembrane protein components in the tight junctions. Due to their strong intercellular adhesion properties, these tight junction proteins create a primary barrier to prevent and control the paracellular transport of solutes, and also restrict the lateral diffusion of membrane lipids and proteins to maintain cellular polarity. Therefore, they are critically involved in organizing epithelial tissue architecture.

Although targeted therapy and immunotherapy have revolutionized systemic treatment of various cancers in the past decade, management of advanced and/or metastatic cancers is still a great challenge. For example, many patients with advanced gastrointestinal cancers such as gastric cancer, pancreatic cancer, cholangiocarcinoma, or lung cancer still do not significantly benefit from current standard-of-care. Chemotherapy still remains the mainstream treatment for most of these advanced stage cancer patients and their prognosis is still very poor. Given the highly restricted expression and its frequent ectopic activation of CLDN18.2 in a broad type of tumors, CLDN18.2 is considered as a therapeutic target for the development of agents for the treatment CLDN18.2 expressing solid tumors which included but not limited to GC/GEC, pancreatic cancer, cholangiocarcinoma, and lung cancer, etc.

To enable screening and selection of patients with CLDN18.2 expression, an IHC detection assay with high specificity and affinity is desired.

BRIEF SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides, among others, novel monoclonal anti-CLDN18.2 antibodies which specifically recognize CLDN18.2 without cross-reacting with CLDN18.1. The present disclosure further provides nucleotide sequences encoding such anti-CLDN18.2 antibodies, and use of such anti-CLDN18.2 antibodies, for example, for diagnostic purposes.

In one aspect, the present disclosure provides an isolated monoclonal antibody or an antigen binding fragment thereof that specifically bind to CLDN18.2, wherein the antibody or an antigen binding fragment thereof exhibits one or more of the following characteristics:

a) having no cross-reactivity to human CLDN18.1;
b) having no cross-reactivity to non-cancerous cells except stomach epithelial cells as measured by Immunohistochemistry assay (IHC);
c) having no cross-reactivity to non-cancerous human lung tissue as measured by IHC;
d) capable of specifically binding to CLDN18.2-expressing cells, optionally the CLDN18.2-expressing cells are pre-treated such that CLDN18.2 is denatured or otherwise no longer in its native conformation;
e) capable of binding to a fusion polypeptide comprising first extracellular loop of human CLDN18.2 at a $K_d$ value of no more than 10 nM as measured by Surface Plasmon resonance (SPR), or at an EC50 value of no more than 20 ng/ml as measured by enzyme-linked immunosorbent assays (ELISA);
f) showing no detectable binding to cell surface human CLDN 18.2 as measured by flow cytometry (FACS) assay;
g) capable of specifically binding to an epitope within the amino acid sequence of DQWSTQDLYN (SEQ ID NO: 19) as measured by ELISA; and/or
h) having no cross-reactivity to human CLDN18.1 in a formalin-fixed paraffin-embedded (FFPE) sample at an antibody concentration of 1 nM as measured by ELISA or at an antibody concentration of 0.5 ug/ml as measured by IHC.

In one aspect, the present disclosure provides an isolated antibody or an antigen binding fragment thereof that specifically bind to CLDN18.2, comprising:

a) a heavy chain CDR1 comprising the amino acid sequence of $X_1X_2YX_3H$ (SEQ ID NO: 8), a heavy chain CDR2 comprising the amino acid sequence of $WIYPX_4GX_5X_6X_7X_8YX_9EKFKG$ (SEQ ID NO: 12), and a heavy chain CDR3 comprising the amino acid sequence of $NYX_{10}STFGY$ (SEQ ID NO: 24); and/or
b) a light chain CDR1 comprising the amino acid sequence of RSSQNIVHSNGNTYLE (SEQ ID NO: 2), a light chain CDR2 comprising the amino acid sequence of $KX_{11}SNRFS$ (SEQ ID NO: 25), and a light chain CDR3 comprising the amino acid sequence of FQGSHVPFT (SEQ ID NO: 6);

wherein $X_1$ is R or T, $X_2$ is N or Y, $X_3$ is F or I, $X_4$ is G or R, $X_5$ is F or G, $X_6$ is D or N, $X_7$ is I or T, $X_8$ is E or V, $X_9$ is S or N, $X_{10}$ is G or R, and $X_{11}$ is V or I.

In certain embodiments, the isolated antibody or an antigen binding fragment thereof comprising:

a) a heavy chain CDR1 comprising the amino acid sequence of SEQ ID NO: 1, a heavy chain CDR2 comprising the amino acid sequence of SEQ ID NO: 3, and a heavy chain CDR3 comprising the amino acid sequence of SEQ ID NO: 5; or
b) a heavy chain CDR1 comprising SEQ ID NO: 7, a heavy chain CDR2 sequence comprising SEQ ID NO: 9, and a heavy chain CDR3 sequence comprising SEQ ID NO: 11.

In certain embodiments, the antibody or an antigen binding fragment thereof provided herein further comprising:

a) a light chain CDR1 comprising the amino acid sequence of SEQ ID NO: 2, a light chain CDR2 comprising the amino acid sequence of SEQ ID NO: 4, and a light chain CDR3 comprising the amino acid sequence of SEQ ID NO: 6; or
b) a light chain CDR1 comprising the amino acid sequence of SEQ ID NO: 2, a light chain CDR2 comprising the amino acid sequence of SEQ ID NO: 10, and a light chain CDR3 comprising the amino acid sequence of SEQ ID NO: 6.

In certain embodiments, the antibody or an antigen binding fragment thereof provided herein comprising:

a) a heavy chain CDR1 comprising the amino acid sequence of SEQ ID NO: 1, a heavy chain CDR2 comprising the amino acid sequence of SEQ ID NO: 3, a heavy chain CDR3 comprising the amino acid sequence of SEQ ID NO: 5, a light chain CDR1 comprising the amino acid sequence of SEQ ID NO: 2, a light chain CDR2 comprising the amino acid sequence of SEQ ID NO: 4, and a light chain CDR3 comprising the amino acid sequence of SEQ ID NO: 6; or b) a heavy chain CDR1 comprising the amino acid sequence of SEQ ID NO: 7, a heavy chain CDR2 comprising the amino acid sequence of SEQ ID NO: 9, a heavy chain CDR3 comprising the amino acid sequence of SEQ ID NO: 11, a light chain CDR1 comprising the amino acid sequence of SEQ ID NO:2, a light chain CDR2 comprising the amino acid sequence of SEQ ID NO: 10, and a light chain CDR3 comprising the amino acid sequence of SEQ ID NO: 6.

In certain embodiments, the antibody or an antigen binding fragment thereof provided herein comprising:

a) a heavy chain variable region comprising the amino acid sequence of SEQ ID NO: 13, and a light chain variable region comprising the amino acid sequence of SEQ ID NO: 14; or b) a heavy chain variable region comprising the amino acid sequence of SEQ ID NO: 15, and a light chain variable region comprising the amino acid sequence of SEQ ID NO: 16.

In certain embodiments, the antibody or antigen-binding fragment thereof provided herein further comprising one or more amino acid residue mutations yet retaining binding specificity to human CLDN 18.2, and optionally retaining binding specificity to a linear epitope comprising the amino acid sequence of SEQ ID NO: 19.

In certain embodiments, at least one of the mutations are conservative substitutions, or all of the mutations are conservative substitutions.

In certain embodiments, at least one of the mutations is in one or more of the CDR sequences, and/or in one or more of the non-CDR sequences of the heavy chain variable region or light chain variable region.

In certain embodiments, the antibody or antigen-binding fragment thereof comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 1 or SEQ ID NO: 7, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 3 or SEQ ID NO: 9, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 5 or SEQ ID NO: 11, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 2, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 4 or SEQ ID NO: 10, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 6, and in the meantime retain the binding specificity to CLDN18.2, optionally having binding affinity at a level similar to or even higher than its parent antibody.

In certain embodiments, the antibody or antigen-binding fragment thereof comprises an HCDR1 having no more than 3, 2, or 1 amino acid mutations in SEQ ID NO: 1 or SEQ ID NO: 7, an HCDR2 having no more than 6, 5, 4, 3, 2, or 1 amino acid mutations in SEQ ID NO: 3 or SEQ ID NO: 9, an HCDR3 having no more than 6, 5, 4, 3, 2, or 1 amino acid mutations in SEQ ID NO: 5 or SEQ ID NO: 11, a LCDR1 having no more than 2 or 1 amino acid mutations in SEQ ID NO: 2, a LCDR2 having no more than 3, 2, or 1 amino acid mutations in SEQ ID NO: 4 or SEQ ID NO: 10, and/or a LCDR3 having no more than 3, 2, or 1 amino acid mutations in SEQ ID NO: 6, and in the meantime retain the binding specificity to CLDN18.2, and optionally having binding affinity at a level similar to or even higher than its parent antibody.

In certain embodiments, the heavy chain variable region comprises an amino acid sequence having at least 80% sequence identity to SEQ ID NO: 13 or SEQ ID NO: 15, and/or the light chain variable region comprises an amino acid sequence having at least 80% sequence identity to SEQ ID NO: 14 or SEQ ID NO: 16.

In certain embodiments, the antibody or antigen-binding fragment thereof provided herein further comprises an immunoglobulin constant region, optionally comprising a heavy chain constant region of IgG, and/or a light chain constant region. In certain embodiments, the constant region comprises a mouse constant region, a rabbit constant region, a human constant region or any other suitable constant region.

In certain embodiments, the heavy chain constant region comprises an amino acid sequence of SEQ ID NO: 17 or a sequence having at least 80% sequence identity thereof, and/or the light chain constant region comprises an amino acid sequence of SEQ ID NO: 18 or a sequence having at least 80% sequence identity thereof.

In certain embodiments, the antibody or antigen-binding fragment thereof provided herein is a monoclonal antibody, a bispecific antibody, a multi-specific antibody, a recombinant antibody, a chimeric antibody, a humanized antibody, a labeled antibody, a bivalent antibody, an anti-idiotypic antibody, a fusion protein, a dimerized or polymerized antibody, or a modified antibody (e.g. glycosylated antibody).

In certain embodiments, the antibody or antigen-binding fragment thereof provided herein is a diabody, a Fab, a Fab', a F(ab')2, a Fd, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a NANOBODY®, a domain antibody, or a bivalent domain antibody.

In certain embodiments, the antibody or antigen-binding fragment thereof provided herein is linked to one or more moieties. In certain embodiments, the moiety comprises a radioactive isotope, a lanthanide, a chemluminescent label, a chromophoric moiety, colloidal gold particles, a fluorescent label, an enzyme-substrate label, a digoxigenin label, biotin/avidin, a hapten, a DNA molecule for detection or particle labels. In certain embodiments, the moiety comprises a biotin or a hapten.

In another aspect, the present disclosure provides a monoclonal antibody or an antigen-binding fragment thereof, which competes for binding to CLDN18.2 with the antibody or antigen-binding fragment thereof provided herein.

In another aspect, the present disclosure provides an isolated polynucleotide encoding the antibody or an antigen-binding fragment thereof provided herein. In another aspect, the present disclosure provides a vector comprising the isolated polynucleotide provided herein. In another aspect, the present disclosure provides a host cell comprising the vector provided herein.

In yet another aspect, the present disclosure provides a method of expressing the antibody or antigen-binding fragment thereof provided herein, comprising culturing the host cell provided herein under the condition at which the vector provided herein is expressed.

In yet another aspect, the present disclosure provides a method of detecting presence or expression level of CLDN18.2 in a sample, comprising contacting the sample with the antibody or antigen-binding fragment thereof provided herein under condition that allow specific binding of the antibody or antigen-binding fragment thereof to human CLDN18.2, and determining the presence or expression level of CLDN18.2 in the sample.

In yet another aspect, the present disclosure provides a method for diagnosing a CLDN18.2-associated disease or condition (e.g. cancer) in a subject, comprising:

a) contacting a sample obtained from the subject with the antibody or antigen-binding fragment thereof provided herein under conditions that allow specific binding of the antibody or antigen-binding fragment thereof to CLDN18.2; and b) determining presence or expression level of CLDN18.2 in the sample;

wherein the subject is diagnosed as having a CLDN18.2-associated disease or condition (e.g. cancer) when the presence of CLDN18.2 is found or when the expression level of CLDN18.2 reaches a threshold level.

In yet another aspect, the present disclosure provides a method for determining the eligibility of a subject having or at risk of a CLDN18.2-associated disease or condition for treatment with a CLDN18.2-targeting agent, comprising:

a) contacting a sample obtained from the subject with the antibody or antigen-binding fragment thereof provided herein under condition that allow specific binding of the antibody or antigen-binding fragment thereof to CLDN18.2;

b) determining presence or expression level of CLDN18.2 in the sample;

wherein the subject is determined as eligible for treatment with a CLDN18.2-targeting agent when the presence of CLDN18.2 is found or when the expression level of CLDN18.2 reaches a threshold level, or wherein the subject is determined as not eligible for treatment with a CLDN18.2-targeting agent when the presence of CLDN18.2 is not found or when the expression level of CLDN18.2 is below a threshold level.

In yet another aspect, the present disclosure provides a method of predicting therapeutic effectiveness of a claudin18.2-targeting agent in treating a CLDN18.2-associated disease or condition in a subject, comprising:

a) contacting a sample obtained from the subject with the antibody or antigen-binding fragment thereof provided herein under condition that allow specific binding of the antibody or antigen-binding fragment thereof to CLDN18.2;

b) determining presence or expression level of human CLDN18.2 in the sample;

c) predicting the therapeutic effectiveness of the CLDN18.2-targeting agent, wherein the CLDN18.2-targeting agent is predicted to be effective in treating the subject when the presence of CLDN18.2 is found or when the expression level of CLDN18.2 reaches a threshold level, or wherein the claudin18.2-targeting agent is predicted to be not effective in treating the subject when the presence of CLDN18.2 is not found or when the expression level of CLDN18.2 is below the threshold level.

In yet another aspect, the present disclosure provides a method of treating a subject having or at risk of a CLDN18.2-associated disease or condition, comprising:

a) selecting a subject that is suitable for the treatment, comprising:

i) contacting a sample obtained from the subject with the antibody or antigen-binding fragment thereof provided herein under condition that allow specific binding of the antibody or antigen-binding fragment thereof to CLDN18.2;

ii) determining the presence or expression level of human CLDN18.2 in the sample;

iii) selecting the subject as suitable for the treatment of the CLDN18.2-associated disease or condition when the presence of CLDN18.2 is found or when the expression level of CLDN18.2 in the sample reaches a threshold level;

b) administering a therapeutically effective amount of CLDN18.2-targeting agent to the selected subject.

In yet another aspect, the present disclosure provides a method of treating a subject having or at risk of cancer, comprising:

a) selecting a subject comprising:

i) contacting a sample obtained from the subject with the antibody or antigen-binding fragment thereof provided herein under condition that allow specific binding of the antibody or antigen-binding fragment thereof to CLDN18.2;

ii) determining the presence or expression level of CLDN18.2 in the sample;

iii) selecting the subject as not suitable for the treatment of the CLDN18.2-associated disease or condition when the presence of CLDN18.2 is not found or when the expression level of CLDN18.2 in the sample is below a threshold level;

b) administering to the selected subject a Standard-of-Care Therapeutic other than a CLDN18.2-targeting agent.

In certain embodiments, the sample is a cell sample or a tissue sample. In certain embodiments, the sample is a fixed tissue sample, optionally a formalin-fixed paraffin-embedded (FFPE) tissue sample. In certain embodiments, the CLDN18.2 is cell surface or membrane-bound CLDN18.2.

In certain embodiments, the presence or expression level of CLDN18.2 is determined by immunohistochemistry (IHC), immunocytochemistry (ICC), immunofluorescence (IF), enzyme immunoassay (EIA), Enzyme-Linked Immunosorbant Assay (ELISA), or immunoblotting.

In certain embodiments, the expression level is quantified based on percentage of positively-stained cells in the sample. In certain embodiments, the expression level is quantified based on staining intensity for CLDN18.2 in the sample.

In certain embodiments, the CLDN18.2-associated disease or condition is cancer. In certain embodiments, the sample comprises a tumor sample. In certain embodiments, the tumor sample comprises a tumor tissue or a circulating tumor cell. In certain embodiments, the cancer is primary cancer or metastatic cancer.

In certain embodiments, the CLDN18.2-associated disease or condition is cancer. In certain embodiments, the cancer is primary cancer or metastatic cancer. In certain embodiments, the cancer is gastric cancer, lung cancer (non-small cell lung cancer or small cell lung cancer), bronchial cancer, bone cancer, liver and bile duct cancer, pancreatic cancer, breast cancer, liver cancer, ovarian cancer, testicle cancer, kidney cancer, bladder cancer, head and neck cancer, spine cancer, brain cancer, cervix cancer, uterine cancer, endometrial cancer, colon cancer, colorectal cancer, rectal cancer, anal cancer, esophageal cancer, gastrointestinal cancer, skin cancer, prostate cancer, pituitary cancer, stomach cancer, vagina cancer, thyroid cancer, glioblastoma, astrocytoma, melanoma, myelodysplastic syndrome, sarcoma, teratoma, cholangiocarcinoma, and/or adenocarcinoma.

In certain embodiments, the cancer is gastric cancer, pancreatic cancer, cholangiocarcinoma, or lung cancer. In certain embodiments, the lung cancer is non-small cell lung cancer or small cell lung cancer (NSCLC or SCLC).

In certain embodiments, the CLDN18.2-targeting agent is capable of inducing cytotoxicity to CLDN18.2-expressing cells. In certain embodiments, the CLDN18.2-targeting agent is a therapeutic anti-CLDN18.2 antibody or CLDN18.2-binding molecule, a CLDN18.2-targeting cell therapy, a chemical compound targeting CLDN18.2, or a therapeutic nucleic acid targeting CLDN18.2.

In certain embodiments, the therapeutic anti-CLDN18.2 antibody or CLDN18.2-binding molecule is conjugated to a cytotoxic agent. In certain embodiments, the therapeutic anti-CLDN18.2 antibody is a bispecific antibody. In certain embodiments, the CLDN18.2-targeting cell therapy includes a CAR-T (Chimeric Antibody Receptor Engineered T Cell), TCR-T (Gene Modified TCR T cell) or CAR-NK (Chimeric Antibody Receptor Engineered NK Cell) expressing a CLDN18.2-binding chimeric antibody receptor (CAR).

In certain embodiments, the subject is receiving or has received anti-cancer-therapy, or suffers from cancer recurrence.

In yet another aspect, the present disclosure provides a kit comprising the isolated antibody or antigen-binding fragment thereof provided herein.

In certain embodiments, the kit further comprising a set of reagents for detecting a complex of the antibody or antigen-binding fragment thereof bound to CLDN18.2. In certain embodiments, the set of reagents comprises an anti-mouse antibody.

BRIEF DESCRIPTION OF FIGURES

FIG. 11 shows all the sequences in this application.

DETAILED DESCRIPTION OF THE INVENTION

Figure 1:
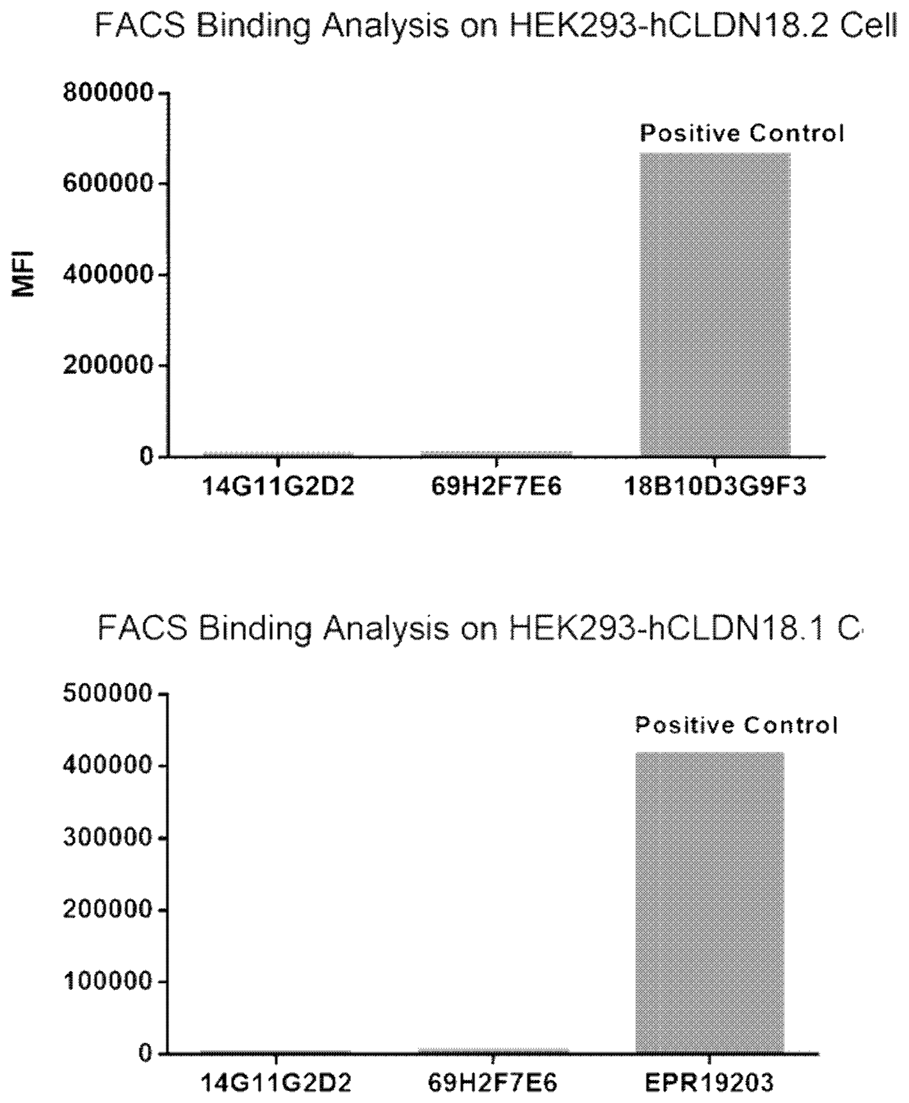
FIG. 1 shows FACS analysis of anti-CLDN18.2 antibodies, 69H2F7E6, 14G11G2D2, binding to HEK293-hCLDN18.2 cell and HEK293-hCLDN18.1 cell. Antibodies 18B10D3G9F3 and EPR19202 are used as positive controls.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

As used herein, the term "a," "an," "the" and similar terms used in the context of the present invention (especially in the context of the claims) are to be construed to cover both the singular and plural unless otherwise indicated herein or clearly contradicted by the context.

The term "antibody" as used herein includes any immunoglobulin, monoclonal antibody, polyclonal antibody, multivalent antibody, bivalent antibody, monovalent antibody, multispecific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as λ or κ, while each light chain consists of a variable region ($V_L$)

and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, and HCDR3). CDR boundaries for the antibodies and antigen-binding domains disclosed herein may be defined or identified by the conventions of Kabat, IMGT, AbM, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J.Mol.Biol., 196,901 (1987); N. R. Whitelegg et al, Protein Engineering, v13(12), 819-824 (2000); Chothia, C. et al., Nature. December 21-28; 342(6252):877-83 (1989); Kabat E. A. et al., National Institutes of Health, Bethesda, Md. (1991); Marie-Paule Lefranc et al, Developmental and Comparative Immunology, 27: 55-77 (2003); Marie-Paule Lefranc et al, Immunome Research, 1(3), (2005); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgAQ1 (alpha1 heavy chain), or IgA2 (alpha2 heavy chain). The present disclosure includes all antibodies and derivatives of antibodies as described herein which for the purposes of the invention are encompassed by the term "antibody". The term "antibody derivatives" refers to any modified form of an antibody, e.g., a conjugate of the antibody and another agent, an antibody fragment, or a fusion protein comprising the antibody or the antibody fragment.

As used herein, the term "antigen-binding fragment" refers to an antibody fragment formed from a fragment of an antibody comprising one or more CDRs, or any other antibody portion that binds to an antigen but does not comprise an intact native antibody structure. Examples of antigen-binding fragment include, without limitation, a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody fragment, a camelized single domain antibody, a NANOBODY®, a domain antibody, and a bivalent domain antibody. An antigen-binding fragment is capable of binding to the same antigen to which the parent antibody binds. In certain embodiments, an antigen-binding fragment may comprise one or more CDRs from a particular antibody.

"Fab" with regard to an antibody refers to a monovalent antigen-binding fragment of the antibody consisting of a single light chain (both variable and constant regions) bound to the variable region and first constant region of a single heavy chain by a disulfide bond. Fab can be obtained by papain digestion of an antibody at the residues proximal to the N-terminus of the disulfide bond between the heavy chains of the hinge region.

"Fab'" refers to a Fab fragment that includes a portion of the hinge region, which can be obtained by pepsin digestion of an antibody at the residues proximal to the C-terminus of the disulfide bond between the heavy chains of the hinge region and thus is different from Fab in a small number of residues (including one or more cysteines) in the hinge region.

"F(ab')$_2$" refers to a dimer of Fab' that comprises two light chains and part of two heavy chains.

"Fc" with regard to an antibody refers to that portion of the antibody consisting of the second and third constant regions of a first heavy chain bound to the second and third constant regions of a second heavy chain via disulfide bond. IgG and IgM Fc regions contain three heavy chain constant regions (second, third and fourth heavy chain constant regions in each chain). It can be obtained by papain digestion of an antibody. The Fc portion of the antibody is responsible for various effector functions such as ADCC, ADCP and CDC, but does not function in antigen binding.

"Fv" with regard to an antibody refers to the smallest fragment of the antibody to bear the complete antigen binding site. A Fv fragment consists of the variable region of a single light chain bound to the variable region of a single heavy chain. A "dsFv" refers to a disulfide-stabilized Fv fragment that the linkage between the variable region of a single light chain and the variable region of a single heavy chain is a disulfide bond.

"Single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA,* 85:5879 (1988)). A "scFv dimer" refers to a single chain comprising two heavy chain variable regions and two light chain variable regions with a linker. In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, a "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

"Single-chain Fv-Fc antibody" or "scFv-Fc" refers to an engineered antibody consisting of a scFv connected to the Fc region of an antibody.

"Camelized single domain antibody," "heavy chain antibody," "NANOBODY®" or "HCAb" refers to an antibody that contains two $V_H$ domains and no light chains (Riechmann L. and Muyldermans S., *J Immunol Methods*. December 10; 231(1-2):25-38 (1999); Muyldermans S., *J Biotechnol*. June; 74(4):277-302 (2001); WO94/04678; WO94/25591; U.S. Pat. No. 6,005,079). Heavy chain antibodies were originally obtained from Camelidae (camels, dromedaries, and llamas). Although devoid of light chains, camelized antibodies have an authentic antigen-binding repertoire (Hamers-Casterman C. et al., *Nature*. June 3; 363

(6428):446-8 (1993); Nguyen V K. et al. "Heavy-chain antibodies in Camelidae; a case of evolutionary innovation," Immunogenetics. April; 54(1):39-47 (2002); Nguyen V K. et al. *Immunology*. May; 109(1):93-101 (2003)). The variable domain of a heavy chain antibody (VHH domain) represents the smallest known antigen-binding unit generated by adaptive immune responses (Koch-Nolte F. et al., *FASEB J.* November; 21(13):3490-8. Epub 2007 Jun. 15 (2007)).

"Diabodies" include small antibody fragments with two antigen-binding sites, wherein the fragments comprise a $V_H$ domain connected to a $V_L$ domain in a single polypeptide chain ($V_H$-$V_L$ or $V_L$-$V_H$) (see, e.g., Holliger P. et al., *Proc Natl Acad Sci USA*. July 15; 90(14):6444-8 (1993); EP404097; WO93/11161). The two domains on the same chain cannot be paired, because the linker is too short, thus, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain embodiments, two or more $V_H$ domains are covalently joined with a peptide linker to form a bivalent or multivalent domain antibody. The two $V_H$ domains of a bivalent domain antibody may target the same or different antigens.

A "$(dsFv)_2$" refers to disulfide-stabilized Fv fragments comprising three peptide chains: two $V_H$ moieties linked by a peptide linker and bound by disulfide bridges to two $V_L$ moieties.

A "bispecific ds diabody" refers to a diabody targeting two different antigens (or epitopes). It can comprise $V_{H1}$-$V_{L2}$ (linked by a peptide linker) bound to $V_{L1}$-$V_{H2}$ (also linked by a peptide linker) via a disulfide bridge between $V_H1$ and $V_L1$.

A "bispecific dsFv" or "dsFv-dsFv" refers to a disulfide-stabilized Fv fragments targeting two different antigens (or epitopes). It can comprise three peptide chains: a $V_{H1}$-$V_{H2}$ moiety wherein the heavy chains are bound by a peptide linker (e.g., a long flexible linker) and paired via disulfide bridges to $V_{L1}$ and $V_{L2}$ moieties, respectively. Each disulfide paired heavy and light chain has a different antigen specificity.

The term "humanized" as used herein means that the antibody or antigen-binding fragment comprises CDRs derived from non-human animals, FR regions derived from human, and when applicable, constant regions derived from human.

The term "chimeric" as used herein refers to an antibody or antigen-binding fragment that has a portion of heavy and/or light chain derived from one species, and the rest of the heavy and/or light chain derived from a different species. In an illustrative example, a chimeric antibody may comprise a constant region derived from human and a variable region derived from a non-human species, such as from mouse.

"Anti-CLDN18.2 antibody" or "an antibody against CLDN18.2" as used herein refers to an antibody that is capable of specific binding to CLDN18.2 (e.g. human or non-human CLDN18.2) with a sufficient affinity, for example, to provide for diagnostic and/or therapeutic use.

The term "affinity" as used herein refers to the strength of non-covalent interaction between an immunoglobulin molecule (i.e. antibody) or fragment thereof and an antigen.

The term "specific binding" or "specifically binds" or "binding specificity" as used herein refers to a non-random binding reaction between two molecules, such as for example between an antibody and an antigen.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum correspondence. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

The term "amino acid" as used herein refers to an organic compound containing amine ($—NH_2$) and carboxyl (—COOH) functional groups, along with a side chain specific to each amino acid. The names of amino acids are also represented as standard single letter or three-letter codes in the present disclosure, which are summarized as follows.

| Name of Amino Acid | Three-letter Code | Single-letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gin), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An isolated "nucleic acid" or "polynucleotide" are used interchangeably and refer to the sequence of an isolated nucleic acid molecule. In certain embodiments, an "isolated antibody or antigen-binding fragment thereof" refers to the antibody or antigen-binding fragments having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "subject" includes human and non-human animals. Non-human animals include all vertebrates, e.g., mammals and non-mammals, such as non-human primates, rodent (e.g. mouse, rat and guinea pigs), cat, rabbit, sheep, dog, cow, chickens, amphibians, and reptiles. In more preferred embodiments, the subject is a human. Except when noted, the terms "patient", "subject" and "individual" are used herein interchangeably.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and antibody dependent cell mediated phagocytosis (ADCP), where nonspecific cytotoxic cells that express FcγRs recognize bound antibody on a target cell and subsequently cause phagocytosis of the target cell. Effector functions include both those that operate after the binding of an antigen and those that operate independent of antigen binding.

"Treating" or "treatment" or "therapy" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases. In the context of the present invention, terms such as "protect", "prevent", "prophylactic" relate to the prevention or treatment or both of the occurrence and/or the propagation of a disease in a subject and, in particular, to minimizing the chance that a subject will develop a disease or to delaying the development of a disease. For example, a person at risk of a tumor, as described above, would be a candidate for therapy to prevent a tumor. Immunotherapy may be performed using any of a variety of techniques, in which agents function to remove antigen-expressing cells from a patient.

"Standard-of-Care" therapeutics described herein comprise the administration of a standard-of-care therapeutic to a patient. As used herein, a "standard-of-care therapeutic" is a treatment process, including a drug or combination of drugs, radiation therapy (RT), surgery or other medical intervention that is recognized by medical practitioners as appropriate, accepted, and/or widely used for a certain type of patient, disease or clinical circumstance. Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2013).

The terms "effective" and "effectiveness" with regard to a treatment include both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

A "therapeutically effective amount" or "therapeutically effective dosage" of a drug or therapeutic agent, such as an antibody of the present disclosure, is any amount of the drug that, when used alone or in combination with another therapeutic agent, protects a subject against the onset of a disease or condition, or promotes disease/condition regression evidenced by a decrease in severity of disease/condition symptoms, an increase in frequency and duration of disease/condition symptom-free periods, or a prevention of impairment or disability due to the disease/condition affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays. A therapeutically effective amount of a drug includes a "prophylactically effective amount," which is any amount of the drug that, when administered alone or in combination with an anti-neoplastic agent to a subject at risk of developing a CLDN18.2-associated disease or condition, such as a cancer (e.g., a subject having a pre-malignant condition) or of suffering a disease/condition recurrence, inhibits the development or recurrence of the disease/condition. In preferred embodiments, the prophylactically effective amount prevents the development or recurrence of the CLDN18.2-associated disease or condition (e.g. cancer) entirely. "Inhibiting" the development or recurrence of a disease/condition (e.g. cancer) means either lessening the likelihood of the disease/condition's development or recurrence, or preventing the development or recurrence of the disease/condition entirely.

The term "vector" as used herein refers to a vehicle into which a genetic element may be operably inserted so as to bring about the expression of that genetic element, such as to produce the protein, RNA or DNA encoded by the genetic element, or to replicate the genetic element.

The "host cell" as used herein refers to a cell into which an exogenous polynucleotide and/or a vector has been introduced.

The term "CLDN18" refers to claudin 18 and includes any splice variants such as CLDN18.1 and CLDN18.2 of CLDN18. CLDN18.1 and CLDN18.2 differ in the N-terminal portion which comprises the first transmembrane (TM) region and loop 1, whereas the primary protein sequence of the C-terminus is identical.

The term "CLDN18.2" refers to Claudin-18 splice variant 2 derived from mammals, such as primates (e.g. humans, monkeys) and rodents (e.g. mice). In certain embodiments, CLDN18.2 is human CLDN18.2. Exemplary sequence of human CLDN18.2 includes human CLDN18.2 protein (NCBI Ref Seq No. NP_001002026.1, or SEQ ID NO: 20). Exemplary sequence of CLDN18.2 includes *Mus musculus* (mouse) CLDN18.2 protein (NCBI Ref Seq No. NP_001181852.1), *Macaca fascicularis* (crab-eating macaque) CLDN18.2 protein (NCBI Ref Seq No. XP_015300615.1).

The term "CLDN18.1" refers to Claudin-18 splice variant 1 derived from mammals, such as primates (e.g. humans, monkeys) and rodents (e.g. mice). In certain embodiments, CLDN18.1 is human CLDN18.1. Exemplary sequence of human CLDN18.1 includes human CLDN18.1 protein (NCBI Ref Seq No. NP_057453.1, or SEQ ID NO: 21), *Mus musculus* (mouse) CLDN18.2 protein (NCBI Ref Seq No. NP_001181851.1), *Macaca fascicularis* (crab-eating macaque) CLDN18.2 protein (NCBI Ref Seq No. XP_005545920.1).

The term "CLDN18.2" and "CLDN18.2" also encompass variants of the exemplary sequences, such as mutants, conformation variants, isoforms, allelic variants, species variants and species homologs, in particular those which are naturally present.

A "CLDN18.2-associated disease or condition" as used herein refers to any disease or condition caused by, exacerbated by, or otherwise linked to increased or decreased expression or activities of CLDN18.2. In some embodiments, the CLDN18.2 related condition is, for example, cancer.

"Cancer" as used herein refers to any medical condition characterized by malignant cell growth or neoplasm, abnormal proliferation, infiltration or metastasis, and includes both solid tumors and non-solid cancers (e.g. hematologic malignancies) such as leukemia.

As used herein "solid tumor" refers to a solid mass of neoplastic and/or malignant cells.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "metastasis" or "metastatic cancer" as used herein means the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. The cells of a secondary or metastatic tumor are like those in the original tumor. This means, for example, that, if gastric cancer metastasizes to the liver, the secondary tumor is made up of abnormal gastric cells, not of abnormal liver cells. The tumor in the liver is then called metastatic gastric cancer, not liver cancer.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

Anti-CLDN18.2 Antibodies

The present disclosure provides anti-CLDN18.2 antibodies and antigen-binding fragments thereof.

CLDN18.2 is a splice variant of Claudin-18 (CLDN18). CLDN18 is a member of the tetraspanin family and has 4 hydrophobic regions. CLDN18 displays several different conformations, which may be selectively addressed by antibodies (see Sahin U et al. Clinical Cancer Research, 2008, 14(23): 7624-7634). CLDN18-Conformation-1 has all four hydrophobic regions serving as the transmembrane domains (TM), and two extracellular loops (loop1 embraced by hydrophobic region 1 and hydrophobic region 2; loop2 embraced by hydrophobic region 3 and 4) are formed, as described for the vast majority of CLDN family members. A second conformation (CLDN18-Conformation-2) implies that, as described for PMP22, the second and third hydrophobic domains do not fully cross the plasma membrane so that portion (loop D3) between the first and fourth transmembrane domains is extracellular. A third conformation (CLDN18-Conformation-3) shows a large extracellular domain with two internal hydrophobic regions embraced by the first and fourth hydrophobic regions. Because of a classical N-glycosylation site in the loop D3, the CLDN-18 topology variants CLDN18 topology-2 and CLDN18 topology-3 harbor an additional extracellular N-glycosylation site.

CLDN18 has two different splice variants, which are present in both mouse and human. The splice variants CLDN18.1 and CLDN18.2 differ in the first 21 amino acids at the N-terminus that comprises the first (TM) and the loop1, whereas the protein sequences in the C-terminus are identical. Although these two isoforms share 92% identity in amino acid sequence, their expression patterns are mutually exclusive with CLDN18.1 being predominantly expressed in normal lung and CLDN18.2 in normal gastric tissue (see Niimi T, et al. Molecular and cellular biology, 2001, 21(21): 7380-7390.). The amino acid sequences for human CLDN18.1 and CLDN18.2 are shown below, respectively.

```
Human claudin18.2 (Accession: NP_001002026.1)
amino acid sequence (SEQ ID NO: 20):
MAVTACQGLGFVVSLIGIAGIIAATCMDQWSTQDLYNNPVTAVFNYQGLW

RSCVRESSGFTECRGYFTLLGLPAMLQAVRALMIVGIVLGAIGLLVSIFA

LKCIRIGSMEDSAKANMTLTSGIMFIVSGLCAIAGVSVFANMLVTNFWMS
```

-continued

```
TANMYTGMGGMVQTVQTRYTFGAALFVGWVAGGLTLIGGVMMCIACRGLA

PEETNYKAVSYHASGHSVAYKPGGFKASTGFGSNTKNKKIYDGGARTEDE

VQSYPSKHDYV

Human claudin18.1 (Accession: NP_057453.1)
amino acid sequence (SEQ ID NO: 21):
MSTTTCQVVAFLLSILGLAGCIAATGMDMWSTQDLYDNPVTSVFQYEGLW

RSCVRQSSGFTECRPYFTILGLPAMLQAVRALMIVGIVLGAIGLLVSIFA

LKCIRIGSMEDSAKANMTLTSGIMFIVSGLCAIAGVSVFANMLVTNFWMS

TANMYTGMGGMVQTVQTRYTFGAALFVGWVAGGLTLIGGVMMCIACRGLA

PEETNYKAVSYHASGHSVAYKPGGFKASTGFGSNTKNKKIYDGGARTEDE

VQSYPSKHDYV
```

In normal tissue, expression of CLDN18.2 is restricted to the basal membrane of mucosal cells and is not accessible to therapeutic antibodies. In pathologic conditions (such as tumor cells) the polarity of the gastric mucosa cells is perturbed and CLDN18.2 is exposed on the cell surface. CLDN18.2 protein is a pan-cancer target expressed in primary lesions and metastases of several human cancer types, including stomach, esophageal, pancreatic and lung tumors as well as human cancer cell lines (see Sahin Ugur et al, Clin Cancer Res 2008; 14(23); Matsuda Y et al. Cancer science, 2007, 98(7): 1014-1019.). Aberrant ectopic expression of CLDN18.2 has also been reported in pancreatic, ovarian, biliary and lung adenocarcinomas in multiple studies (see, for example, Karanjawala Z E et al, Am J Surg Pathol. 2008 February; 32(2):188-96; Micke P et al, Int J Cancer. 2014 Nov. 1; 135(9):2206-14; Keira Y et al, Virchows Arch. 2015 March; 466(3):265-77; Coati et al, Br J Cancer. 2019 July; 121(3):257-263; Dottermusch et al, Virchows Arch. 2019 November; 475(5):563-571; Rohde et al, Jpn J Clin Oncol. 2019 Sep. 1; 49(9):870-876; Woll et al, Int J Cancer. 2014 Feb. 1; 134(3):731-9; Espinoza et al, Histopathology. 2019 March; 74(4):597-607; Shinozaki et al, Virchows Arch. 2011 July; 459(1):73-80).

The present disclosure in one aspect provides monoclonal anti-CLDN18.2 antibodies and antigen-binding fragments thereof. The monoclonal anti-CLDN18.2 antibodies and antigen-binding fragments provided herein are capable of specifically binding to CLDN18.2 (e.g. human CLDN18.2), a fragment of CLDN18.2, or a fusion polypeptide comprising the fragment of CLDN18.2. In certain embodiments, the fragment of CLDN18.2 comprises the first extracellular loop of human CLDN18.2, or a sequence within the first extracellular loop of human CLDN18.2. In certain embodiments, the fragment of human CLDN18.2 comprises the amino acid sequence set forth in SEQ ID NO: 26 or SEQ ID NO: 19. In certain embodiments, the fusion polypeptide comprises additional amino acid residues attached to the N terminal and/or C terminal of the fragment of CLDN18.2. In certain embodiments, the fragment of CLDN18.2 contained in the fusion polypeptide forms a loop.

The anti-CLDN18.2 antibodies and antigen-binding fragments provided herein are capable of specifically binding to CLDN18.2-expressing cells. In certain embodiments, the CLDN18.2-expressing cells are pre-treated cells. The term "pre-treated" as used herein with respect to cells means that the cells have been treated such that its surface proteins such as CLDN18.2 are denatured or otherwise are no longer in its native conformation. For example, the CLDN18.2-expressing cells can be pre-treated by one or more chemical substances, for example formalin, paraffin or acetone, or by physical intervention such as freezing or heating. In certain embodiments, the CLDN18.2-expressing cells are formalin-fixed paraffin-embedded (FFPE) cells.

Binding of the anti-CLDN18.2 antibodies and antigen-binding fragments provided herein to the antigen can be represented by "half maximal effective concentration" ($EC_{50}$) value, which refers to the concentration of an antibody where 50% of its maximal effect (e.g., binding) is observed. The $EC_{50}$ value can be measured by methods known in the art, for example, sandwich assay such as ELISA, Western Blot, and other binding assay. The EC50 can be measured in a proper binding assay where serial dilutions of the antibody are tested for binding to the antigen, and the concentration at which 50% of maximal binding is determined. In certain embodiments, the anti-CLDN18.2 antibody or the antigen-binding fragment thereof provided herein specifically bind to human CLDN18.2, a fragment of human CLDN18.2, a fusion polypeptide comprising the fragment of human CLDN18.2, human CLDN18.2-expressing cells or pre-treated human CLDN18.2-expressing cells. In certain embodiments, the anti-CLDN18.2 antibody or the antigen-binding fragment thereof provided herein specifically binds to a fusion polypeptide comprising the first extracellular loop of human CLDN18.2 at an EC50 of no more than 50 ng/ml (e.g., no more than 40 ng/ml, no more than 35 ng/ml, no more than 30 ng/ml, no more than 20 ng/ml, no more than 18 ng/ml, no more than 16 ng/ml, no more than 15 ng/ml, no more than 14 ng/ml, no more than 13 ng/ml, no more than 12 ng/ml) as measured by ELISA.

Binding affinity to human CLDN18.2 of the anti-CLDN18.2 antibodies and antigen-binding fragments provided herein can also be characterized, for example by $K_D$, which refers to the ratio of the dissociation rate to the association rate (koff/kon). $K_D$ may be determined by using any conventional method known in the art, including but are not limited to surface plasmon resonance (SPR) method, microscale thermophoresis method, and HPLC-MS method. In certain embodiments, the anti-CLDN18.2 antibody or the antigen-binding fragment thereof provided herein binds to a fusion polypeptide comprising first extracellular loop of human CLDN18.2 at a $K_D$ of no more than $10^{-6}$ M (e.g. no more than $10^{-7}$ M, $10^{-7}$ M, 108 M, or $10^{-8}$-5 M), as measured by SPR. The lower the $K_D$ value, the higher the affinity.

In certain embodiments, the anti-CLDN18.2 antibodies and the antigen-binding fragments thereof do not cross-react with human CLDN18.1. An anti-CLDN18.2 antibody that "does not cross-react with" or "has no cross-reactivity with" human CLDN18.1 is an antibody that do not produce undesired results such as false positives in a detection assay (e.g. RIC assay) for human CLDN18.2. In certain embodiments, the binding to human CLDN18.1 is not detectable in the detection assay (e.g. IHC assay, or flow cytometry assay). The level of binding can be determined as the level of antigen-antibody complex that is formed at a given concentration of the antibody and a given concentration of the antigen. In certain embodiments, the anti-CLDN18.2 antibodies and the antigen-binding fragments thereof provided herein bind to human CLDN18.1 at a level or affinity lower than (e.g. at least 10%, 20%, 30%, 40%, 50%, 60%, 70%, 80%, 90% lower than) the binding of antibody GC182 to human CLDN18.1.

In certain embodiments, no more than 5%, 4%, 3%, 2%, 1%, 0.8%, 0.5%, 0.3% or 0.1% of the human CLDN18.1-expressing cells are detected positive in an IHC assay by the anti-CLDN18.2 antibodies and the antigen-binding fragments thereof provided herein. In certain embodiments, the anti-CLDN18.2 antibodies and the antigen-binding fragments thereof provided herein do not show detectable binding to human CLDN18.1 in an IHC assay. In certain embodiments, the anti-CLDN18.2 antibodies and the antigen-binding fragments thereof provided herein do not show detectable binding to human CLDN18.1 in a non-cancerous human lung tissue sample in an IHC assay.

In certain embodiments, the anti-CLDN18.2 antibodies and the antigen-binding fragments thereof provided herein have no cross-reactivity to human CLDN18.1 in a formalin-fixed paraffin-embedded (FFPE) sample at an antibody concentration of 1 nM as measured by ELISA or at an antibody concentration of 0.5 ug/ml as measured by IHC. The IHC can be carried out following the procedures and conditions as outlined in Example 8 or 9.

In certain embodiments, the anti-CLDN18.2 antibodies and the antigen-binding fragments thereof provided herein have no cross-reactivity to non-cancerous cells except stomach epithelial cells. In certain embodiments, the anti-CLDN18.2 antibodies and the antigen-binding fragments thereof provided herein have no cross-reactivity to non-cancerous human tissues such as lung tissue, intestine tissue, kidney tissue, tonsil tissue, thyroid tissue, skeletal muscle tissue, or breast tissue. This distinguishes the antibodies provided herein from existing monoclonal anti-CLDN18.2 antibodies. For example, antibody 43-14A has been shown to bind to human CLDN18.1 and therefore shows cross-reactivity with non-cancerous human lung tissue, see, the IHC result of Ventana's instruction (see Ventana CLDN18 (43-14A) Assay, Ref. 790-7027, 08504148001). For another example, antibody GC182 is also found to be cross-reacting with CLDN18.1, and therefore stains non-cancerous human lung tissue (see Example 4 and FIG. 2 of the present disclosure). For another example, anti-CLDN18.2 antibody EPR19202 (available from Abcam under product name ab222512) has been shown to bind non-specifically to skeletal muscle tissue, and therefore shows cross-reactivity with non-cancerous skeletal muscle tissue.

Illustrative Anti-CLDN18.2 Antibody

In certain embodiments, the present disclosure provides isolated antibodies or antigen binding fragments thereof that specifically bind to CLDN18.2 (e.g. human CLDN18.2), comprising a) a heavy chain CDR1 comprising the amino acid sequence of $X_1X_2YX_3H$ (SEQ ID NO: 8), a heavy chain CDR2 comprising the amino acid sequence of $WIYPX_4GX_5X_6X_7X_8YX_9EKFKG$ (SEQ ID NO: 12), and/or a heavy chain CDR3 comprising the amino acid sequence of $NYX_{10}STFGY$ (SEQ ID NO: 24); and/or b) a light chain CDR1 comprising the amino acid sequence of RSSQNIVHSNGNTYLE (SEQ ID NO: 2), a light chain CDR2 comprising the amino acid sequence of $KX_{11}SNRFS$ (SEQ ID NO: 25), and/or a light chain CDR3 comprising the amino acid sequence of FQGSHVPFT (SEQ ID NO: 6);

wherein $X_1$ is R or T, $X_2$ is N or Y, $X_3$ is F or I, $X_4$ is G or R, $X_5$ is F or G, $X_6$ is D or N, $X_7$ is I or T, $X_8$ is E or V, $X_9$ is S or N, $X_{10}$ is G or R, and $X_{11}$ is V or I.

In certain embodiments, the present disclosure provides isolated antibodies or antigen binding fragments thereof that specifically bind to CLDN18.2 (e.g. human CLDN18.2), comprising one or more (e.g. 1, 2, 3, 4, 5, or 6) CDRs selected from the set of sequences consisting of SEQ ID NOs: 1-6, or selected from the set of sequences consisting of SEQ ID NOs: 2, 6, 7 and 9-11.

In certain embodiments, the anti-CLDN18.2 antibodies and the antigen-binding fragments provided herein comprise a heavy chain CDR3 sequence of SEQ ID NO: 5 or 11. Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81 (1983)). The diversity in the heavy chain CDR3 is sufficient to produce most antibody specificities (Xu J L, Davis M M. Immunity. 13:37-45 (2000)) as well as desirable antigen-binding affinity (Schier R, etc. J Mol Biol. 263:551-67 (1996)).

In certain embodiments, the anti-CLDN18.2 antibodies and the antigen-binding fragments provided herein comprise: a heavy chain CDR1 comprising the amino acid sequence selected from: SEQ ID NO: 1 and SEQ ID NO: 7, and/or a heavy chain CDR2 comprising the amino acid sequence selected from: SEQ ID NO: 3 and SEQ ID NO: 9, and/or a heavy chain CDR3 comprising the amino acid sequence selected from: SEQ ID NO: 5 and SEQ ID NO: 11; and/or a light chain CDR1 comprising the amino acid sequence selected from: SEQ ID NO: 2, and/or a light chain CDR2 comprising the amino acid sequence selected from: SEQ ID NO: 4 and SEQ ID NO: 10, and/or a light chain CDR3 comprising the amino acid sequence selected from: SEQ ID NO: 6.

In another aspect, the present disclosure provides an isolated antibody or an antigen binding fragment thereof that specifically bind to CLDN18.2 (e.g. human CLDN18.2), comprising:

a) a heavy chain CDR1 comprising the amino acid sequence of SEQ ID NO: 1, a heavy chain CDR2 comprising the amino acid sequence of SEQ ID NO: 3, and a heavy chain CDR3 comprising the amino acid sequence of SEQ ID NO: 5; or b) a heavy chain CDR1 comprising SEQ ID NO: 7, a heavy chain CDR2 sequence comprising SEQ ID NO: 9, and a heavy chain CDR3 sequence comprising SEQ ID NO: 11.

In certain embodiments, the antibody or an antigen-binding fragment thereof provided herein comprises:

a) a light chain CDR1 comprising the amino acid sequence of SEQ ID NO: 2, a light chain CDR2 comprising the amino acid sequence of SEQ ID NO: 4, and a light chain CDR3 comprising the amino acid sequence of SEQ ID NO: 6; or b) a light chain CDR1 comprising the amino acid sequence of SEQ ID NO: 2, a light chain CDR2 comprising the amino acid sequence of SEQ ID NO: 10, and a light chain CDR3 comprising the amino acid sequence of SEQ ID NO: 6.

In certain embodiments, the antibody or an antigen-binding fragment thereof provided herein, comprising:

a) a heavy chain CDR1 comprising the amino acid sequence of SEQ ID NO: 1, a heavy chain CDR2 comprising the amino acid sequence of SEQ ID NO: 3, a heavy chain CDR3 comprising the amino acid sequence of SEQ ID NO: 5, a light chain CDR1 comprising the amino acid sequence of SEQ ID NO: 2, a light chain CDR2 comprising the amino acid sequence of SEQ ID NO: 4, and a light chain CDR3 comprising the amino acid sequence of SEQ ID NO: 6; or b) a heavy chain CDR1 comprising the amino acid sequence of SEQ ID NO: 7, a heavy chain CDR2 comprising the amino acid sequence of SEQ ID NO: 9, a heavy chain CDR3 comprising the amino acid sequence of SEQ ID NO: 11, a light chain CDR1 comprising the amino acid sequence of SEQ ID NO: 2, a light chain CDR2 comprising the amino acid sequence of SEQ ID NO: 10, and a light chain CDR3 comprising the amino acid sequence of SEQ ID NO: 6.

CDRs are known to be responsible for antigen binding, however, it has been found that not all of the 6 CDRs are necessarily indispensable or unchangeable. In other words, it is possible to replace or change or modify 1, 2, or 3 CDRs provided above (e.g. corresponding to any one of SEQ ID NOs: 1-6, or SEQ ID NOs: 2, 6, 7 and 9-11), yet substantially retain the specific binding affinity to CLDN18.2. Antibodies having such modified or variant CDRs are also encompassed in the present disclosure.

In certain embodiments, the antibody or an antigen-binding fragment thereof provided herein, comprising:

a) a heavy chain variable region comprising the amino acid sequence of SEQ ID NO: 13, and a light chain variable region comprising the amino acid sequence of SEQ ID NO: 14; or b) a heavy chain variable region comprising the amino acid sequence of SEQ ID NO: 15, and a light chain variable region comprising the amino acid sequence of SEQ ID NO: 16.

Antibody "14G11" as used herein refers to a mouse antibody having a heavy chain variable region of SEQ ID NO: 13, and a light chain variable region of SEQ ID NO: 14.

Antibody "69H2" as used herein refers to a mouse antibody having a heavy chain variable region of SEQ ID NO: 15, and a light chain variable region of SEQ ID NO: 16.

Table 1 shows the CDR sequences of anti-CLDN18.2 antibodies 14G11 and 69H2. The heavy chain and light chain variable region sequences are also provided below in Table 2.

TABLE 1

Sequences of CLDN18.2 antibodies' CDR regions

| Antibody | Region | CDR1 | CDR2 | CDR3 |
|---|---|---|---|---|
| 14G11 | HCDR | SEQ ID NO: 1<br>RNYFH | SEQ ID NO: 3<br>WIYPGGFDIEYSEKFKG | SEQ ID NO: 5<br>NYGSTFGY |
| | LCDR | SEQ ID NO: 2<br>RSSQNIVHSNGNTYLE | SEQ ID NO: 4<br>KVSNRFS | SEQ ID NO: 6<br>FQGSHVPFT |
| 69H2 | HCDR | SEQ ID NO: 7<br>TYYIH | SEQ ID NO: 9<br>WIYPRGGNTVYNEKFK<br>G | SEQ ID NO: 11<br>NYRSTFGY |
| | LCDR | SEQ ID NO: 2<br>RSSQNIVHSNGNTYLE | SEQ ID NO: 10<br>KISNRFS | SEQ ID NO: 6<br>FQGSHVPFT |

TABLE 2

Sequences of mouse/recombinant antibody VH/VL regions

| | VH | VL |
|---|---|---|
| 14G11 | SEQ ID NO: 13<br>QVQLQQSGPELVRPGASVKISCKAS<br>GYRFTRNYFHWVKQRPGQGLEWIG<br>WIYPGGFDIEYSEKFKGKATLTTDTS<br>SSTAYMLLTSLTSEDSAVYYCAINYG<br>STFGYWGQGTLVTVSV | SEQ ID NO: 14<br>DVLMTQTPLSLPVSLGDQASISCRS<br>SQNIVHSNGNTYLEWYLQRPGQSP<br>KLLIYKVSNRFSGVPDRFSGSGSGT<br>DFTLKINRVEAEDLGVYYCFQGSH<br>VPFTFGSGTKLEIK |
| 69H2 | SEQ ID NO: 15<br>QVQLQQSGPELMKPGASLQISCKAS<br>GYFFTTYYIHWVKQRPGQGLEWIG<br>WIYPRGGNTVYNEKFKGKATLTSD<br>TSSSTAYMQLSSLTSEDSAVYYCAIN<br>YRSTFGYWGQGTLVTVSA | SEQ ID NO: 16<br>DVLMTQTPLSLPVSLGDQASISCRS<br>SQNIVHSNGNTYLEWYLQKPGQSP<br>KLLIYKISNRFSGVPDRFSGSGSGT<br>DFTLKISRVEAEDLGVYYCFQGSH<br>VPFTFGSGTKLEIK |

In certain embodiments, the antibodies and antigen-binding fragments thereof provided herein comprise suitable framework region (FR) sequences, as long as the antibodies and antigen-binding fragments thereof can specifically bind to CLDN18.2 (e.g., human CLDN18.2). The CDR sequences provided in Table 1 are obtained from mouse antibodies, but they can be grafted to any suitable FR sequences of any suitable species such as mouse, human, rat, rabbit, among others, using suitable methods known in the art such as recombinant techniques. FR sequences can be readily identified by a skilled person in the art based on the CDR sequences in Table 1 above and variable region sequences in Table 2 above, as it is well-known in the art that a CDR region is flanked by two FR regions in the variable region.

In certain embodiments, the anti-CLDN18.2 antibody or an antigen-binding fragment thereof provided herein, further comprises an immunoglobulin constant region. The constant region optionally comprises a heavy chain constant region of IgG, and/or a light chain constant region. The heavy chain constant region comprises CH1, hinge, and/or CH2-CH3 regions. In certain embodiments, the heavy chain constant region comprises an Fc region. In certain embodiments, the light chain constant region comprises Cκ or Cλ.

In certain embodiments, the anti-CLDN18.2 antibodies and the fragments thereof provided herein further comprise a constant region of mouse IgG1, IgG2, IgG3, or IgG4. In certain embodiments, the anti-CLDN18.2 antibodies and antigen-binding fragments thereof provided herein comprises a constant region of mouse IgG1 isotype. In certain embodiments, the heavy chain constant region of mouse IgG1 comprises SEQ ID NO: 17, or a homologous sequence thereof having at least 80% (e.g. at least 85%, 90%, 95%, 96%, 97%, 98%, or 99%) sequence identity, and/or the light chain constant region of mouse IgG1 comprises an amino acid sequence of SEQ ID NO: 18 or a homologous sequence thereof having at least 80% (e.g. at least 85%, 90%, 95%, 96%, 97%, 98%, or 99%) sequence identity.

The anti-CLDN18.2 antibodies or antigen-binding fragments thereof provided herein can be a monoclonal antibody, a bispecific antibody, a multi-specific antibody, a recombinant antibody, a chimeric antibody, a humanized antibody, a labeled antibody, a bivalent antibody, an anti-idiotypic antibody, a fusion protein, a dimerized or polymerized antibody, or a modified antibody (e.g. glycosylated antibody). A recombinant antibody is an antibody prepared in vitro using recombinant methods rather than in animals.

In certain embodiments, the anti-CLDN18.2 antibodies or antigen-binding fragments thereof provided herein are bivalent, tetravalent, hexavalent, or multivalent. Any molecule being more than bivalent is considered multivalent, encompassing for example, trivalent, tetravalent, hexavalent, and so on.

In some embodiments, the anti-CLDN18.2 antibodies and the antigen-binding fragments provided herein comprise all or a portion of the heavy chain variable domain and/or all or a portion of the light chain variable domain. In one embodiment, the anti-CLDN18.2 antibodies and the antigen-binding fragments provided herein is a single domain antibody which consists of all or a portion of the heavy chain variable domain provided herein. More information of such a single domain antibody is available in the art (see, e.g., U.S. Pat. No. 6,248,516).

Antibody Variants

The anti-CLDN18.2 antibodies and antigen-binding fragments thereof provided herein also encompass various types of variants of the antibodies 14G11 and 69H2.

In certain embodiments, the anti-CLDN18.2 antibody or antigen binding fragments thereof provided herein comprise one or more mutations in one or more of the CDR sequences provided in Table 1 above, one or more of the non-CDR sequences of the heavy chain variable region or light chain variable region provided in Table 2 above, and/or the constant region (e.g. Fc region) sequences as set forth in SEQ ID NOs: 17 or 18, yet retaining binding specificity to CLDN18.2, in particular to human CLDN18.2, or more specifically to an epitope within the amino acid sequence of SEQ ID NO: 19. These are also referred to as variants of antibodies 14G11 and 69H2, or variants of the antigen binding fragments. In certain embodiments, the variants retain binding affinity at a level similar to or even higher than its parent antibody (e.g. antibody 14G11 or 69H2). "Mutations" or "mutated" as used herein include substitutions, insertions, and/or deletions in an amino acid sequence or polynucleotide sequence. In certain embodiments, at least one (or all) of the mutation(s) comprises a conservative substitution.

In certain embodiments, the antibody variants comprise no more than 10, 9, 8, 7, 6, 5, 4, 3, 2, or 1 substitutions in total in the CDR sequences, in the FR sequences, or in the variable region sequences of the antibodies 14G11 and 69H2. In certain embodiments, the antibody variants comprise 1, 2, or 3 CDR sequences having at least 80% (e.g., at least 85%, 88%, 90%, 91%, 92%, 93%, 94%, 95%, 96%, 97%, 98%, 99%) sequence identity to that (or those) listed in Table 1, and in the meantime retain the binding specificity to CLDN18.2, optionally having binding affinity at a level similar to or even higher than its parent antibody (e.g. antibody 14G11 or 69H2).

In certain embodiments, the antibody variants comprise a heavy chain variable region sequence having at least 80% (e.g., at least 85%, 88%, 90%, 91%, 92%, 93%, 94%, 95%, 96%, 97%, 98%, 99%) sequence identity to that (or those) of SEQ ID NOs: 13 or 15, and/or a light chain variable region sequence having at least 80% (e.g., at least 85%, 88%, 90%, 91%, 92%, 93%, 94%, 95%, 96%, 97%, 98%, 99%) sequence identity to that (or those) of SEQ ID NOs: 14 or 16, and in the meantime retain the binding specificity to CLDN18.2, optionally having binding affinity at a level similar to or even higher than its parent antibody (e.g. antibody 14G11 or 69H2). In some embodiments, a total of 1 to 10 amino acid residues have been mutated in a sequence selected from SEQ ID NOs: 13-16. In some embodiments, the mutations occur in regions outside the CDRs (i.e., in the FRs). In some embodiments, one or more of the mutations are conservative substitutions. In some embodiments, all of the mutations are conservative substitutions.

In certain embodiments, the present disclosure provides a variant of antibody 14G11 or 69H2, wherein the variant comprises:

a) a heavy chain CDR1 (HCDR1) sequence having at least 80% (e.g. at least 85%, 88%, 90%, 91%, 92%, 93%, 94%, 95%, 96%, 97%, 98%, 99%) sequence identity to SEQ ID NO: 1 or SEQ ID NO: 7, and/or b) a heavy chain CDR2 (HCDR2) sequence having at least 80% (e.g. at least 85%, 88%, 90%, 91%, 92%, 93%, 94%, 95%, 96%, 97%, 98%, 99%) sequence identity to SEQ ID NO: 3 or SEQ ID NO: 9, and/or c) a heavy chain CDR3 (HCDR3) sequence having at least 80% (e.g. at least 85%, 88%, 90%, 91%, 92%, 93%, 94%, 95%, 96%, 97%, 98%, 99%) sequence identity to SEQ ID NO: 5 or SEQ ID NO: 11, and/or d) a light chain CDR1 (LCDR1) sequence having at least 80% (e.g. at least 85%, 88%, 90%, 91%, 92%, 93%, 94%, 95%, 96%, 97%, 98%, 99%) sequence identity to SEQ ID NO: 2, and/or e) a light chain CDR2 (LCDR2) sequence having at least 80% (e.g. at least 85%, 88%, 90%, 91%, 92%, 93%, 94%, 95%, 96%, 97%, 98%, 99%) sequence identity to SEQ ID NO: 4 or SEQ ID NO: 10, and/or f) a light chain CDR3 (LCDR3) sequence having at least 80% (e.g. at least 85%, 88%, 90%, 91%, 92%, 93%, 94%, 95%, 96%, 97%, 98%, 99%) sequence identity to SEQ ID NO: 6, and in the meantime retain the binding specificity to CLDN18.2, optionally having binding affinity at a level similar to or even higher than its parent antibody (e.g. antibody 14G11 or 69H2).

In certain embodiments, the antibody variants provided herein comprises an HCDR1 having no more than 3, 2, or 1 amino acid mutations in SEQ ID NO: 1 or SEQ ID NO: 7, an HCDR2 having no more than 6, 5, 4, 3, 2, or 1 amino acid mutations in SEQ ID NO: 3 or SEQ ID NO: 9, an HCDR3 having no more than 6, 5, 4, 3, 2, or 1 amino acid mutations in SEQ ID NO: 5 or SEQ ID NO: 11, a LCDR1 having no more than 2 or 1 amino acid mutations in SEQ ID NO: 2, a LCDR2 having no more than 3, 2, or 1 amino acid mutations in SEQ ID NO: 4 or SEQ ID NO: 10, and/or a LCDR3 having no more than 3, 2, or 1 amino acid mutations in SEQ ID NO: 6, and in the meantime retain the binding specificity to CLDN18.2, optionally having binding affinity at a level similar to or even higher than its parent antibody (e.g. antibody 14G11 or 69H2). In some embodiments, one or more of the mutations are conservative substitutions. In some embodiments, all of the mutations are conservative substitutions.

In certain embodiments, the antibody variants provided herein retain specific binding specificity to CLDN18.2 of their parent antibodies, but have one or more desirable properties conferred by the mutation(s). For example, the antibody variants may have improved antigen-binding affinity, improved glycosylation pattern, reduced risk of glycosylation, reduced deamination, reduced or depleted effector function(s), improved FcRn receptor binding in a pH dependent manner, increased pharmacokinetic half-life, pH sensitivity, and/or compatibility to conjugation (e.g., one or more introduced cysteine residues), to name a few. Such variants are also known as affinity variants, glycosylation variants, cysteine variants, Fc variants, and so on, which are described in more details as follows.

a) Affinity Variant

Affinity variant may contain modifications or substitutions in one or more CDR sequences as provided in Table 1 above, one or more framework (FR) sequences provided herein, or the heavy or light chain variable region sequences provided in Table 2 above.

An affinity variant retain specific binding affinity to CLDN18.2 of the parent antibody, or even have improved CLDN18.2 specific binding affinity over the parent antibody. Various methods known in the art can be used to achieve this purpose. For example, a library of antibody variants (such as Fab or scFv variants) can be generated and expressed with phage display technology, and then screened for the binding affinity to human CLDN18.2. For another example, computer software can be used to virtually simulate the binding of the antibodies to human CLDN18.2, and identify the amino acid residues on the antibodies which form the binding interface. Such residues may be either avoided in the mutation so as to prevent reduction in binding affinity, or targeted for mutation to provide for a stronger binding.

b) Glycosylation Variant

The anti-CLDN18.2 antibodies and antigen-binding fragments provided herein also encompass a glycosylation variant, which can be obtained to either increase or decrease the extent of glycosylation of the antibody or antigen binding fragment thereof.

The antibody or antigen binding fragment thereof may comprise one or more modifications that introduces or removes a glycosylation site. A glycosylation site is an amino acid residue with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

In certain embodiments, the anti-CLDN18.2 antibodies and antigen-binding fragments provided herein comprise a mutation at N297 (e.g. N297A, N297Q, or N297G) to remove the glycosylation site.

c) Cysteine-Engineered Variant

The anti-CLDN18.2 antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibodies or antigen-binding fragments thereof to introduce free cysteine residues are known in the art, see, for example, WO2006/034488.

d) Fc Variant

The anti-CLDN18.2 antibodies and antigen-binding fragments provided herein also encompass an Fe variant, which comprises one or more amino acid residue modifications or substitutions at its Fc region and/or hinge region, for example, to provide for altered effector functions such as ADCC (Antibody-dependent cellular cytotoxicity), ADCP (Antibody-dependent cellular phagocytosis) and CDC (Complement Dependent Cytotoxicity). Examples of Fc variants are known in the art, see, for example, Wang et al., Protein Cell 2018, 9(1): 63-73 and Kang et al., Exp & Mol., Med. (2019) 51:138, which are incorporated herein to their entirety.

Antigen-Binding Fragments

Provided herein are also anti-CLDN18.2 antigen-binding fragments. In some embodiments, the antibodies and antigen-binding fragments provided herein comprise all or a portion of the heavy chain variable domain and/or all or a portion of the light chain variable domain. Various types of antigen-binding fragments are known in the art and can be developed based on the anti-CLDN18.2 antibodies provided herein, including for example, the exemplary antibodies whose CDR sequences are shown in Tables 1, and their different variants (such as affinity variants, glycosylation variants, Fc variants, cysteine-engineered variants and so on).

In certain embodiments, an anti-CLDN18.2 antigen-binding fragment provided herein is a diabody, a Fab, a Fab', a F(ab')2, a Fd, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a NANOBODY®, a domain antibody, or a bivalent domain antibody.

Various techniques can be used for the production of such antigen-binding fragments. Illustrative methods include, enzymatic digestion of intact antibodies (see, e.g., Morimoto et al., Journal of Biochemical and Biophysical Methods 24:107-117 (1992); and Brennan et al., Science, 229:81 (1985)), recombinant expression by host cells such as *E. Coli* (e.g., for Fab, Fv and ScFv antibody fragments), screening from a phage display library as discussed above (e.g., for ScFv), and chemical coupling of two Fab'-SH fragments to form $F(ab')_2$ fragments (Carter et al., Bio/Technology 10:163-167 (1992)). Other techniques for the production of antibody fragments will be apparent to a skilled practitioner.

Epitope

In certain embodiments, the anti-CLDN18.2 antibody or an antigen-binding fragment thereof provided herein binds to an epitope within the amino acid sequence of DQWSTQDLYN (SEQ ID NO: 19).

The term "epitope" as used herein refers to the specific group of atoms or amino acids on an antigen to which an antibody binds. An epitope can be a conformational epitope or a linear epitope. In certain embodiments of the present disclosure, the epitopes bound by the anti-CLDN18.2 antibodies provided herein is linear. Those skilled in the art will recognize that it is possible to determine, without undue experimentation, if an antibody binds to the same or overlapping or adjacent epitope as the antibody of present disclosure (e.g., hybridoma/mouse antibodies 14G11 and 69H2) by ascertaining whether the two competes for binding to a CLDN18.2 antigen polypeptide.

The present disclosure provides monoclonal antibodies directed against a certain epitope located within the N-terminal portion of CLDN18.2, which are useful in detecting and identifying cells expressing CLDN18.2, without cross-reacting to CLDN18.1. According to the sequences of human CLDN18.1 and CLDN18.2, there are 8 different amino acids located between amino acid 28-70 (i.e. N-terminal portion which comprises the first transmembrane (TM) region and loop 1), whereas the C-terminal sequences of human CLDN18.1 and CLDN18.2 are identical. A linear epitope located in the N-terminal of human CLDN18.2 (amino acids 28-37 in the first extracellular domain, i.e. SEQ ID NO: 19) has been reported by Sahin U et al. (see Sahin Ugur et al, Clin Cancer Res 2008; 14(23) Dec. 1, 2008). However, to date, no monoclonal antibodies directed to such peptide fragment has been reported, and to the knowledge of the inventors, the present disclosure for the first time provides monoclonal antibodies that bind to the peptide fragment of SEQ ID NO: 19.

In another aspect, the present disclosure provides monoclonal antibodies or antigen-binding fragments thereof, which competes for binding to CLDN18.2 with the antibody or antigen-binding fragment thereof provided herein, such as 14G11 and 69H2.

The term "compete for binding" as used herein with respect to two antigen-binding proteins (e.g. antibodies), means that one antigen-binding protein blocks or reduces binding of the other to the antigen (e.g., human CLDN18.2) to any detectable degree, as determined by a competitive binding assay. Competitive binding assays are well known in the art, include, for example, direct or indirect radioimmunoassay (RIA), direct or indirect enzyme immunoassay (EIA), and sandwich competition assay (see, e.g., Stahli et al., 1983*, Methods in Enzymology* 9:242-253). Typically, such an assay involves the use of purified antigen bound to a solid surface or cells bearing the antigen, an unlabelled test antibody and a labeled reference antibody. Competitive inhibition is measured by determining the amount of label bound to the solid surface or cells in the presence of the test antibody. Usually the test antibody is present in excess. If two antibodies competes for binding to the CLDN18.2, then the two antibodies bind to the same or overlapping epitope, or an adjacent epitope sufficiently proximal to the epitope bound by the other antibody for steric hindrance to occur. Usually, when a competing antibody is present in excess, it will inhibit (e.g., reduce) specific binding of a test antibody to a common antigen by at least 50-55%, 55-60%, 60-65%, 65-70%, 70-75% 75-80%, 80-85%, 85-90% or more.

Polynucleotides and Recombinant Methods

The present disclosure provides isolated polynucleotides that encode the anti-CLDN18.2 antibodies and antigen-binding fragments thereof. The term "nucleic acid" or "polynucleotide" as used herein refers to deoxyribonucleic acids (DNA) or ribonucleic acids (RNA) and polymers thereof in either single- or double-stranded form. Unless otherwise indicated, a particular polynucleotide sequence also implicitly encompasses conservatively modified variants thereof (e.g. degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

DNA encoding the monoclonal antibody is readily isolated and sequenced using conventional procedures (e.g. by using oligonucleotide probes that are capable of binding specifically to genes encoding the heavy and light chains of the antibody). The encoding DNA may also be obtained by synthetic methods.

The present disclosure provides vectors (e.g. expression vectors) comprising the isolated polynucleotide provided herein. A vector may be used to transform, transduce, or transfect a host cell so as to bring about expression of the genetic element it carries within the host cell. Examples of vectors include plasmids, phagemids, cosmids, and artificial chromosomes such as yeast artificial chromosome (YAC), bacterial artificial chromosome (BAC), or P1-derived artificial chromosome (PAC), bacteriophages such as lambda phage or M13 phage, and animal viruses. A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector.

In certain embodiments, the vectors provided herein are expression vectors. In certain embodiments, an expression vector provided herein comprises the polynucleotide encoding the antibodies or antigen-binding fragments thereof provided herein, at least one promoter (e.g. SV40, CMV, EF-1α) operably linked to the polynucleotide sequence, and at least one selection marker.

Examples of vectors include, but are not limited to, retrovirus (including lentivirus), adenovirus, adeno-associated virus, herpesvirus (e.g. herpes simplex virus), poxvirus, baculovirus, papillomavirus, papovavirus (e.g. SV40), lambda phage, and M13 phage, plasmids such as pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment thereof can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g. *E. coli, Enterobacter, Erwinia, Klebsiella, Proteus, Salmonella*, e.g. *Salmonella typhimurium, Serratia*, e.g. *Serratia marcescans*, and *Shigella*, as well as Bacilli such as *B. subtilis* and *B. licheniformis, Pseudomonas* such as *P. aeruginosa*, and *Streptomyces.*

In addition to prokaryotes, eukaryotic microbes such as filamentous fungi or yeast are suitable cloning or expression hosts for anti-CLDN18.2 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g. *K. lactis, K. fragilis* (ATCC 12,424), *K. bulgaricus* (ATCC 16,045), K. wickeramii (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g. *Neurospora, Penicillium, Tolypocladium*, and *Aspergillus* hosts such as *A. nidulans* and *A. niger.*

Suitable host cells for the expression of glycosylated antibodies or antigen-fragment provided herein are derived from multicellular organisms such as invertebrate cells, for example plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, *Mather, Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some preferable embodiments, the host cell is a mammalian cultured cell line, such as CHO, BHK, NSO, 293 and their derivatives.

Host cells are transformed with the above-described expression or cloning vectors for anti-CLDN18.2 antibody production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E.*

*coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-CLDN18.2 antibodies and antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., J. Immunol. Meth. 62:1-13 (1983)). Protein G is recommended for all mouse isotypes and for human gamma3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

The present disclosure provides methods of expressing the anti-CLDN18.2 antibody or antigen-binding fragment thereof provided herein, comprising culturing the host cell provided herein under the condition at which the vector provided herein is expressed.

Conjugates

In some embodiments, the anti-CLDN18.2 antibodies or antigen-binding fragments thereof is linked or conjugated to one or more moieties. Examples of such moieties include but are not limited to, therapeutic agent (e.g. a DNA-alkylator, a topoisomerase inhibitor, a tubulin-binder, or other anticancer drugs), a detectable label, a pharmacokinetic modifying moiety (e.g. a polymer such as PEG which extends half-life), or a purifying moiety (e.g. a magnetic bead or a nanoparticle).

A moiety can be attached to the antibodies or antigen-binding fragments thereof either directly or via a linker or through another moiety, for example, by covalent binding, affinity binding, intercalation, coordinate binding, complexation, association, blending, or addition, among other methods. In certain embodiments, the antibodies or antigen binding fragments thereof are linked to one or more moieties via a linker. In certain embodiments, the linker is a hydrazone linker, a disulfide linker, a bifunctional linker, dipeptide linker, glucuronide linker, or a thioether linker.

In certain embodiments, the antibodies or antigen-binding fragments thereof provided herein may be engineered to contain specific sites outside the epitope binding portion that may be utilized for linking to one or more moieties. For example, such a site may include one or more reactive amino acid residues, such as for example cysteine or histidine residues, to facilitate covalent linkage to a moiety.

In some embodiments, the anti-CLDN18.2 antibodies or antigen-binding fragments thereof are linked to one or more moieties that function to (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation.

Such moieties include, but are not limited to, labels or moieties that are directly detectable (such as radioactive isotope, a lanthanide, a chemiluminescent label, a chromophoric moiety, an enzyme label, colloidal gold particles and a fluorescent label) via imaging, an enzymatic reaction and so on, as well as moieties that are indirectly detectable, for example, through an molecular interaction. Examples of indirectly detectable label include, biotin/avidin, biotin/streptavidin, a digoxigenin label, a hapten, a DNA molecule for detection and particle labels (paramagnetic particle, metal particle labels, magnetic particle labels, and polymer particle labels, etc).

Examples of radioactive isotopes include such as S, C, I, H, and I. The antibody can be labeled with the radioisotope using the techniques described in Current Protocols in Immunology, Volumes 1 and 2, Coligen et al, Ed. Wiley-Interscience, New York, N.Y., Pubs. (1991) for example, and radioactivity can be measured using scintillation counting. Other radionuclides include $^{123}$I, $^{124}$I, $^{125}$I, $^{131}$I, $^{35}$S, $^{3}$H, $^{99}$Tc, $^{90}$Y, $^{111}$In, $^{112}$In, $^{32}$P, $^{14}$C, $^{15}$O, $^{13}$N, $^{18}$F, $^{86}$Y, $^{88}$Y, $^{90}$Y, $^{51}$Cr, $^{57}$To, $^{225}$Ra, $^{60}$Co, $^{59}$Fe, $^{57}$Se, $^{52}$Eu, $^{64}$Cu, $^{67}$Cu, $^{217}$Ci, $^{177}$Lu, $^{211}$At, $^{186}$Re, $^{188}$Re, $^{153}$Sm, $^{212}$Bi, $^{212}$Pb, $^{47}$Sc, $^{109}$Pd, $^{234}$Th, $^{40}$K, $^{57}$Gd, $^{55}$Mn, $^{52}$Tr, and $^{56}$Fe.

Fluorescent or luminescent labels include, but not limited to, rare earth chelates (europium chelates), fluorescein and its derivatives, rhodamine and its derivatives, isothiocyanate, phycoerythrin, phycocyanin, allophycocyanin, o-phthaladehyde, fluorescamine, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, Texas Red, dansyl, Lissamine, umbelliferone, phycocrytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in, for example, Current Protocols in Immunology, supra, for example. Fluorescence can be quantified using a fluorimeter.

Another type of useful label is enzyme-substrate label. Various enzyme-substrate labels are available (see U.S. Pat. No. 4,275,149). The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor.

Numerous enzyme-substrate combinations are available to those skilled in the art (see U.S. Pat. Nos. 4,275,149 and 4,318,980), such as: (i) Horseradish peroxidase (HRP) with hydrogen peroxidase as a substrate, wherein the hydrogen peroxidase oxidizes a dye precursor, such as, e.g., 3,3' diamino benzidine (DAB), which produces a brown end product; 3-amino-9-ethylcarbazole (AEC), which upon oxidation forms a rose-red end product; 4-chloro-l-napthol (CN), which precipitates as a blue end product; and p-Phenylenediamine dihydrochloride/pyrocatecol, which generates a blue-black product; orthophenylene diamine (OPD) and 3,3',5,5'-tetramethyl benzidine hydrochloride (TMB); (ii) alkaline phosphatase (AP) and para-Nitrophenyl phosphate, naphthol AS-MX phosphate, Fast Red TR and Fast Blue BB, napthol AS-BI phosphate, napthol AS-TR phosphate, 5-bromo-4-chloro-3-indoxyl phosphate (BCIP), Fast Red LB, Fast Garnet GBC, Nitro Blue Tetrazolium (NBT), and iodonitrotetrazolium violet (INT); and (iii) β-D-galactosidase (β-D-Gal) with a chromogenic substrate (e.g., p-nitrophenyl-P-D-galactosidase) or fluorogenic substrate (e.g., 4-methylumbelliferyl-P-D-galactosidase).

Other useful enzymatic labels include luciferases (e.g. firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, Methods for the Preparation of Enzyme-Antibody Conjugates for use in Enzyme Immunoassay, in Methods in Enzym. (ed J. Langbne & H. Van Vunakis), Academic press, New York, 73:147-166 (1981).

Detection of CLDN18.2 and Methods of Use

The present disclosure provide methods of detecting presence or expression level of CLDN18.2 in a sample, comprising contacting the sample with the antibody or antigen-binding fragment thereof provided herein, under condition that allow specific binding of the antibody or antigen-binding fragment thereof to CLDN18.2 (e.g. human CLDN18.2), and determining the presence or expression level of CLDN18.2 in the sample.

In another aspect, methods are provided for diagnosing a CLDN18.2-associated disease or condition (e.g. cancer) in a subject, comprising:

a) contacting a sample obtained from the subject with the antibody or antigen-binding fragment thereof provided herein under conditions that allow specific binding of the antibody or antigen-binding fragment thereof to CLDN18.2; and b) determining presence or expression level of CLDN18.2 in the sample;

wherein the subject is diagnosed as having a CLDN18.2-associated disease or condition (e.g. cancer) when the presence of CLDN18.2 is found or when the expression level of CLDN18.2 reaches a threshold level. In certain embodiments, the sample is not a stomach epithelial tissue.

In another aspect, methods are provided for determining the eligibility of a subject having or at risk for a CLDN18.2-associated disease or condition for treatment with a CLDN18.2-targeting agent, comprising:

a) contacting a sample obtained from the subject with the antibody or antigen-binding fragment thereof provided herein under conditions that allow specific binding of the antibody or antigen-binding fragment thereof to CLDN18.2; and b) determining presence or expression level of CLDN18.2 in the sample;

wherein the subject is determined as eligible for treatment with a CLDN18.2-targeting agent when the presence of CLDN18.2 is found or when the expression level of CLDN18.2 reaches a threshold level, or wherein the subject is determined as not eligible for treatment with a CLDN18.2-targeting agent when the presence of CLDN18.2 is not found or when the expression level of CLDN18.2 is below a threshold level.

In another aspect, methods are provided for predicting therapeutic effectiveness of a CLDN18.2-targeting agent in treating a CLDN18.2-associated disease or condition in a subject, comprising:

a) contacting a sample obtained from the subject with the antibody or antigen-binding fragment thereof provided herein under condition that allow specific binding of the antibody or antigen-binding fragment thereof to CLDN18.2;

b) determining presence or expression level of human CLDN18.2 in the sample; and c) predicting the therapeutic effectiveness of the CLDN18.2-targeting agent, wherein the CLDN18.2-targeting agent is predicted to be effective in treating the subject when the presence of CLDN18.2 is found or when the expression level of CLDN18.2 reaches a threshold level, or wherein the CLDN18.2-targeting agent is predicted to be not effective in treating the subject when the presence of CLDN18.2 is not found or when the expression level of CLDN18.2 is below the threshold level.

In yet another aspect, methods are provided for treating a subject having or at risk for a CLDN18.2-associated disease or condition, comprising:

a) selecting a subject that is suitable for the treatment, comprising:

i) contacting a sample obtained from the subject with the antibody or antigen-binding fragment thereof provided herein under condition that allow specific binding of the antibody or antigen-binding fragment thereof to CLDN18.2;

ii) determining the presence or expression level of human CLDN18.2 in the sample; and iii) selecting the subject as suitable for the treatment with the CLDN18.2-targeting agent when the presence of CLDN18.2 is found or when the expression level of CLDN18.2 in the sample reaches a threshold level; and b) administering a therapeutically effective amount of CLDN18.2-targeting agent to the selected subject.

In yet another aspect, methods are provided for treating a subject having or at risk of cancer, comprising:

a) selecting a subject comprising:
   i) contacting a sample obtained from the subject with the antibody or antigen-binding fragment thereof provided herein under condition that allow specific binding of the antibody or antigen-binding fragment thereof to CLDN18.2;
   ii) determining the presence or expression level of CLDN18.2 in the sample; and
   iii) selecting the subject as not suitable for the treatment with a CLDN18.2-targeting agent when the presence of CLDN18.2 is not found or when the expression level of CLDN18.2 in the sample is below a threshold level; and
b) administering to the selected subject a Standard-of-Care Therapeutic other than a CLDN18.2-targeting agent.

According to the invention, a "sample" may be any sample useful according to the present disclosure, in particular a biological sample such a tissue sample, including body fluids, and/or a cellular sample and may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid and peptide/protein isolates.

Any biological sample suspected of containing CLDN18.2 can be detected in the methods provided herein. In some embodiments, a suitable sample can be a cell sample or a tissue sample obtained from a subject in need of the detection. For example, the sample may include, normal and cancerous tissue of stomach, lung, breast, colon, kidney, bone, brain, muscle, pancreas, bladder, ovary, uterus, as well as heart, embryonic, or placental tissue. Preferably a sample contains cells or tissue of the organ which is to be examined, e.g. which is to be diagnosed for cancer. For example, if the cancer to be diagnosed is gastric cancer a sample may contain cells or tissue obtained from stomach. In some embodiments, the sample is a tumor sample. In certain embodiments, the tissue samples are samples with CLDN18.2-associated disease or condition.

A suitable sample may be a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells. The term "primary tumor" refers to a tumor growing at the site of the cancer origin. The term "metastatic tumor" refers to a secondary tumor growing at the site different from the site of the cancer origin.

The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments the sample is obtained from in vitro tissue or cell culture.

Examples of the samples herein include, but are not limited to, tumor biopsies, circulating tumor cells, serum or plasma, ascetic fluid, primary cell cultures or cell lines derived from tumors or exhibiting tumor-like properties, as well as preserved tumor samples, such as formalin-fixed, paraffin-embedded (FFPE) tumor samples or frozen tumor samples.

In certain embodiments, the cell sample is produced from a cell block. A "cell block" is a method of preparing cytologic material so that it can be processed, sectioned, stained, and viewed as a histology section. It can provide diagnostic information in addition to that obtained from cytology slides. In certain embodiments, cell blocks can be prepared from residual effusions, sputum, urine sediments, gastrointestinal fluids, cell scraping, or fine needle aspirates. Cells are concentrated or packed by centrifugation or membrane filtration.

A number of methods for cell block preparation have been developed. Representative procedures include the fixed sediment, bacterial agar, or membrane filtration methods. In the fixed sediment method, the cell sediment is mixed with a fixative like Bouins, picric acid, or buffered formalin and then the mixture is centrifuged to pellet the fixed cells. The pellet is collected and placed in a tissue cassette which is placed in a jar with additional fixative and processed as a tissue sample. Agar method is very similar but the pellet is cut in half and the cut side is placed in a drop of melted agar on a glass slide. The agar is allowed to harden and then any excess agar is trimmed away. Alternatively, the pellet may be directly suspended in 2% liquid agar at 65° C. and the sample centrifuged. The agar cell pellet is allowed to solidify for an hour at 4° C. The solid agar may be removed from the centrifuge tube and sliced in half. This is placed in a tissue cassette and the tissue process completed. Centrifugation can be replaced in any these procedures with membrane filtration. Any of these processes may be used to generate a "cell block sample".

In certain embodiments, cell blocks can be prepared using specialized resin including Lowicryl resins, LR White, LR Gold, Unicryl, and MonoStep. These resins have low viscosity and can be polymerized at low temperatures and with ultra violet (UV) light. The embedding process relies on progressively cooling the sample during dehydration, transferring the sample to the resin, and polymerizing a block at the final low temperature at the appropriate UV wavelength.

Cell block sections can be stained with hematoxylin-eosin, Hoechst stain or DAPI for cytomorphological examination, while additional sections are used for examination for CLDN18.2 by exposing to an anti-CLDN18.2 antibody (i.e. primary antibody) for a sufficient period of time and under suitable conditions to allow the antibody to bind to the CLDN18.2 protein in the cell block sections. Unbound and excess amounts of the primary antibody may be washed and removed.

In some embodiments the sample can contain for example, preservatives, anticoagulants, buffers, nutrients, antibiotics, or the like. In certain embodiments the sample has been exposed to and/or contains one or more fixatives. Exemplary fixatives suitable for the methods provided herein include formalin, glutaraldehyde, osmium tetraoxide, acetic acid, ethanol, acetone, picric acid, chloroform, potassium dichromate and mercuric chloride and/or stabilizing by microwave heating or freezing.

In some embodiments, the sample comprises a fixed tissue sample. In some embodiments, the fixed tissue sample is a formalin-fixed paraffin-embedded (FFPE) tissue. FFPE tissue sections can be of about 3-4 millimeters, and preferably 4-40 micrometers, which are mounted and dried on a microscope slide. Examples of paraffin include, but are not limited to, Paraplast, Broloid and Tissuemay. For a fixed tissue sample such as an FFPE tissue sample, the sample may be deparaffinized before contacting with the anti-CLDN18.2 antibody or antigen-binding fragment thereof provided herein.

In some embodiments, the deparaffinized sample may be further treated to allow antigen retrieval. Antigen retrieval refers to any technique in which the masking of an epitope is reversed and epitope-antibody binding is restored. While fixation is essential for the preservation of tissue morphology, this process can also have a negative impact on antibody binding and detection. Fixation can alter protein biochemistry such that the epitope of interest is masked and can no longer bind to the antibody. Masking of the epitope can be caused by cross-linking of amino acids within the epitope, cross-linking unrelated peptides at or near an epitope, altering the conformation of an epitope, or altering the electrostatic charge of the antigen. The need for antigen retrieval depends on multiple variables, including but not limited to, the target antigen, the antibody used, the type of tissue, and the method and duration of fixation. Techniques of antigen retrieval generally include protease-induced epitope retrieval (PIER, by using enzymes such as Proteinase K, Trypsin, and/or Pepsin) and heat-induced epitope retrieval (HIER, by using microwave ovens, pressure cookers, vegetable steamers, autoclaves, or water baths).

In certain embodiments, the presence or expression level of cell surface or membrane-bound CLDN18.2 is detected or determined in the methods provided herein. The phrase "cell surface or membrane-bound CLDN18.2" means that CLDN18.2 is associated with and located at the plasma membrane of a cell, wherein at least a part of the CLDN18.2 is exposed to the extracellular space of said cell and is accessible from the outside of said cell, e.g., by antibodies outside the cell. In certain embodiments, the part of the CLDN18.2 that is exposed extracellularly comprises at least 4, at least 8, at least 10, at least 12, or at least 20 amino acid residues. In normal tissues except stomach epithelial cells, CLDN18.2 are located within the tight junctions of epithelia and endothelia, and are believed to be not accessible to antibodies from outside the cells, and thus considered not cell surface or membrane-bound CLDN18.2.

The presence or expression level of CLDN18.2 protein in a sample can be determined based on the presence or level of the complex of the CLDN18.2 antigen bound by the antibody or the antigen binding fragment thereof disclosed herein. Any suitable methods can be used for detection of the antibody-antigen complex, for example, by immunoassays such as immunohistochemistry (IHC), Immunocytochemistry (ICC), immunofluorescence (IF), immunoblotting (e.g., Western blotting), flow cytometry (e.g., FACS™), Enzyme-linked Immunosorbant Assay (ELISA), enzyme immunoassay (EIA), and radioimmunoassay (RIA). For a review of immunological and immunoassay procedures, see Basic and Clinical Immunology (Stites & Terr eds., 7$^{th}$ ed. 1991). Moreover, the immunoassays can be performed in any of several configurations, which are reviewed extensively in Enzyme Immunoassay (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Terr, eds., 7$^{th}$ ed. 1991).

In certain embodiments, the antibodies or the antigen binding fragments thereof disclosed herein are detectably labeled (e.g. primary antibody), or are not labeled but can react with a second molecule which is detectably labeled (e.g. a detectably labeled secondary antibody).

In certain embodiments, the presence or expression level of CLDN18.2 protein in a sample is determined in accordance to IHC or ICC. IHC refers to the process of detecting antigens (e.g., proteins) in cells of a tissue section, e.g. cells of the tissues mentioned herein. Immunohistochemical staining is widely used in the diagnosis of abnormal cells such as those found in cancerous tumors. In some embodiments, the anti-CLDN18.2 antibodies or the antigen binding fragments thereof disclosed herein can be used as the primary antibody in the IHC or ICC. In general, IHC or ICC can carried out for direct detection or indirect detection of the CLDN18.2 protein (e.g. human CLDN18.2 protein) in the sample, and CLDN18.2 expression can be evaluated using appropriate imaging apparatus.

To allow direct detection of the antigen (e.g. CLDN18.2), one can use the anti-CLDN18.2 antibodies or the antigen binding fragments thereof disclosed herein that are linked to a detectable label, which allows direct visualization without the need of further antibody interaction.

For indirect detection of the antigen (e.g. CLDN18.2), one can use the anti-CLDN18.2 antibodies or the antigen binding fragments thereof disclosed herein which are not labeled but can react with a second molecule which is detectably labeled (e.g. a detectably labeled secondary antibody). For example, the anti-CLDN18.2 antibodies or the antigen binding fragments thereof disclosed herein may be unlabeled, and further contacted with a secondary antibody (e.g. anti-isotypic antibodies) conjugated with a detectable label, to allow indirect detection of the antigen. For another example, the anti-CLDN18.2 antibody provided herein can be conjugated with biotin, which can react with detectably labeled avidin, or vice versa. Biotin binds selectively to avidin, and therefore permits indirect detection of the antibody-antigen complex. In yet another example, the anti-CLDN18.2 antibody provided herein can be conjugated with a small hapten, which can react with an anti-hapten antibody linked to detectable labels as described herein. Exemplary types of labels are described herein above, and any suitable detectable labels can be used.

The ICC or IHC assay may be performed using an automated pathology system, which may include automated staining (conventional stains, histochemical techniques, immunostainers); automated in situ hybridization systems; automatic slide preparation (coverslip, slide drying) and integrated slide and cassette labeling, as described in Roja et al., Review of imaging solutions for integrated, quantitative immunohistochemistry in the Pathology daily practice, Folia Histochemica et Cytobiologica, Vol. 47, No. 3, 349-354, 2009.

An exemplary IHC assay may employ the commercially available Dako EnVision™ FLEX detection system, which is intended for use together with a Dako Autostainer instrument (Dako, an Agilent Technologies Company, Glostrup, Denmark). These reagents can be used off the shelf for other autostainers or for manually-performed staining without using an autostainer.

After completing the staining process, the sample (e.g. a slide) is analyzed for CLDN18.2 staining, either by a human, e.g., a pathologist, or by a computer programmed to distinguish between specific and non-specific staining results. The analysis may be performed directly by viewing the sample through a microscope at low, medium (10-20×) and high power (40-60×), or by viewing high resolution images of the slide taken at low, medium and high power.

The presence of CLDN18.2 expression in the sample can be confirmed by presence of positively-stained cell, for example, a cell having at least partial membrane staining of any intensity for the anti-CLDN18.2 antibody staining. In certain embodiments, a normal sample can be used as a control sample, and the presence of CLDN18.2 expression in the test sample can be determined relative to the control sample. The term "normal" such as used in the term "normal sample" or "normal tissue" refers to a sample or a tissue from a healthy or non-cancerous subject, or a sample or tissue from a healthy or non-cancerous tissue. Preferably, the test and control samples are comparable in terms of type of sample, for example, both are fixed tissue sample. If the test sample shows an increase in staining intensity or in number of positive stained cells than the control sample, then the test sample can be determined as positive for CLDN18.2 expression.

In certain embodiments, the expression level of CLDN18.2 can be quantified using any suitable methods known in the art, for example, by determination of the relative proportion of positively-stained cells and the staining intensity on the cell membrane.

In certain embodiments, the CLDN18.2 expression level is quantified based on the percentage of positively-stained cells (i.e. CLDN18.2-positive cells) in the sample. A CLDN18.2-positive cell is cell having at least partial membrane staining of any intensity for the anti-CLDN18.2 antibody staining. For example, to assess CLDN18.2 expression in a sample, an observer can examine the number of membrane CLDN18.2+ cells in one or more selected field(s) under a microscope and calculate or estimate the percentage of cells that are positive for CLDN18.2. If the sample is highly heterogeneous, then the sample can be divided into zones, and each zone is scored separately and then combined into a single set of percentage values.

In certain embodiments, the expression level is quantified based on staining intensity for CLDN18.2 (e.g. membrane-bound CLDN18.2) in the sample. For example, an intensity score such as 4-point HSCORE can be calculated based on intensity of staining ranging from 0 (no staining), 1+ (weak staining), 2+ (distinct staining), 3+ (strong staining) and 4+ (extremely strong/saturated signal) and multiplying by the percent of cells staining at each intensity (0 to 100%) (see details in, McCarty, K. S. Jr, et al, Cancer Res. 46(suppl 8):4244s-4248s (1986)). For another example, Alfred score can be calculated based on a Total Score (TS, range 0 to 8) by adding together a proportion score (PS) and an intensity score (IS). PS is the proportion of positive tumor cells ranging from 0 to 5 (0=no positive cells, 1=1/100 cells are positive, 2=1/10 cells are positive, 3=1/3 cells are positive, 4=2/3 of cells are positive, 5=all tumor cells are positive). IS means the average staining intensity of positive tumor cells ranging from 0 to 3 (0=negative, 1=weak, 2=intermediate staining, 3=strong staining) (see, details in, Alfred D C et al. Mod Pathol. 11: 155-168 (1998)).

In certain embodiments, the samples are assessed by two observers operating independently and the percentage or the scores are subsequently consolidated. In certain other embodiments, the identification of positive and negative cells is performed or scored using appropriate software.

In certain embodiments, the level of the CLDN18.2 can be determined, for example, by normalizing to a control value or to a standard curve. The control value can be predetermined, or determined concurrently, from a negative control sample or a blank control sample.

In certain embodiments, for the diagnostic or clinical applications, the expression level of CLDN18.2 (e.g. exposed on the cell surface) in the test sample is compared to a threshold level.

A "threshold level" or "threshold value" with respect to CLDN18.2 expression, refers to a level of expression that allows for distinguish of being positive from being negative for cell surface CLDN18.2 expression, or a level of expression that allows for ruling in or ruling out of a CLDN18.2-associated condition, for example, cancer, or the onset or risk to the onset of cancer in a subject, or a threshold level which allows for monitoring treatment response in a subject who is receiving treatment of cancer. In certain embodiments, the threshold is determined relative to a control expression level.

For example, the threshold can be a level above which the sample is scored as having positive expression of CLDN18.2, and hence eligibility for treatment with a CLDN18.2-targeting agent. If the level of CLDN18.2 in the sample reaches or is above the threshold, it could indicate presence of the CLDN18.2-associated disease or condition, and/or likelihood of responding to a CLDN18.2-targeting agent.

The threshold level can be determined by a skilled person in the art, taking consideration of a variety of factors, including for example, the type of sample, the detection method, the disease or condition to be diagnosed, and/or the CLDN18.2-targeting agents to be used.

In certain embodiments, the presence of CLDN18.2 or CLDN18.2-expressing cells and/or a quantity of CLDN18.2 or CLDN18.2-expressing cells which is increased compared to a threshold level, e.g. compared to a subject without a CLDN18.2-associated condition (e.g. a non-cancerous subject), indicates the presence of or risk for (i.e. a potential for a development of) CLDN18.2-associated disease or condition (e.g. a cancer disease) in the patient.

In certain embodiments, the threshold level is a percentage of CLDN18.2 positive cells (%) that have at least partial membrane staining of any intensity. In one embodiment, the threshold level of percentage of CLDN18.2 positive cells (%) is 1%, 2%, 5%, 10%, 15%, 20%, 25%, 30%, 35%, 40%, 45%, 50%, 55%, 60%, 65%, or 70%.

In certain embodiments, the sample is from a subject having, or at risk of, a CLDN18.2-associated disease or condition. The term "CLDN18.2-associated disease or condition" as used herein refers a disease or condition characterized in having an increased expression of CLDN18.2 in cells of a diseased tissue or organ compared to the state in a healthy or noncancerous tissue or organ other than stomach. An increase can be for example an increase by at least 10%, 20%, 30%, 40%, 50%, 100%, 200%, 300%, 400%, 500%, or even more. In certain embodiments, the expression of CLDN18.2 in cells of a diseased tissue or organ is above the detection limit and/or is high enough to allow binding by CLDN18.2-specific antibodies added to the cells. In some embodiments, increase in expression of CLDN18.2 is only found in a diseased tissue, while the expression of CLDN18.2 in normal tissue is not detectable.

In some embodiments, the CLDN18.2-associated disease or condition is characterized in increased expression in cell surface or membrane-bound CLDN18.2.

In some embodiment, the CLDN18.2-related disease or condition is cancer. In one embodiment, cancer cells express or aberrantly express CLDN18.2 while the corresponding normal cells do not express CLDN18.2 or express CLDN18.2 at a lower level. It is believed that CLDN18.2 as a tight junction protein may be a good therapeutic target for CLDN18.2-associated disease such as tumor, and hence can be used to select patients eligible for treatment with CLDN18.2-targeting agents. Unlike normal epithelial tissue (except stomach epithelial cells) in which CLDNs associate to form classical tight junctions, CLDNs expressed in tumor cells often do not form such classical tight junctions, and as a result, tumor cells are likely to have free CLDNs that are exposed and accessible to extracellular antibody binding and immunotherapy.

CLDN18.2 is a valuable target for the prevention and/or treatment of primary tumors, such as gastric cancer, lung cancer (e.g. non-small cell lung cancer (NSCLC, squamous/nonsquamous), small cell lung cancer (SCLC)), bronchial cancer, bone cancer, liver and bile duct cancer, pancreatic cancer, breast cancer (including basal breast carcinoma, ductal carcinoma and lobular breast carcinoma), liver cancer, ovarian cancer, testicle cancer, kidney cancer, bladder cancer, head and neck cancer, spine cancer, brain cancer, cervix cancer, uterine cancer, endometrial cancer, hepatic cancer, head-neck cancer, cancer of gallbladder, colon cancer, colorectal cancer, rectal cancer, anal cancer, esophageal cancer, gastrointestinal cancer, skin cancer, prostate cancer, pituitary cancer, stomach cancer, vagina cancer, thyroid cancer, glioblastoma, astrocytoma, melanoma, myelodysplastic syndrome, sarcoma, teratoma, cholangiocarcinoma, and/or adenocarcinoma, and/or metastases thereof, in particular gastric cancer metastasis such as Krukenberg tumors, peritoneal metastasis, and lymph node metastasis.

Samples are preferably cancer cells or tissues and are, in particular, selected from the group consisting of tumorigenic gastric, esophageal, pancreatic, lung, ovarian, colon, hepatic, head-neck, and gallbladder cancer cells or tissues.

In certain embodiments, the cancer includes but are not limited to, renal cell cancer, gastric carcinoma, mesothelioma, melanoma, cervical cancer, thymic carcinoma, myelomas, mycoses fungoids, merkel cell cancer, hepatocellular carcinoma (HCC), fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma, classical Hodgkin lymphoma (CHL), primary mediastinal large B-cell lymphoma, T-cell/histiocyte-rich B-cell lymphoma, acute lymphocytic leukemia, acute myelocytic leukemia, acute myelogenous leukemia, chronic myelocytic (granulocytic) leukemia, chronic myelogenous leukemia, chronic lymphocytic leukemia, polycythemia vera, mast cell derived tumors, EBV-positive and -negative PTLD, and diffuse large B-cell lymphoma (DLBCL), plasmablastic lymphoma, extranodal NK/T-cell lymphoma, nasopharyngeal carcinoma, HHV8-associated primary effusion lymphoma, non-Hodgkin's lymphoma, multiple myeloma, Waldenstrom's macroglobulinemia, heavy chain disease, myelodysplastic syndrome, hairy cell leukemia and myelodysplasia, primary CNS lymphoma, spinal axis tumor, brain stem glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma.

In certain embodiments, the cancer is a CLDN18.2-expressing cancer. The presence or expression level of CLDN18.2 in the sample indicates whether cancer cells express CLDN18.2, and hence whether the cancer is likely to respond to treatment with a CLDN18.2-targeting agent.

"CLDN18.2-targeting agent" as used herein refers to one or more agents that target CLDN18.2 protein or nucleic acids (DNA or mRNA) in a cell, a tissue or a living body. A CLDN18.2-targeting agent may decrease/eliminate the expression of CLDN18.2 gene product, inhibit/disrupt the signaling of CLDN18.2, or induce cytotoxicity to cells that abnormally express CLDN18.2.

In certain embodiments, the CLDN18.2-targeting agent includes a therapeutic anti-CLDN18.2 antibody, a CLDN18.2-binding molecule, a cell therapy targeting CLDN18.2, a chemical compound targeting CLDN18.2, or a therapeutic nucleic acid targeting CLDN18.2. In certain embodiments, the CLDN18.2-targeting agent is capable of inducing cytotoxicity to CLDN18.2-expressing cells.

In certain embodiments, the CLDN18.2-targeting agent comprise a therapeutic anti-CLDN18.2 antibody or a CLDN18.2-binding molecule. In certain embodiments, the therapeutic anti-CLDN18.2 antibody or a CLDN18.2-binding molecule can induce ADCC, CDC or ADCP to the CLDN18.2-expressing cells. Alternatively, the therapeutic anti-CLDN18.2 antibody or a CLDN18.2-binding molecule can be conjugated to a cytotoxic agent, for example, to form an antibody-drug conjugate (ADC). In certain embodiments, the cytotoxic agent can be any agent that is detrimental to cells or that can damage or kill cells. In certain embodiments, the cytotoxic agent is optionally a toxin, a chemotherapeutic agent (such as a DNA-alkylators, a topoisomerase inhibitor, a tubulin-binders, a growth inhibitory agent, or other anticancer drugs), or a radioactive isotope. In other embodiments, the therapeutic anti-CLDN18.2 antibody can be a bispecific antibody that binds to different antigens or different epitopes on the CLDN18.2 protein.

In certain embodiments, the CLDN18.2-targeting agent comprise a CLDN18.2-targeting cell therapy. In certain embodiments, the CLDN18.2-targeting cell therapy includes a CAR-T (Chimeric Antibody Receptor Engineered T Cell), TCR-T (Gene Modified TCR T cells) or CAR-NK (Chimeric Antibody Receptor Engineered NK Cell) expressing a CLDN18.2-binding Chimeric Antibody Receptor (CAR). Chimeric antigen receptors (CARs) are engineered chimeric receptors that combine an antigen-binding domain of an antibody with one or more signaling domains for T cell activation. Immune cells such as T cells and Nature Killer (NK) cells can be genetically engineered to express CARs or genetically modified TCRs (see, for details, D. Li et al, Sig Transduct Target Ther 4, 35 (2019), S. Kloess et al, Transfus Med Hemother; 46:4-13(2019), Wang W. et al, Cancer Letters, 472: 175-180(2020)). T cells expressing a CAR are referred to as CAR-T cells. CAR can mediate antigen-specific cellular immune activity in the T cells, enabling the CAR-T cells to eliminate cells (e.g. tumor cells) expressing the targeted antigen. In one embodiment, binding of the CAR-T cells provided herein to CLDN18.2 expressed on cells such as cancer cells, results in proliferation and/or activation of said CAR-T cells, wherein said activated CAT-T cells can release cytotoxic factors, e.g. perforin, granzymes, and granulysin, and initiate cytolysis and/or apoptosis of the cancer cells.

In certain embodiments, the therapeutic nucleic acid targeting CLDN18.2 can be short interfering nucleic acid (siNA), short interfering RNA (siRNA), double-stranded RNA (dsRNA), micro-RNA (miRNA), and short hairpin RNA (shRNA) molecules capable of mediating RNA interference (RNAi) against CLDN18.2 gene sequence, or another gene sequence in the CLDN18.2-expressing cell.

In certain embodiments, a CLDN18.2-targeting agent promotes cancer regression in a subject. In preferred embodiments, a therapeutically effective amount of the CLDN18.2-targeting agent promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction.

In certain embodiments, the subject is receiving or has received anti-cancer-therapy, or suffers from cancer recurrence. An anti-cancer-therapy includes, for example, but not limited to, a chemotherapeutic agent, an anti-cancer drug, radiation therapy, an immunotherapy, anti-angiogenesis agent, a targeted therapy, a cellular therapy, a gene therapy, a hormonal therapy, palliative care, surgery for the treatment of cancer (e.g., tumorectomy), or one or more anti-emetics or other treatments for complications arising from chemotherapy.

A relapse or recurrence occurs when a person is affected again by a condition that affected them in the past. For example, if a patient has suffered from a cancer disease, has received a successful treatment of said disease and again develops said disease. Said newly developed disease may be considered as relapse or recurrence. However, according to the present disclosure, a relapse or recurrence of a cancer disease may, but does not necessarily, occur at the site of the original cancer disease. Thus, for example, if a patient has suffered from gastric tumor and has received a successful treatment, a relapse or recurrence may be the occurrence of a gastric tumor or the occurrence of a tumor at a site different to stomach. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

Kits

In certain embodiments, the present disclosure provides kits comprising the isolated antibody or antigen-binding fragment thereof provided herein. In certain embodiments, the kit disclosed herein is a diagnostic kit. The kits may be useful in detection of presence or amount of CLDN18.2 in a biological sample, or may be useful in the methods of diagnosis provided herein.

In certain embodiments, the kit comprises the antibody or the antigen binding fragment thereof provided herein which is optionally detectably labeled. In certain embodiments, the antibody or the antigen binding fragment thereof is conjugated with an indirectly detectable moiety.

In certain embodiments, the kit further comprises a set of reagents for detecting a complex of the antibody or antigen-binding fragment thereof bound to CLDN18.2, useful in a variety of detection assays, including for example, immunoassays such as IHC, ICC, or ELISA (sandwich-type or competitive format).

In yet another embodiment of the invention, the reagents useful to perform immunohistochemistry on an FFPE tumor tissue section are provided in a kit along with instructions for performing the IHC assay.

Any of the indirectly detectable labels or moieties disclosed herein can be used. In certain embodiments, the indirectly detectable moiety comprises biotin. In such embodiments, the set of reagents comprises a detectably labeled avidin or steptavidin.

In certain embodiments, a detectable label is conjugated to the antibody or antigen-binding fragment thereof provided herein. In certain embodiments, the kits comprise the isolated antibody or antigen-binding fragment thereof provided herein and a secondary antibody that is conjugated with a detectable label. In some embodiments, the secondary antibody comprises an antibody that specifically binds to the primary antibody (e.g. the antibody or antigen-binding fragment thereof provided herein). In some embodiments, the secondary antibody can be an anti-mouse antibody, an anti-rabbit antibody, or anti-human antibody.

The detectable label may require combination with one or more components, e.g., buffers, antibody-enzyme conjugates, enzyme substrates, or the like, prior to use, and such reagents can be included in the kits. For example, when the detectable moiety comprises an enzyme, the kit will include substrates and co factors required by the enzyme (e.g., a substrate precursor which provides the detectable chromophore or fluorophore). In addition, other reagents may be included such as blocking reagents for reducing nonspecific binding to the solid phase surface, washing reagents, enzyme substrates, and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. Instructions, either as inserts or a label, indicating guidelines for detection and/or assay system preparation, can also be included in the kit.

The kit's components may be pre-attached to a solid support, or may be applied to the surface of a solid support when the kit is used. The solid phase surface may be in the form of a tube, a bead, a microtiter plate, a microsphere, or other materials suitable for immobilizing proteins, peptides, or polypeptides.

Containers for use in such kits may typically comprise at least one vial, test tube, flask, bottle, syringe or other suitable container, into which one or more of the detection composition(s) may be placed, and preferably suitably aliquoted. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection composition itself, or may alternatively be placed in a second distinct container means into which this second composition may be placed and suitably aliquoted. Alternatively, the detection reagent may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

EXAMPLES

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

Example 1: Preparation of Antigen for Immunization

1. Design of Antigen Peptide

To limit antibodies' epitope to CLDN18.2 not to CLDN18.1, a peptide which is unique to CLDN18.2 (Genbank accession number: NP_001002026) was designed by MabSpace Biosciences (Suzhou) Co., Limited. The coding sequence of this peptide (SEQ ID No. 19: DQWSTQDLYN) was located at amino acid residues Asp28-Asn37 (D28 to N37) of CLDN18.2.

2. Synthesis of Peptide

The antigen peptide was synthesized in SANGON BIOTECH (Shanghai) and used for animal immunization.

Example 2: Antibody Generation

1. Immunization and Hybridoma Fusion 6-8 weeks different strains of mice were immunized with 40 g/mouse peptide (conjugated with KLH) with CFA as adjuvant, each mouse was received 11 boosts (multiple sites subcutaneously injection) in 3 time a week for 4 weeks and followed by a week interval boost for 2 times, 3 days after a primary immunization. For determining the serum titer, 100 μl/well serially diluted mouse serum was added into the plate that was coated by the antigen peptide, and then incubated at 4° C. for 30 min. The plate was washed 3 times by washing buffer and then 100 μl/well goat anti-mIgG-HRP was added for another incubation at 4° C. Followed by washing with washing buffer, TMB was added to react with HRP on the plate. Then OD450 nm of the plate was read by microplate reader and the titer was analyzed by Graphpad Prism 6 software. Mice with the higher titer were selected for the following fusion procedures.

2. Fusions

Four days prior to fusion, each mouse was boosted intraperitoneally with 20 μg peptide. On the fusion day, the spleens were removed aseptically and then processed into a single cell suspension. The red blood cells were lysed to give the splenocytes. Viable, log-phase myeloma cells (SP2/0) were mixed with the murine splenocytes in a 1:1 ratio in a fusion medium following by electrofusion for 1 min. Cells were resuspended and cultured in 96-well culture plates at a 37° C., 5% CO2 incubator. After 7 days' culture, the growth media was exchanged for fresh growth media. Screening of hybridoma supernatants commenced 2-3 days after fresh growth media change.

Example 3: Binding Screening, Subcloning of the Positive Hybridoma Clones and Small-Scale Antibody Production 1. Binding Screening by a ELISA Assay Hybridoma supernatants were collected for antigen binding screening. 100 μl/well the hybridoma supernatants were added to the plate that was coated by the antigen peptide, and then incubated at 4° C. for 1 hr. The plate was washed 3 times by washing buffer and then 100 μl/well goat anti-mIgG-HRP was added for another incubation at 4° C. Followed by washing with washing buffer, TMB was added to react with HRP on the plate. Then OD490 nm of the plate was read by microplate reader. The ELISA binding positive clones were selected and expanded. After 2 days, the binding of hybridoma supernatants of the selected clones were tested in the same way and the positive clones were proceeded to subcloning.

2. Subcloning of the Positive Hybridoma Clones

Cells from the positive hybridoma wells with the desired binding profile were selected for a limited dilution in 96-well plates. The diluted cells were allowed to grow for 7 days. Upon adequate cell mass was reached, supernatant from each well was collected and re-screened by using the same ELISA binding assay above.

From each 96-well plate, the clone with a highest cell binding activity was expanded for 2nd round limited dilution into a 96-well plate with 200 μl of hybridoma growth medium per well. After 7 days, supernatant of cells from the 96-well plates were analyzed by the same ELISA binding assay. The subcloning was done more than 2 times until more than 90/96 wells display a positive binding signal. Two subclones (i.e. 69H2 and 14G11) with the highest binding activity of each clone were identified, expanded and cultured for purified antibody production. Isotypes were determined using a standard method.

3. Small-Scale Antibody Production

Hybridoma cells were inoculated and cultured for 14 days. Monoclonal antibodies (mAbs) were purified from the hybridoma cell culture by Protein A affinity chromatography (Protein A High Performance (Bio-Rad)).

After chromatography purification, these mAbs were formulated in PBS by dialysis, followed by a step of filtration.

Example 4: Antibody Immunocytochemical Screening on Cell Blocks

1. Cell Block Sections Preparation

HEK293-human CLDN18.2 cell (hereafter referred as HEK293-CLDN18.2) and HEK293-human CLDN18.1 cell (hereafter referred as HEK293-CLDN18.1) were constructed by MabSpace Biosciences (Suzhou) Co. Limited. Briefly, HEK293 cell (Shanghai Institutes for Biological Sciences, Cat #GNhu43) was transfected with pcDNA3.1/hCLDN18.2 or pcDNA3.1/hCLDN18.1 plasmids, and selected with G418 to obtain stable expressing cell line HEK293-CLDN18.2 or HEK293-CLDN18.1. The expression of CLDN18.1 on HEK293-CLDN18.1, and the expression of CLDN18.2 on HEK293-CLDN18.2 were tested and confirmed by FACS, using positive control antibodies respectively. As shown in FIG. 1, HEK293-CLDN18.1 cells showed positive binding signal for antibody EPR19203 (available from Abcam under product name ab222513) that binds to CLDN18.1, and HEK293-CLDN18.2 cells showed positive binding signal for antibody 18B10 (see PCT application PCT/CN2019/101563) that specifically binds to human CLDN18.2.

HEK293 and HEK293 cells having high expression level of human CLDN18.2 (HEK293-CLDN18.2) or CLDN18.1 (HEK293-CLDN18.1) were harvested and fixed in 4% neutral buffered paraformaldehyde (PFA) for 30 min at room temperature. After centrifugation, cells were resuspended in PBS, subsequently dispersed into 200 μl molten agar at 57° C. and solidified at 4° C. immediately. The agar-cell mix were dehydrated in gradient alcohol, and cleared in xylene. After being infiltrated in paraffin wax at 60° C., the agar-cell mix were embedded in paraffin wax according to standard procedure and cut into sections at a thickness of 3 m, which were mounted onto positive charged slides immediately.

2. Antibody Immunocytochemical Screening on Cell Block Sections

To screen CLDN18.2 specific and sensitive antibodies, Immunocytochemistry (ICC) was performed using paraffin embedded (FFPE) HEK293, HEK293-CLDN18.2 and HEK293-CLDN18.1 cell block sections. After deparaffinization and rehydration, all sections were proceeded to antigen retrieval by boiling in EnVision™ FLEX Target Retrieval Solution (Dako, K8002) for 25 minutes at 97-99° C., subsequently quenched, blocked with EnVision™ FLEX Peroxidase-Blocking Reagent (Dako, K8002) and incubated with appropriately diluted antibodies. Antibody binding was visualized with EnVision™ FLEX+, Mouse (LINKER), followed by EnVision™ FLEX/hRP and EnVision™ FLEX Substrate Working Solution (Dako, K8002). Sections were finally counterstained with Hematoxylin and mounted with permanent mounting medium. No significant difference in staining pattern was observed and staining intensity between antibodies varied from weak to strong.

Figure 2:
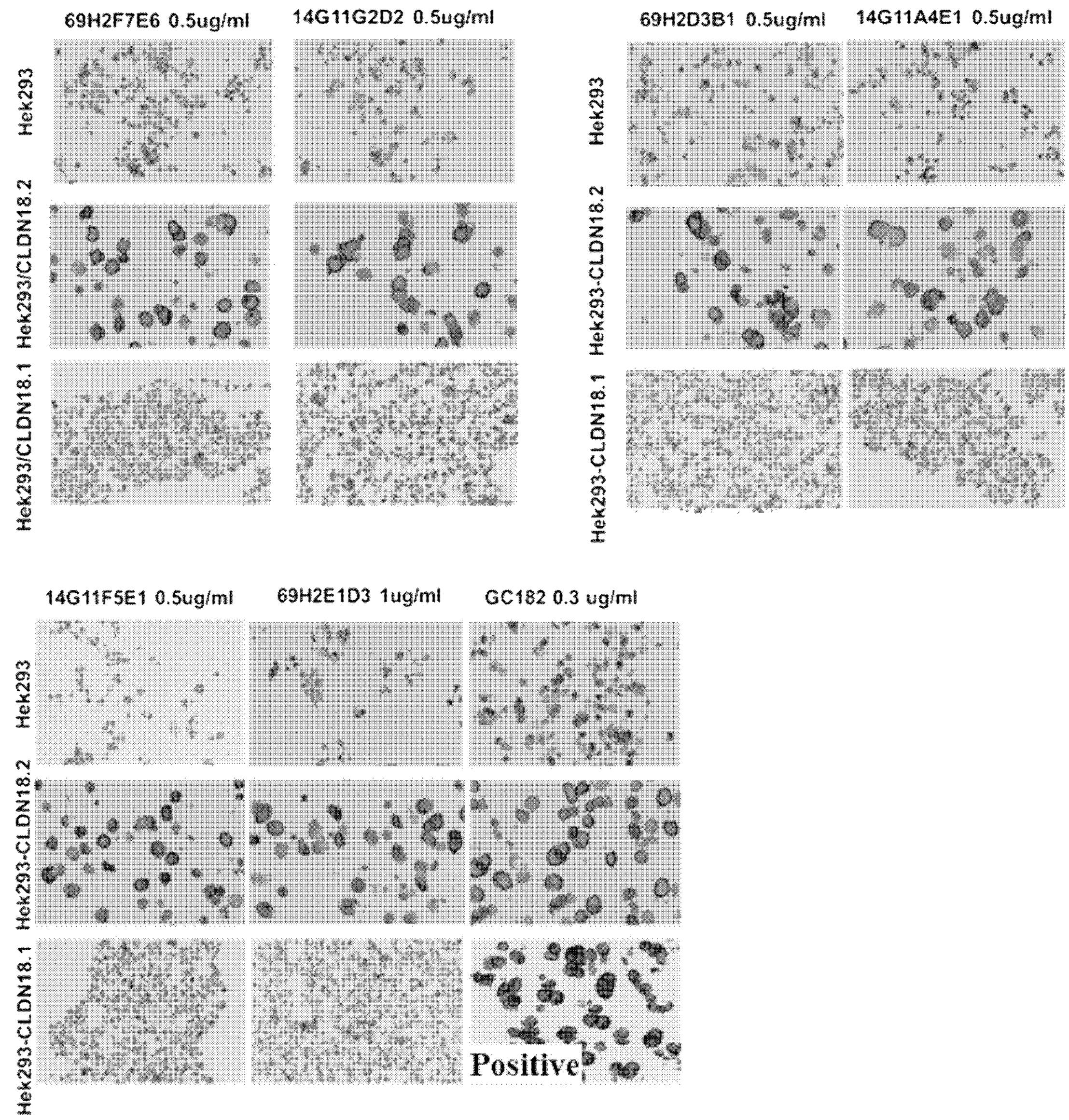
FIG. 2 shows immunocytochemistry (ICC) staining of antibodies 69H2 and 14G11 screened on HEK293, HEK293-CLDN18.1, HEK293-CLDN18.2 cell block sections. Staining of antibody GC182 was used as a control.

As shown in Table 3 and FIG. 2, clones of antibodies 69H2 and 14G11 were strongly and specifically stained on HEK293-CLDN18.2 surface but negatively on HEK293 and HEK293-CLDN18.1 at 1 nM and were further titrated to 0.5 nM to test the sensitivity. 69H2F7E6, 69H2D3B1, 69H2E1D3 are all clones of antibody 69H2, and shared the same heavy chain and light chain sequences with 69H2. 14G11G2D2, 14G11A4E1, and 14G11F5E1 are all clones of antibody 14G11, and shared the same heavy chain and light chain sequences with 14G11.

Staining of anti-CLDN18.2 antibody GC182 was used as a control, which stained positively on both HEK293-CLDN18.2 and HEK293-CLDN18.1 cells. The antibody GC182 has a heavy chain variable region sequence of SEQ ID NO: 22 and a light chain variable region sequence of SEQ ID NO: 23 and was generated by Mabspace Bioscience according to the sequences disclosed in WO2013167259. Results in Table 3 indicated that antibody GC182 could cross-react with CLDN18.1, and hence was not specific to CLDN18.2.

```
GC182 heavy chain variable region sequence
(SEQ ID NO: 22):
QIQLVQSGPELKKFGETVKISCKASGYTFTDYSIHWVKQAPGKGLKWMGW

INTETGVPTYADDFKGRFAFSLETSASTAYLQINNLKNEDTATYFCARRT

GFDYWGQGTTLTVSS

GC182 light chain variable region sequence
(SEQ ID NO: 23):
DIVMTQAAFSIPVTLGTSASISCRSSKNLLHSDGITYLYWYLQRPGQSPQ

LLIYRVSNLASGVPNRFSGSESGTDFTLRISRVEAEDVGVYYCVQVLELP

FTFGGGTKLEIK
```

TABLE 3

Antibody Screen on Cell Block Sections by Immunocytochemical Staining

| Purified antibodies | Cell type | Cryo-/ Paraffin | Antibody Conc. (nM) | Staining intensity | Subcellular pattern |
|---|---|---|---|---|---|
| 69H2F7E6 | HEK293 | Paraffin | 1 | − | n.a. |
| | HEK293 | Paraffin | 0.5 | − | n.a. |
| | HEK293-CLDN18.1 | Paraffin | 1 | − | n.a. |
| | HEK293-CLDN18.1 | Paraffin | 0.5 | − | n.a. |
| | HEK293-CLDN18.2 | Paraffin | 1 | ++ | m |
| | HEK293-CLDN18.2 | Paraffin | 0.5 | + | m |
| 14G11G2D2 | HEK293 | Paraffin | 1 | − | n.a. |
| | HEK293 | Paraffin | 0.5 | − | n.a. |
| | HEK293-CLDN18.1 | Paraffin | 1 | − | n.a. |
| | HEK293-CLDN18.1 | Paraffin | 0.5 | − | n.a. |
| | HEK293-CLDN18.2 | Paraffin | 1 | ++ | m |
| | HEK293-CLDN18.2 | Paraffin | 0.5 | + | m |
| 69H2D3B1 | HEK293 | Paraffin | 1 | − | n.a. |
| | HEK293 | Paraffin | 0.5 | − | n.a. |
| | HEK293-CLDN18.1 | Paraffin | 1 | − | n.a. |
| | HEK293-CLDN18.1 | Paraffin | 0.5 | − | n.a. |
| | HEK293-CLDN18.2 | Paraffin | 1 | ++ | m |
| | HEK293-CLDN18.2 | Paraffin | 0.5 | + | m |
| 14G11A4E1 | HEK293 | Paraffin | 1 | − | n.a. |
| | HEK293 | Paraffin | 0.5 | − | n.a. |
| | HEK293-CLDN18.1 | Paraffin | 1 | − | n.a. |
| | HEK293-CLDN18.1 | Paraffin | 0.5 | − | n.a. |
| | HEK293-CLDN18.2 | Paraffin | 1 | ++ | m |
| | HEK293-CLDN18.2 | Paraffin | 0.5 | + | m |
| 14G11F5E1 | HEK293 | Paraffin | 1 | − | n.a. |
| | HEK293 | Paraffin | 0.5 | − | n.a. |
| | HEK293-CLDN18.1 | Paraffin | 1 | − | n.a. |
| | HEK293-CLDN18.1 | Paraffin | 0.5 | − | n.a. |
| | HEK293-CLDN18.2 | Paraffin | 1 | ++ | m |
| | HEK293-CLDN18.2 | Paraffin | 0.5 | + | m |
| 69H2E1D3 | HEK293 | Paraffin | 1 | − | n.a. |
| | HEK293 | Paraffin | 0.5 | − | n.a. |
| | HEK293-CLDN18.1 | Paraffin | 1 | − | n.a. |
| | HEK293-CLDN18.1 | Paraffin | 0.5 | − | n.a. |
| | HEK293-CLDN18.2 | Paraffin | 1 | ++ | m |
| | HEK293-CLDN18.2 | Paraffin | 0.5 | + | m |

TABLE 3-continued

| Antibody Screen on Cell Block Sections by Immunocytochemical Staining | | | | | |
|---|---|---|---|---|---|
| Purified antibodies | Cell type | Cryo-/ Paraffin | Antibody Conc. (nM) | Staining intensity | Subcellular pattern |
| GC182 | HEK293 | Paraffin | 0.3 | − | n.a. |
| | HEK293-CLDN18.1 | Paraffin | 0.3 | + | m |
| | HEK293-CLDN18.2 | Paraffin | 0.3 | + | m |

Note:
staining intensity (neg: −; weak: +−; moderate: +; strong: ++).
m: membrane
n.a.: not applicable

Example 5: Cloning and Recombination Production of Selected Antibodies

Generation of Recombinant Antibodies

The sequences in the light chain and heavy chain variable regions of the mouse anti-human CLDN18.2 antibodies 14G11 and 69H2 were obtained by polymerase chain reaction (PCR) amplification from the candidate hybridoma cell lines. After sequencing analysis and confirmation, the variable region genes, including the sequence of the light chain variable region (VL) fused to mouse kappa constant region and the sequence of the heavy chain variable region (VH) fused to mouse IgG1 constant region, were cloned into a recombinant expression vector, pcDNA3.1(+), for antibody production and purification.

The heavy chain and light chain of 14G11 and 69H2 antibodies were linked to mouse IgG1 heavy chain constant region and kappa light chain constant region, respectively, as shown below:

```
Mouse IgG1 heavy chain constant region
(SEQ ID NO: 17):
AKTTPPSVYPLAPGSAAQTNSMVTLGCLVKGYFPEPVTVTWNSGSLSSGV

HTFPAVLQSDLYTLSSSVTVPSSTWPSQTVTCNVAHPASSTKVDKKIVPR

DCGCKPCICTVPEVSSVFIFPPKPKDVLTITLTPKVTCVVVDISKDDPEV

QFSWFVDDVEVHTAQTKPREEQINSTFRSVSELPIMHQDWLNGKEFKCRV

NSAAFPAPIEKTISKTKGRPKAPQVYTIPPPKEQMAKDKVSLTCMITNFF

PEDITVEWQWNGQPAENYKNTQPIMDTDGSYFVYSKLNVQKSNWEAGNTF

TCSVLHEGLHNHHTEKSLSHSPGK

Mouse Kappa light chain constant region
(SEQ ID NO: 18):
RADAAPTVSIFPPSSEQLTSGGASVVCFLNNFYPKDINVKWKIDGSERQN

GVLNSWTDQDSKDSTYSMSSTLTLTKDEYERHNSYTCEATHKTSTSPIVK

SFNRNEC
```

Expression and Purification of Recombinant Antibodies

ExpiCHO cells were transfected by using ExpiCHO transfection kit with an equal amount of DNA from the heavy chain vector and the light chain vector. The transfected cells were cultured in shake flasks at 125 rpm in 37° C. incubator with 8% CO2. Cell Culture was harvested on day 10, and the harvested antibodies were purified by affinity chromatography. The resulting antibody was analyzed to determine the level of purity using SDS-PAGE and size exclusion chromatography (TSK gel G3000SWXL, TOSOH).

Example 6: Binding Selectivity Evaluation of hCLDN18.2 to hCLDN 18.1 by ELISA and FACS Assay

Specific Binding with hCLDN18.2 Peptide (Aa28-37) by ELISA

Figure 3:
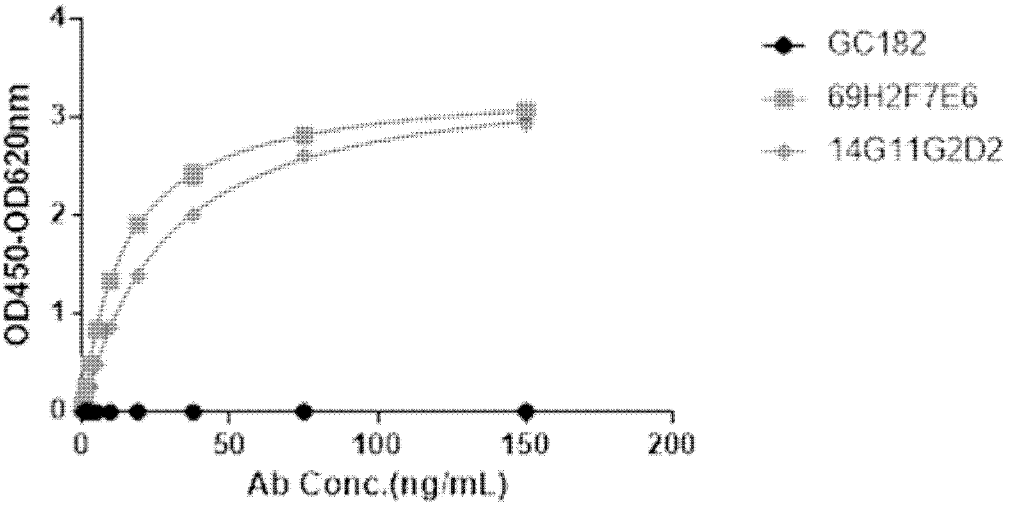
FIG. 3 shows binding profiles and EC50 of anti-CLDN18.2 antibodies, 69H2F7E6, 14G11G2D2 and GC182, binding with hCLDN18.2 peptide (amino acid residues 28-37 of hCLDN18.2).

1 μg/ml of peptide (100 μL/well) was coated onto the high-binding clear polystyrene 96 well plates and blocked with blocking buffer. Serial diluted antibodies (from 150 to 0.0732 ng/ml) in blocking buffer were then added and incubated for 1.5 hrs at room temperature. The plate was washed 6 times using washing buffer and then 100 μl/well Goat pAb to Ms IgG(HRP) was added for incubation at room temperature for 1.5 hr. After washing with washing buffer, TMB was added to react with HRP on the plate. Then OD450 nm of the plate was read by SpectraMax i3x (Molecular Devices). 14G11G2D2 and 69H2F7E6 can specifically bind with the peptide with high affinity while CC182 can not recognize the epitope in the linear peptide. (FIG. 3)

Binding Selectivity Analysis of Recombinant Anti-Claduin18.2 Antibodies to Recombinant hCLDN18.2 and hCLDN18.1 Protein by ELISA Human recombinant CLDN1.8.2(N-6His) variant (obtained from Novoprotein under the catalog number NC101) and human recombinant CLDN18.1(N-8His) variant (obtained from Novoprotein under the catalog number CR54) were used in this assay. The human recombinant CLDN18.2 (N-6His) variant is a fusion polypeptide containing the extracellular domain (residues Ala24-Ala81, SEQ ID NO: 26) of human CLDN 18.2 flanked by sequences that can fold or associate to allow the extracellular domain of human CLDN 18.2 to form a loop. Similarly, the human recombinant CLDN18.1 (N-8His) variant is a fusion polypeptide containing the extracellular domain of human CLDN 18.1 (residues Asp28-Leu76, SEQ ID NO: 27) flanked by sequences that can fold or associate to allow the extracellular domain of human CLDN 18.1 to form a loop.

Figure 4:
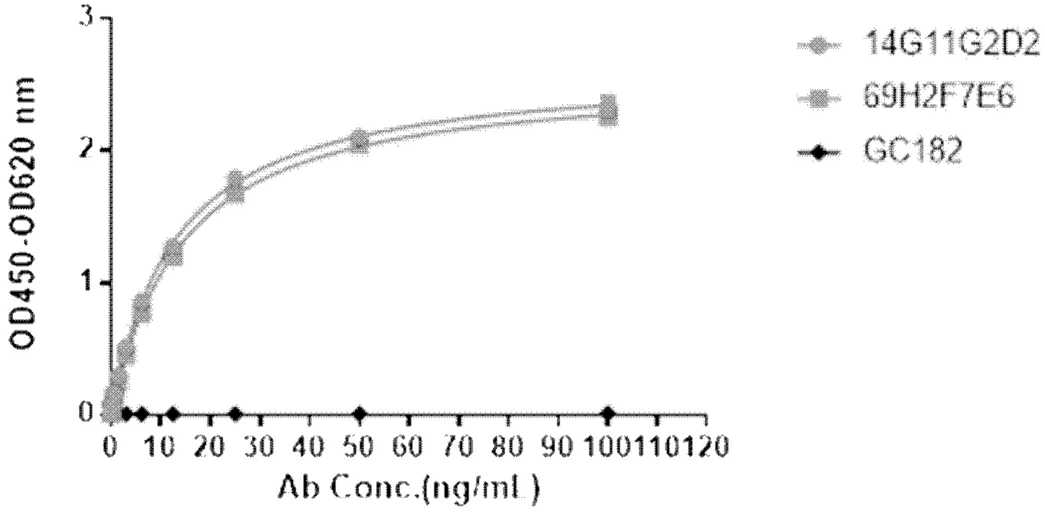
FIG. 4 shows binding profiles and EC50 of anti-CLDN18.2 antibodies, 69H2F7E6, 14G11G2D2 and GC182, binding with recombinant hCLDN18.2 variant protein comprising the amino acid sequence of ECL1 loop of hCLDN18.2 (SEQ ID NO: 26), as measured by ELISA.
Figure 5:
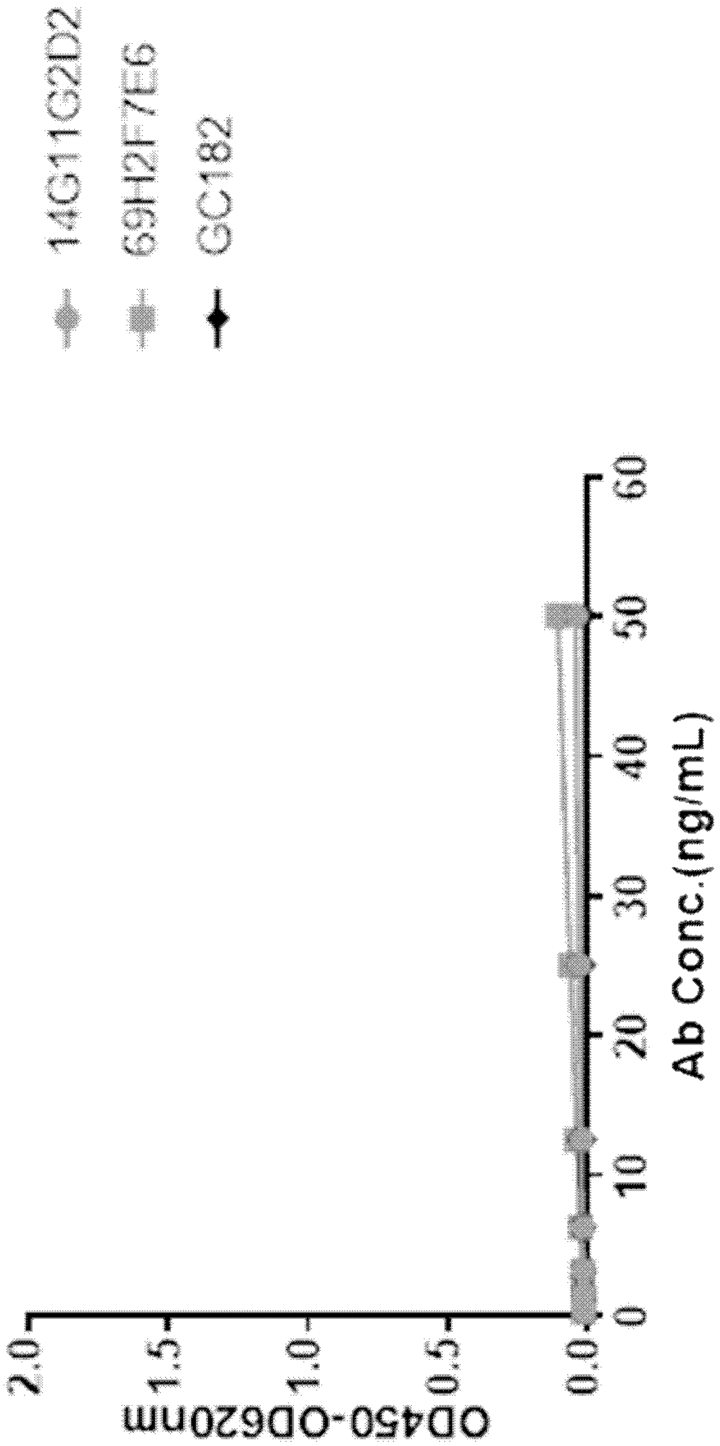
FIG. 5 shows binding profiles and EC50 of anti-CLDN18.2 antibodies, 69H2F7E6, 14G11G2D2 and GC182, binding with recombinant hCLDN18.1 variant protein comprising the amino acid sequence of ECL1 loop of hCLDN18.1 (SEQ ID NO: 27), as measured by ELISA.

1 μg/ml of human recombinant CLDN18.2(N-6His) variant or human recombinant CLDN18.1(N-8His) variant (100 μL/well) was coated onto the high-binding clear polystyrene 96 well plates and blocked with blocking buffer. Serial diluted antibodies (from 100 to 0.0244 ng/ml) in blocking buffer were added and incubated for 1.5 hrs at room temperature. The plate was washed 6 times using washing buffer (PBS+0.1% Tween) washer and then 100 μl/well Goat pAb to Ms IgG (HRP) was added for incubation at RT for 1.5 hr. After washing with washing buffer, TMB was added to react with HRP on the plate. Then OD450 nm of the plate was read by SpectraMax i3x (Molecular Devices). Both 14G11G2D2 and 69H2F7E6 can specifically bind to human recombinant CLDN18.2(N-6His) with high affinity, with an EC50 of 12.75 ng/ml and 13.87 ng/ml, respectively (FIG. 4). Neither of 14G11G2D2 and 69H2F7E6 showed specific binding to human recombinant CLDN18.1(N-8His) protein (FIG. 5). As a control, CC182 showed no specific binding to human recombinant CLDN18.2(N-61-His) or human recombinant CLDN18.1(N-8His) (FIG. 4, 5) This indicates that 14G11G2D2 and 69H2F7E6 binds to an epitope within the extracellular domain of CLDN18.2, but CC182 does not recognize such an epitope.

FACS Analysis on HEK293-hCLDN18.2 and HEK293-hCLDN 18.1 Cell Lines

Log phase HEK293-hCLLDN18.2 or HEK293-hCLDN18.1 cells were collected, washed and resuspended. The diluted antibodies (20 ug/mL) in blocking buffer were added and were incubated at 4° C. for 1 hr. The cells were then washed twice with blocking buffer, followed by adding 2nd antibody (Goat anti-Mouse IgG (H+L) Cross-Adsorbed Secondary Antibody, Alexa Fluor 488, ThermoFisher) in blocking buffer. The cells were incubated at 4° C. for 1 hr, then washed twice with blocking buffer, and resuspended in blocking buffer. The cells were then transferred into FACS tube and the bindings of the antibodies to the cells were detected using flow cytometry (BD Accuri C6). Antibodies 18B10 and EPR19203 were used as positive controls for analysis on HEK-hCLDN18.2 cells and HEK-hCLDN 18.1 cells, respectively. As shown in FIG. 1, neither antibodies 14G11G2D2 and 69H2F7E6 can bind human Claudin18.2 or Claudin 18.1 expressed on the cell surface with native conformations.

Figure 6:
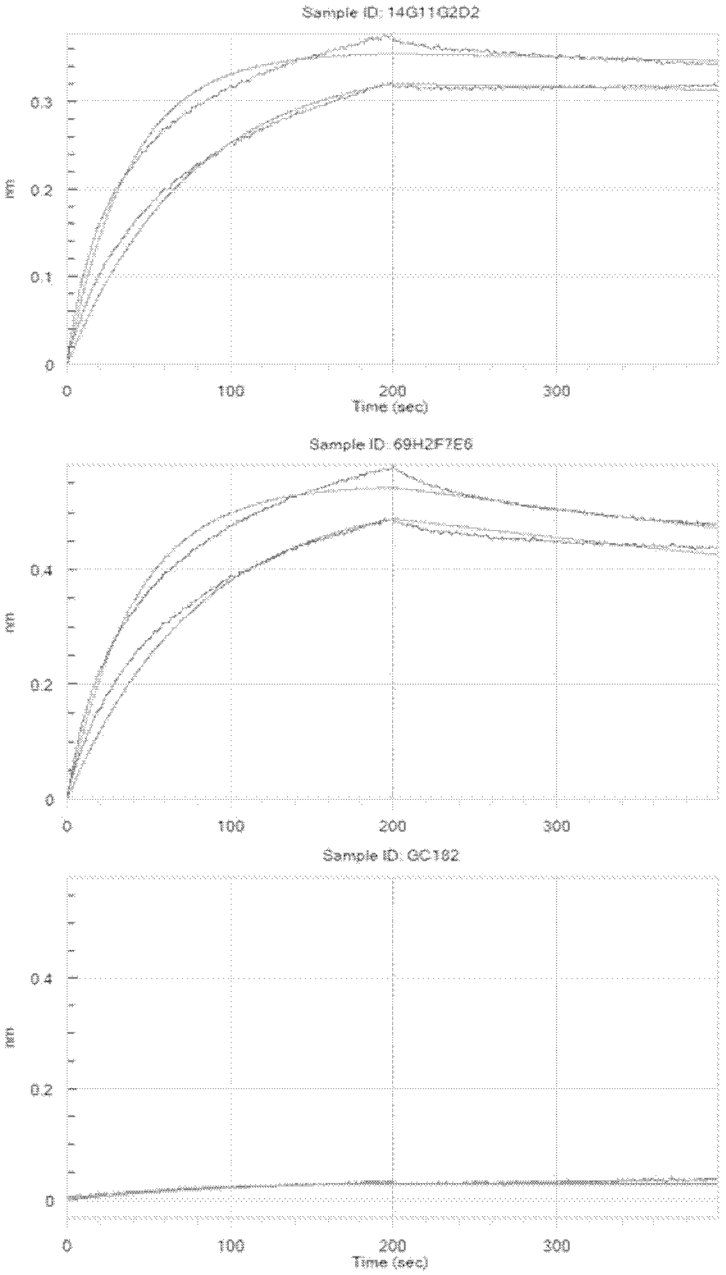
FIG. 6 shows binding affinity analysis of anti-CLDN18.2 antibodies, 69H2F7E6, 14G11G2D2, GC182 with recombinant hCLDN18.2 variant protein by ForteBio. The KD, kon and koff are shown.

Example 7: Binding Affinity Determination of Recombinant Anti-Claudin 18.2 to Recombinant hCLDN18.2 Protein by ForteBio 100 nM human recombinant CLDN18.2(N-6His) (Novoprotein, NC101) protein in 1×Kinetics Buffer ((PBS+0.1% BSA+0.02% Tween20) were loaded onto pre-wet Ni-NTA biosensors (PALL, 18-5101) for 200s. After equilibrated in 1×Kinetics Buffer as baseline (60s), the sensor was immersed into serial diluted antibodies (50 nM, 25 nM) with 1×Kinetics Buffer respectively and incubated for 200s to determine the association (kon), followed by dissociation in 1×Kinetics Buffer for 200s (koff). The biosensors are regenerated for 5s in Regeneration Buffer, followed by neutralization for 5s in Neutralization Buffer for 3 times. All procedure were performed at 30° C. with Octet RED 96 (PALL). The binding affinity KD was calculated and analyzed using the ratio of koff to kon.(FIG. 6). 69H2F7E6 showed a KD value of 1.48 nM, and 14G11G2D2 showed a KD value of 0.213 nM.

Example 8: Specificity Verification of Antibody Using Normal Tissues

CLDN18.2 is a highly selective gastric lineage antigen whose expression is restricted to short-lived differentiated epithelial cells of gastric mucosa whereas CLDN18.1 expression is restricted to lung. On this basis, the selected antibodies were analyzed on various, relevant normal tissues to confirm the specific binding to CLDN18.2 but not to CLDN18.1. Immunohistochemistry (IHC) was performed on 4% neutral buffered formalin fixed paraffin embedded (FFPE) normal intestine, kidney, tonsil, thyroid, skeletal muscle, stomach, lung and breast sections. After deparaffinization and rehydration, all sections were proceeded to antigen retrieval by boiling in EnVision™ FLEX Target Retrieval Solution (Dako, K8002) for 25 minutes at 97-99° C., subsequently quenched, blocked with EnVision™ FLEX Peroxidase-Blocking Reagent (Dako, K8002) and incubated with appropriately diluted antibodies. Antibody binding was visualized with EnVision™ FLEX+, Mouse (LINKER), followed by EnVision™ FLEX/hRP and EnVision™ FLEX Substrate Working Solution (Dako, K8002). Sections were finally counterstained with Hematoxylin and mounted with permanent mounting medium.

Figure 7A:
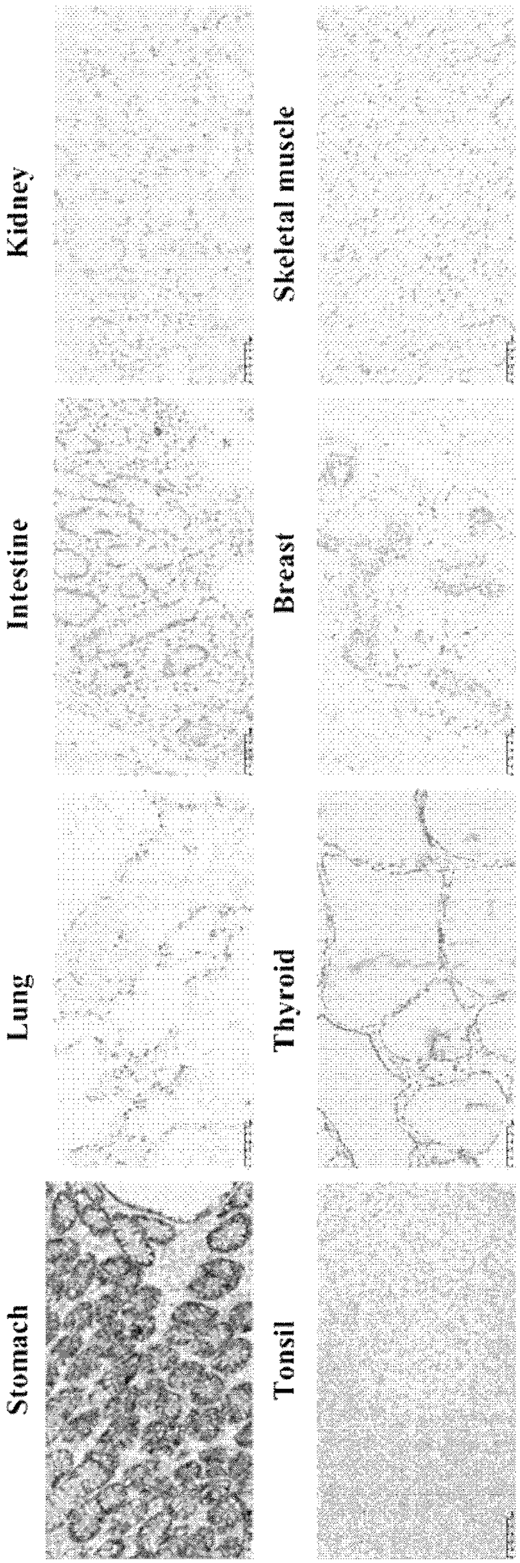
FIGS. 7A and 7B shows immunohistochemistry (IHC) analysis of selected antibodies 14G11G2D2, 69H2F7E6, and GC182, respectively, on formalin fixed paraffin embedded (FFPE) normal stomach, lung, intestine, kidney, tonsil, thyroid, breast and skeletal muscle tissue sections. The arrow shows the positive staining of GC182 on normal lung tissue.
Figure 7B:
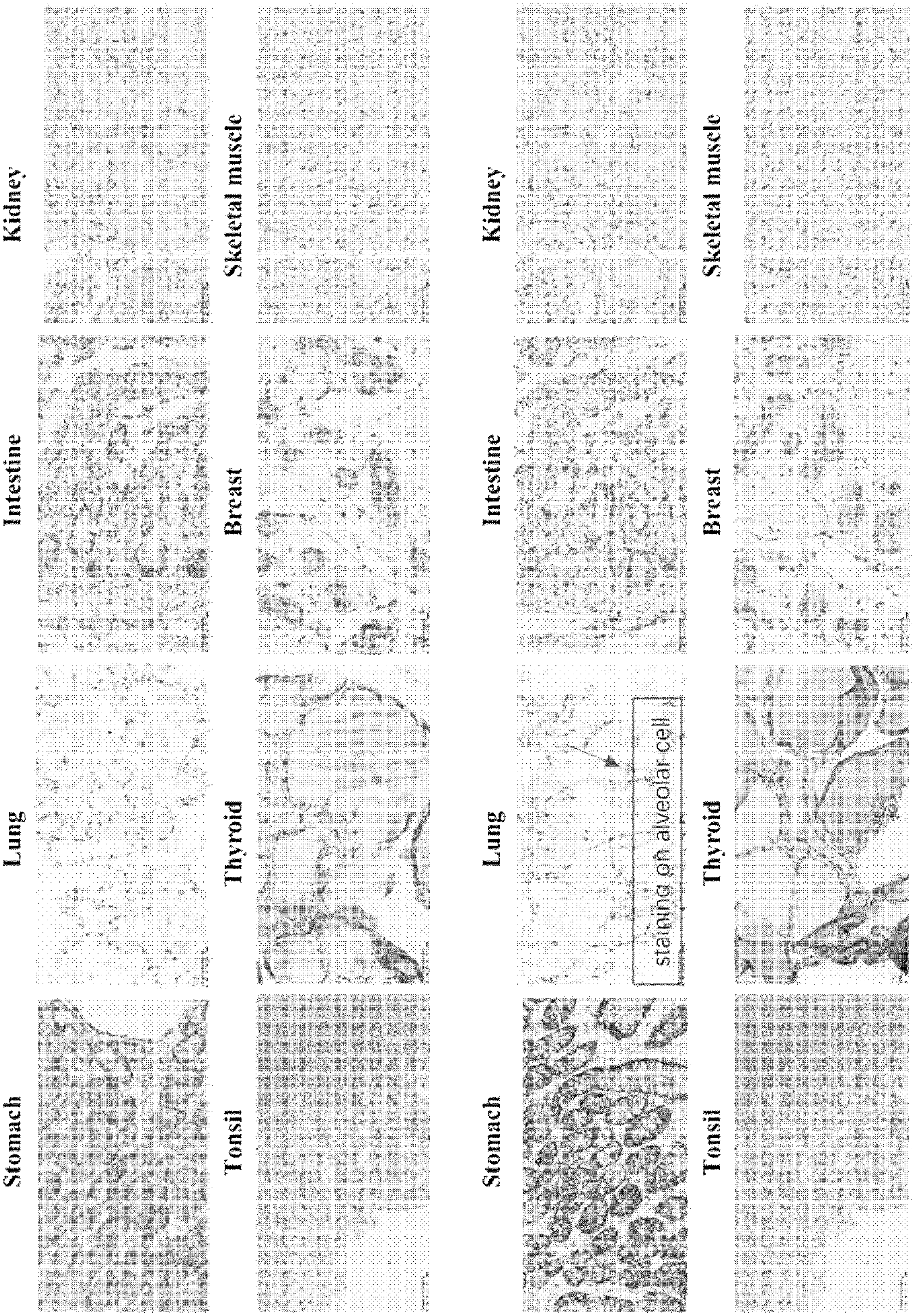

Clones 14G11G2D2 and 69H2F7E6 were selected for further specificity analysis on FFPE normal tissues. Both 69H2F7E6 and 14G11G2D2 performed well on the staining intensity, pattern and selectivity. Both 69H2F7E6 and 14G11G2D2 showed strong staining intensity in FFPE stomach sections, but negligible staining on lung, intestine, kidney, skeletal muscle, tonsil, thyroid, and breast sections (see Table 4 and FIGS. 7A and 7B). All stained cells are epithelial cells, but not other cell types including lymphocyte, vessel, fibrocyte, or smooth muscle cells. In contrast, anti-CLDN18.2 antibody GC182 showed strong and moderate staining intensity in FFPE stomach and lung sections, respectively, confirming that it binds to both CLDN18.2 and CLDN18.1. Comparatively, 14G11G2D2 performed better than 69H2F7E6 and was selected as the candidate for further IHC test. The analysis results of IHC staining were shown in Table 4 and FIGS. 7A and 7B.

Figure 8:
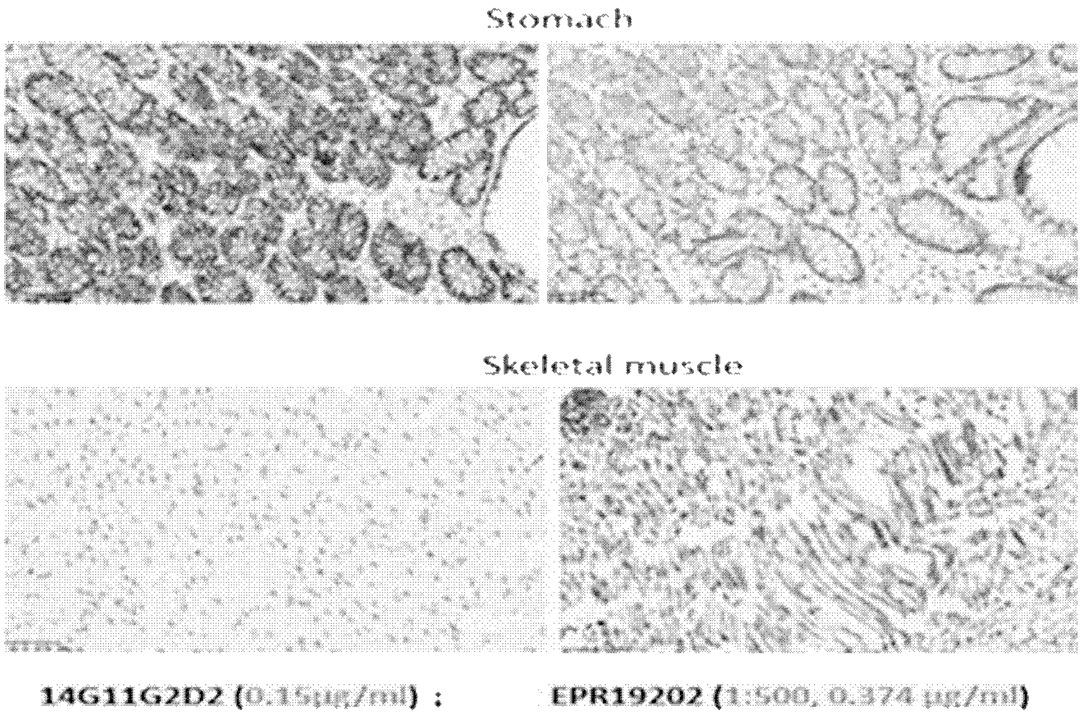
FIG. 8 shows IHC images of anti-CLDN18.2 antibodies 14G11G2D2 and EPR19202 on stomach and skeletal muscle. EPR19202 stained positive on both stomach tissue and skeletal muscle, while 14G11G2D2 only stained positive on stomach tissue.

Furthermore, the specificity and sensitivity of the selected antibodies were also compared with existing anti-CLDN18.2 antibody EPR19202 (Abcam, ab222512) on normal tissues. The IHC was performed as described above. As shown in FIG. 8, antibody EPR19202 at a concentration of 0.374 ug/ml showed weaker staining intensity on stomach tissue than the antibody 14G11G2D2 at a lower concentration, i.e. 0.15 ug/ml, indicating that ERP19202 is less sensitive than 14G11G2D2. In particular, antibody EPR19202 showed non-specific staining on skeletal muscle (FIG. 8), while antibody 14G11G2D2 maintained specificity to CLDN18.2 and did not cross-react with any of the normal tissues where CLDN18.2 was not present.

TABLE 4

Specificity Analysis on Normal Stomach, Intestine, Kidney, Skeletal muscle and Lung FFPE tissue

| Purified antibodies | Tissue | Cryo-/ Paraffin | Antibody Conc. (μg/ml) | Epithelial cells or functional tissue | Subcellular pattern | Positive cell (%) | lympho-cyte | ves-sel | fibro-cyte | smooth muscle | Comment |
|---|---|---|---|---|---|---|---|---|---|---|---|
| 69H2F7E6 | stomach | Paraffin | 0.5 | ++ | n.a. | >90 | – | – | – | – | strong membrane |
| | lung | Paraffin | 0.5 | – | n.a. | n.a. | – | – | – | – | staining on gastric |
| | Intestine | Paraffin | 0.5 | – | n.a. | n.a. | – | – | – | – | epithelium of |
| | kidney | Paraffin | 0.5 | – | n.a. | n.a. | – | – | – | – | mucosa, negative |
| | thyroid | Paraffin | 0.5 | – | n.a. | n.a. | – | – | – | – | on stroma, vessel |
| | tonsil | Paraffin | 0.5 | – | n.a. | n.a. | – | – | – | – | and muscle. |
| | breast | Paraffin | 0.5 | – | n.a. | n.a. | – | – | – | – | |
| | skeletal muscle | Paraffin | 0.5 | – | n.a. | n.a. | – | – | – | – | |

TABLE 4-continued

Specificity Analysis on Normal Stomach, Intestine, Kidney, Skeletal muscle and Lung FFPE tissue

| Purified antibodies | Tissue | Cryo-/ Paraffin | Antibody Conc. (μg/ml) | Epithelial cells or functional tissue | Subcellular pattern | Positive cell (%) | lympho-cyte | ves-sel | fibro-cyte | smooth muscle | Comment |
|---|---|---|---|---|---|---|---|---|---|---|---|
| 14G11G2D2 | stomach | Paraffin | 0.5 | ++ | n.a. | >90 | – | – | – | – | |
| | lung | Paraffin | 0.5 | – | n.a. | n.a. | – | – | – | – | |
| | Intestine | Paraffin | 0.5 | – | n.a. | n.a. | – | – | – | – | |
| | kidney | Paraffin | 0.5 | – | n.a. | n.a. | – | – | – | – | |
| | thyroid | Paraffin | 0.5 | – | n.a. | n.a. | – | – | – | – | |
| | tonsil | Paraffin | 0.5 | – | n.a. | n.a. | – | – | – | – | |
| | breast | Paraffin | 0.5 | – | n.a. | n.a. | – | – | – | – | |
| | skeletal muscle | Paraffin | 0.5 | – | n.a. | n.a. | – | – | – | – | |
| GC182 | stomach | Paraffin | 0.3 | ++ | n.a. | >90 | – | – | – | – | strong membrane staining on gastric epithelium of mucosa, and moderate membrane staining on alveolar cell of lung, negative on stroma, vessel and muscle. |
| | lung | Paraffin | 0.3 | + | n.a. | 20 | – | – | – | – | |
| | Intestine | Paraffin | 0.3 | – | n.a. | n.a. | – | – | – | – | |
| | kidney | Paraffin | 0.3 | – | n.a. | n.a. | – | – | – | – | |
| | thyroid | Paraffin | 0.3 | – | n.a. | n.a. | – | – | – | – | |
| | tonsil | Paraffin | 0.3 | – | n.a. | n.a. | – | – | – | – | |
| | breast | Paraffin | 0.3 | – | n.a. | n.a. | – | – | – | – | |
| | skeletal muscle | Paraffin | 0.3 | – | n.a. | n.a. | – | – | – | – | |

Example 9: Application of the Identified Antibodies for THC Based Evaluation of CLDN18.2 Expression Using Tumor Tissue Samples of Different Tumor Types The expression rate of CLDN18.2 in Japanese patients with gastric cancer has been reported to be detectable in 87% of tumor samples, and moderate-to-strong CLDN18.2 expression was observed in 52% of tumor samples (Rohde et al, Jpn J Clin Oncol. 2019 Sep. 1; 49(9):870-876). Furthermore, aberrant ectopic expression of CLDN18.2 has also been reported in other cancer cells including pancreatic, ovarian, biliary and lung adenocarcinomas (Sahin U et al. Clinical Cancer Research, 2008, 14(23): 7624-7634; Karanjawala Z E et al, Am J Surg Pathol. 2008 February; 32(2):188-96; Micke P et al, Int J Cancer. 2014 Nov. 1; 135(9):2206-14; Keira Y et al, Virchows Arch. 2015 March; 466(3):265-77).

Figure 9:
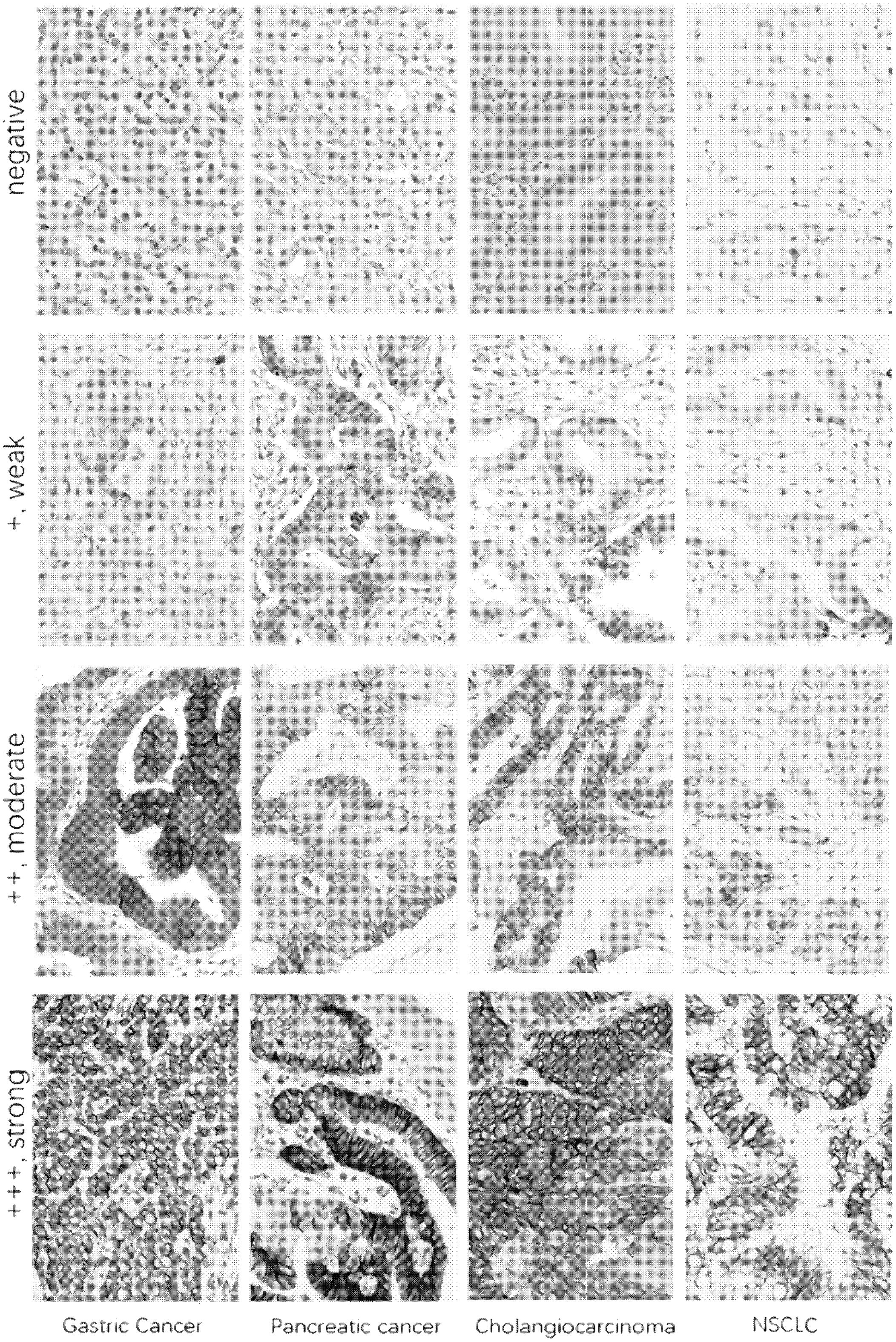
FIG. 9 shows representative IHC image of 14G11G2D2 antibodies on various tissues of gastric cancer, pancreatic cancer, cholangiocarcinoma and non-small cell lung cancer (NSCLC) with strong (+++), moderate (++), weak (+) and negative (−) staining intensity.

The 14G11G2D2 was additionally analyzed on various relevant cancer tissues to ensure the staining intensity, pattern and positivity. Immunohistochemistry (IHC) was performed on 4% neutral buffered formalin fixed paraffin embedded (FFPE) gastric, pancreatic and cholangiocarcinoma and non-small cell lung cancer (NSCLC) tumor sections. After deparaffinization and rehydration, all sections were proceeded to antigen retrieval by boiling in EnVision™ FLEX Target Retrieval Solution (Dako, K8002) for 25 minutes at 97-99° C., subsequently quenched, blocked with EnVision™ FLEX Peroxidase-Blocking Reagent (Dako, K8002) and incubated with appropriately diluted 14G11G2D2 antibodies. Antibody binding was visualized with EnVision™ FLEX+, Mouse (LINKER), followed by EnVision™ FLEX/hRP and EnVision™ FLEX Substrate Working Solution (Dako, K8002). Sections were finally counterstained with Hematoxylin and mounted with permanent mounting medium. All samples were analyzed by the relative proportion of positive stained tumor cell relative to all visible tumor cell with membrane staining of different intensity (neg (–), weak (+), moderate (++), strong (+++)). Only membrane staining was considered as positive and human normal stomach served as positive control for each staining. Weak to strong membrane signals were generated by 14G11G2D2 in gastric, pancreatic, Cholangiocarcinoma and NSCLC cancer tissues respectively (see FIG. 9) and the percentage of positive tumor cells varied inter-individually across the different tumor types (see Table 5-1 for gastric cancer, Table 5-2 for pancreatic cancer, Table 5-3 for Cholangiocarcinoma and Table 5-4 for NSCLC cancer tissues). The CLDN18.2 expression positivity and prevalence across gastric, pancreatic, cholangiocarcinoma and NSCLC cancer tissues were summarized in Table 6.

TABLE 5-1

Analysis of CLDN18.2 expression in gastric cancer tissue, using recombinant 14G11G2D2 mouse monoclonal antibody

| Tissue ID | Antibody Conc. (nM) | Cancer Type | Tumor cell (Intensity) | Positive tumor cell (TC, %) |
|---|---|---|---|---|
| 84479 | 0.6 | Gastric cancer | ++ | TC < 40% |
| 85640 | 0.6 | Gastric cancer | +++ | TC > 75% |
| 89762 | 0.6 | Gastric cancer | – | 0 |
| 91305 | 0.6 | Gastric cancer | ++ | 40% < TC < 75% |
| 91747 | 0.6 | Gastric cancer | – | 0 |
| 92679-1 | 0.6 | Gastric cancer | – | 0 |
| 93670-1 | 0.6 | Gastric cancer | – | 0 |
| 94539-1 | 0.6 | Gastric cancer | +++ | TC > 75% |
| 94997 | 0.6 | Gastric cancer | +++ | TC < 40% |
| 98306-1 | 0.6 | Gastric cancer | +++ | TC > 75% |
| 98513-1 | 0.6 | Gastric cancer | – | 0 |
| 98586-2 | 0.6 | Gastric cancer | ++ | 40% < TC < 75% |
| 98933-1 | 0.6 | Gastric cancer | ++ | 40% < TC < 75% |
| 99878-2 | 0.6 | Gastric cancer | +++ | TC > 75% |
| 99910-1 | 0.6 | Gastric cancer | + | TC < 40% |
| 103791-2 | 0.6 | Gastric cancer | – | 0 |
| 106888-1 | 0.6 | Gastric cancer | ++ | 40% < TC < 75% |
| 107334-1 | 0.6 | Gastric cancer | – | 0 |
| 107685-1 | 0.6 | Gastric cancer | +++ | 40% < TC < 75% |
| 108478-1 | 0.6 | Gastric cancer | +++ | TC > 75% |
| 108846-1 | 0.6 | Gastric cancer | – | 0 |
| 109558-1 | 0.6 | Gastric cancer | +++ | 40% < TC < 75% |
| 111276-1 | 0.6 | Gastric cancer | – | TC < 40% |
| 111888-1 | 0.6 | Gastric cancer | – | 0 |
| 112169-1 | 0.6 | Gastric cancer | +++ | 40% < TC < 75% |
| 113464-1 | 0.6 | Gastric cancer | +++ | 40% < TC < 75% |
| 113595-1 | 0.6 | Gastric cancer | +++ | 40% < TC < 75% |
| 197498-1 | 0.6 | Gastric cancer | – | 0 |
| 184874-1 | 0.6 | Gastric cancer | – | 0 |
| 192151-1 | 0.6 | Gastric cancer | – | 0 |
| 217289-4 | 0.6 | Gastric cancer | ++ | 40% < TC < 75% |
| 165965-2 | 0.6 | Gastric cancer | +++ | TC > 75% |
| 179516-1 | 0.6 | Gastric cancer | +++ | 40% < TC < 75% |

TABLE 5-1-continued

| Analysis of CLDN18.2 expression in gastric cancer tissue, using recombinant 14G11G2D2 mouse monoclonal antibody | | | | |
|---|---|---|---|---|
| Tissue ID | Antibody Conc. (nM) | Cancer Type | Tumor cell (Intensity) | Positive tumor cell (TC, %) |
| 194377-2 | 0.6 | Gastric cancer | – | 0 |
| 198778-3 | 0.6 | Gastric cancer | +++ | 40% < TC < 75% |
| 194544-5 | 0.6 | Gastric cancer | – | 0 |
| 167086-1 | 0.6 | Gastric cancer | +++ | TC > 75% |
| 183297-1 | 0.6 | Gastric cancer | +++ | 40% < TC < 75% |
| 182953-4 | 0.6 | Gastric cancer | +++ | 40% < TC < 75% |
| 197997-3 | 0.6 | Gastric cancer | – | TC < 40% |
| 208249-4 | 0.6 | Gastric cancer | +++ | 40% < TC < 75% |
| 217288-4 | 0.6 | Gastric cancer | +++ | TC > 75% |
| 196978-5 | 0.6 | Gastric cancer | – | 0 |

TABLE 5-2

| Analysis of CLDN18.2 expression in pancreatic cancer tissue, using recombinant 14G11G2D2 mouse monoclonal antibody | | | | |
|---|---|---|---|---|
| Tissue ID | Antibody Conc. (nM) | Cancer Type | Tumor cell (Intensity) | Positive tumor cell (TC, %) |
| 186421 | 0.6 | Pancreatic cancer | – | 0 |
| 100226-2 | 0.6 | Pancreatic cancer | – | 0 |
| 102838-1 | 0.6 | Pancreatic cancer | – | 0 |
| 116833-1 | 0.6 | Pancreatic cancer | +++ | 40% < TC < 75% |
| 119635-1 | 0.6 | Pancreatic cancer | +++ | TC > 75% |
| 121115-6 | 0.6 | Pancreatic cancer | +++ | TC < 40% |
| 121822-1 | 0.6 | Pancreatic cancer | +++ | TC > 75% |
| 128057-1 | 0.6 | Pancreatic cancer | ++ | TC < 40% |
| 135028-1 | 0.6 | Pancreatic cancer | ++ | TC > 75% |
| 137935-2 | 0.6 | Pancreatic cancer | ++ | TC < 40% |
| 138256-1 | 0.6 | Pancreatic cancer | – | 0 |
| 139542-6 | 0.6 | Pancreatic cancer | ++ | TC > 75% |
| 140890-1 | 0.6 | Pancreatic cancer | – | 0 |
| 148655-9 | 0.6 | Pancreatic cancer | ++ | 40% < TC < 75% |
| 148895-3 | 0.6 | Pancreatic cancer | +++ | 40% < TC < 75% |
| 149160-3 | 0.6 | Pancreatic cancer | ++ | 40% < TC < 75% |
| 152877-21 | 0.6 | Pancreatic cancer | ++ | 40% < TC < 75% |
| 153546-2 | 0.6 | Pancreatic cancer | – | 0 |
| 156769-6 | 0.6 | Pancreatic cancer | +++ | TC < 40% |
| 156944-1 | 0.6 | Pancreatic cancer | +++ | TC < 40% |
| 157295-3 | 0.6 | Pancreatic cancer | +++ | TC > 75% |
| 163041-2 | 0.6 | Pancreatic cancer | +++ | TC > 75% |
| 163580-6 | 0.6 | Pancreatic cancer | – | 0 |
| 164555-3 | 0.6 | Pancreatic cancer | ++ | 40% < TC < 75% |
| 169209-7 | 0.6 | Pancreatic cancer | +++ | TC < 40% |
| 172270-11 | 0.6 | Pancreatic cancer | – | 0 |
| 174347-8 | 0.6 | Pancreatic cancer | – | 0 |
| 174450-3 | 0.6 | Pancreatic cancer | + | TC < 40% |
| 174556-8 | 0.6 | Pancreatic cancer | ++ | TC < 40% |
| 174855-4 | 0.6 | Pancreatic cancer | – | 0 |
| 175598-1 | 0.6 | Pancreatic cancer | +++ | 40% < TC < 75% |
| 175724-3 | 0.6 | Pancreatic cancer | – | 0 |
| 175918-3 | 0.6 | Pancreatic cancer | ++ | TC < 40% |
| 178345-1 | 0.6 | Pancreatic cancer | – | 0 |
| 178465-11 | 0.6 | Pancreatic cancer | ++ | 40% < TC < 75% |
| 183055-11 | 0.6 | Pancreatic cancer | +++ | 40% < TC < 75% |
| 184292-1 | 0.6 | Pancreatic cancer | +++ | TC < 40% |
| 184599-5 | 0.6 | Pancreatic cancer | – | 0 |
| 185877-1 | 0.6 | Pancreatic cancer | – | 0 |
| 193303-3 | 0.6 | Pancreatic cancer | +++ | TC > 75% |
| 198549-1 | 0.6 | Pancreatic cancer | – | 0 |
| 198593-1 | 0.6 | Pancreatic cancer | – | 0 |
| 198658-1 | 0.6 | Pancreatic cancer | – | 0 |
| 203907-5 | 0.6 | Pancreatic cancer | ++ | 40% < TC < 75% |
| 204441-3 | 0.6 | Pancreatic cancer | – | 0 |
| 206617-3 | 0.6 | Pancreatic cancer | ++ | TC < 40% |
| 209035-7 | 0.6 | Pancreatic cancer | – | 0 |
| 209742-2 | 0.6 | Pancreatic cancer | – | 0 |
| 210876-3 | 0.6 | Pancreatic cancer | +++ | 40% < TC < 75% |
| 215116-4 | 0.6 | Pancreatic cancer | +++ | 40% < TC < 75% |

TABLE 5-2-continued

| Analysis of CLDN18.2 expression in pancreatic cancer tissue, using recombinant 14G11G2D2 mouse monoclonal antibody | | | | |
|---|---|---|---|---|
| Tissue ID | Antibody Conc. (nM) | Cancer Type | Tumor cell (Intensity) | Positive tumor cell (TC, %) |
| 217222-5 | 0.6 | Pancreatic cancer | – | 0 |
| 70137-1 | 0.6 | Pancreatic cancer | +++ | 40% < TC < 75% |
| 76512-1 | 0.6 | Pancreatic cancer | ++ | 40% < TC < 75% |
| 89616-3 | 0.6 | Pancreatic cancer | – | 0 |

TABLE 5-3

| Analysis of CLDN18.2 expression in Cholangiocarcinoma, using recombinant 14G11G2D2 mouse monoclonal antibody | | | | |
|---|---|---|---|---|
| Tissue ID | Antibody Conc. (nM) | Cancer Type | Tumor cell (Intensity) | Positive tumor cell (TC, %) |
| 215439-1 | 0.6 | Cholangiocarcinoma | +++ | TC < 40% |
| 213218-17 | 0.6 | Cholangiocarcinoma | +++ | 40% < TC < 75% |
| 199073-4 | 0.6 | Cholangiocarcinoma | – | 0 |
| 193585-4 | 0.6 | Cholangiocarcinoma | – | 0 |
| 189683-3 | 0.6 | Cholangiocarcinoma | – | 0 |
| 183293 | 0.6 | Cholangiocarcinoma | – | 0 |
| 174816-7 | 0.6 | Cholangiocarcinoma | +++ | 40% < TC < 75% |
| 176292-5 | 0.6 | Cholangiocarcinoma | ++ | 40% < TC < 75% |
| 219814-9 | 0.6 | Cholangiocarcinoma | +++ | 40% < TC < 75% |
| 217989-4 | 0.6 | Cholangiocarcinoma | ++ | TC < 40% |
| 217894-4 | 0.6 | Cholangiocarcinoma | – | 0 |
| 217524-4 | 0.6 | Cholangiocarcinoma | – | 0 |
| 214244-3 | 0.6 | Cholangiocarcinoma | ++ | TC < 40% |
| 213757-6 | 0.6 | Cholangiocarcinoma | +++ | TC < 40% |
| 213031-2 | 0.6 | Cholangiocarcinoma | +++ | TC > 75% |
| 208625 | 0.6 | Cholangiocarcinoma | +++ | TC > 75% |
| 207997-3 | 0.6 | Cholangiocarcinoma | +++ | TC > 75% |
| 205238-3 | 0.6 | Cholangiocarcinoma | – | 0 |
| 204281-3 | 0.6 | Cholangiocarcinoma | +++ | TC > 75% |
| 201886-10 | 0.6 | Cholangiocarcinoma | ++ | 40% < TC < 75% |
| 201713-9 | 0.6 | Cholangiocarcinoma | +++ | TC > 75% |
| 192881 | 0.6 | Cholangiocarcinoma | – | 0 |
| 192760 | 0.6 | Cholangiocarcinoma | +++ | TC < 40% |
| 192486-3 | 0.6 | Cholangiocarcinoma | ++ | TC < 40% |
| 191531-1 | 0.6 | Cholangiocarcinoma | – | 0 |
| 190564-7 | 0.6 | Cholangiocarcinoma | – | 0 |
| 185312-3 | 0.6 | Cholangiocarcinoma | +++ | TC < 40% |
| 184777-4 | 0.6 | Cholangiocarcinoma | ++ | TC < 40% |
| 184460-5 | 0.6 | Cholangiocarcinoma | – | 0 |
| 181163-8 | 0.6 | Cholangiocarcinoma | – | 0 |
| 181314-4 | 0.6 | Cholangiocarcinoma | – | 0 |
| 178854-5 | 0.6 | Cholangiocarcinoma | +++ | TC > 75% |
| 178534-2 | 0.6 | Cholangiocarcinoma | ++ | TC > 75% |
| 168567 | 0.6 | Cholangiocarcinoma | +++ | 40% < TC < 75% |
| 161794-1 | 0.6 | Cholangiocarcinoma | ++ | TC > 75% |
| 140645-1 | 0.6 | Cholangiocarcinoma | – | 0 |
| 140764-5 | 0.6 | Cholangiocarcinoma | – | 0 |
| 142653-5 | 0.6 | Cholangiocarcinoma | – | 0 |
| 144958-9 | 0.6 | Cholangiocarcinoma | – | 0 |
| 145513-1 | 0.6 | Cholangiocarcinoma | +++ | 40% < TC < 75% |
| 131322-1 | 0.6 | Cholangiocarcinoma | ++ | 40% < TC < 75% |
| 134376 | 0.6 | Cholangiocarcinoma | + | TC < 40% |
| 119557-1 | 0.6 | Cholangiocarcinoma | ++ | TC < 40% |
| 121438-2 | 0.6 | Cholangiocarcinoma | +++ | TC > 75% |
| 120799-2 | 0.6 | Cholangiocarcinoma | – | 0 |
| 121644-1 | 0.6 | Cholangiocarcinoma | +++ | TC < 40% |

TABLE 5-4

| Analysis of CLDN18.2 expression in NSCLC cancerous tissue, using recombinant 14G11G2D2 mouse monoclonal antibody | | | | |
|---|---|---|---|---|
| Tissue ID | Antibody Conc.(nM) | Cancer Type | Tumor cell (Intensity) | Positive tumor cell (TC, %) |
| D2142R | 0.2 | NSCLC | − | 0 |
| D2143R | 0.2 | NSCLC | − | 0 |
| D2144R | 0.2 | NSCLC | − | 0 |
| D2145R | 0.2 | NSCLC | − | 0 |
| D2147R | 0.2 | NSCLC | − | 0 |
| D2148R | 0.2 | NSCLC | − | 0 |
| D2149R | 0.2 | NSCLC | − | 0 |
| D2150R | 0.2 | NSCLC | − | 0 |
| D2151R | 0.2 | NSCLC | − | 0 |
| D2152R | 0.2 | NSCLC | − | 0 |
| D2153R | 0.2 | NSCLC | − | TC < 40% |
| D2154R | 0.2 | NSCLC | − | 0 |
| D2155R | 0.2 | NSCLC | − | 0 |
| D2156R | 0.2 | NSCLC | − | 0 |
| D2157R | 0.2 | NSCLC | − | 0 |
| D2158R | 0.2 | NSCLC | − | 0 |
| D2159R | 0.2 | NSCLC | − | 0 |
| D2160R | 0.2 | NSCLC | − | 0 |
| D2161R | 0.2 | NSCLC | − | 0 |
| D2162R | 0.2 | NSCLC | − | 0 |
| D2163R | 0.2 | NSCLC | − | 0 |
| D2164R | 0.2 | NSCLC | − | 0 |
| D2165R | 0.2 | NSCLC | − | 0 |
| D2166R | 0.2 | NSCLC | − | 0 |
| D2167R | 0.2 | NSCLC | − | 0 |

TABLE 5-4-continued

| Analysis of CLDN18.2 expression in NSCLC cancerous tissue, using recombinant 14G11G2D2 mouse monoclonal antibody | | | | |
|---|---|---|---|---|
| Tissue ID | Antibody Conc.(nM) | Cancer Type | Tumor cell (Intensity) | Positive tumor cell (TC, %) |
| D2168R | 0.2 | NSCLC | − | 0 |
| D2169R | 0.2 | NSCLC | − | 0 |
| D2170R | 0.2 | NSCLC | − | 0 |
| D2171R | 0.2 | NSCLC | − | 0 |
| D2172R | 0.2 | NSCLC | ++ | TC < 40% |
| D2173R | 0.2 | NSCLC | − | 0 |
| D2174R | 0.2 | NSCLC | +++ | TC > 75% |
| D2175R | 0.2 | NSCLC | − | 0 |
| D2177R | 0.2 | NSCLC | − | 0 |
| D2178R | 0.2 | NSCLC | − | 0 |
| D2179R | 0.2 | NSCLC | − | 0 |
| D2180R | 0.2 | NSCLC | − | 0 |
| D2181R | 0.2 | NSCLC | − | 0 |
| D2182R | 0.2 | NSCLC | − | 0 |
| D2183R | 0.2 | NSCLC | − | 0 |
| D2184R | 0.2 | NSCLC | − | 0 |
| D2185R | 0.2 | NSCLC | − | 0 |
| D2186R | 0.2 | NSCLC | − | 0 |
| D2187R | 0.2 | NSCLC | − | 0 |
| D2188R | 0.2 | NSCLC | ++ | TC < 40% |
| D2189R | 0.2 | NSCLC | − | 0 |
| D2190R | 0.2 | NSCLC | − | 0 |
| D2191R | 0.2 | NSCLC | +++ | TC > 75% |
| D2192R | 0.2 | NSCLC | − | 0 |

TABLE 6

| Positivity and Prevalence analysis of CLDN18.2 expression in different cancer types | | | | | |
|---|---|---|---|---|---|
| | Total | Negative | Positive (%) in >2+ intensity | | |
| Tumor Type | Case | (<1+ or TC < 1%) | 1% ≤ TC < 40% | 40% ≤ TC < 75% | TC ≥ 75% |
| Gastric cancer | 43 | 15(34.88%) | 5(11.63%) | 15(34.88%) | 8(18.60%) |
| Pancreatic cancer | 54 | 23(42.59%) | 11(20.37%) | 14(25.93%) | 7(12.96%) |
| Cholangiocarcinoma | 46 | 18(39.13%) | 11(23.91%) | 8(17.39%) | 9(19.57%) |
| NSCLC | 50 | 45(90.00%) | 3(6.00%) | 0(0.00%) | 2(4.00%) |

Example 10: CLDN18.2 IHC Staining Validation on Stomach Using Biotinylated 14G11G2D2

Biotinylated 14G11G2D2 (14G11G2D2-Biotin) was prepared. Briefly, Biotinamidocaproate NHS ester (Sigma, B2643-10 MG) was prepared in anhydrous DMF at 20 mg/mL as stock solution. 10 μl stock solution was added for each 1 mg 14G11G2D2 antibody to be labelled and mix gently for 1 hr at room temperature. Reaction products of low molecular weight were removed by desalting the product on Zeba™ Spin Desalting Columns (ThermoFisher, 89890) according to the manufacturer's instruction.

Immunohistochemistry (IHC) was performed on slides of 4% neutral buffered formalin fixed paraffin embedded stomach samples. After deparaffinization and rehydration, all slides were proceeded to antigen retrieval by boiling in EnVision™ FLEX Target Retrieval Solution (Dako, K8002) for 25 minutes at 97-99° C., subsequently quenched, blocked with IHC Biotin Block Kit (Mai Xin, BLK-0001) following instruction and incubated with 3 μg/mL in-house biotinylated monoclonal mouse anti-claudin 18.2 (14G11G2D2-Biotin) antibody for 30 min at 37° C. Antibody binding was visualized with horseradish peroxidase labeled streptavidin (MaiXin, SP KIT-D1) and En Vision™ FLEX Substrate Working Solution (Dako, K8002). Sections were finally counterstained with Hematoxylin and mounted with permanent mounting medium.

Figure 10:
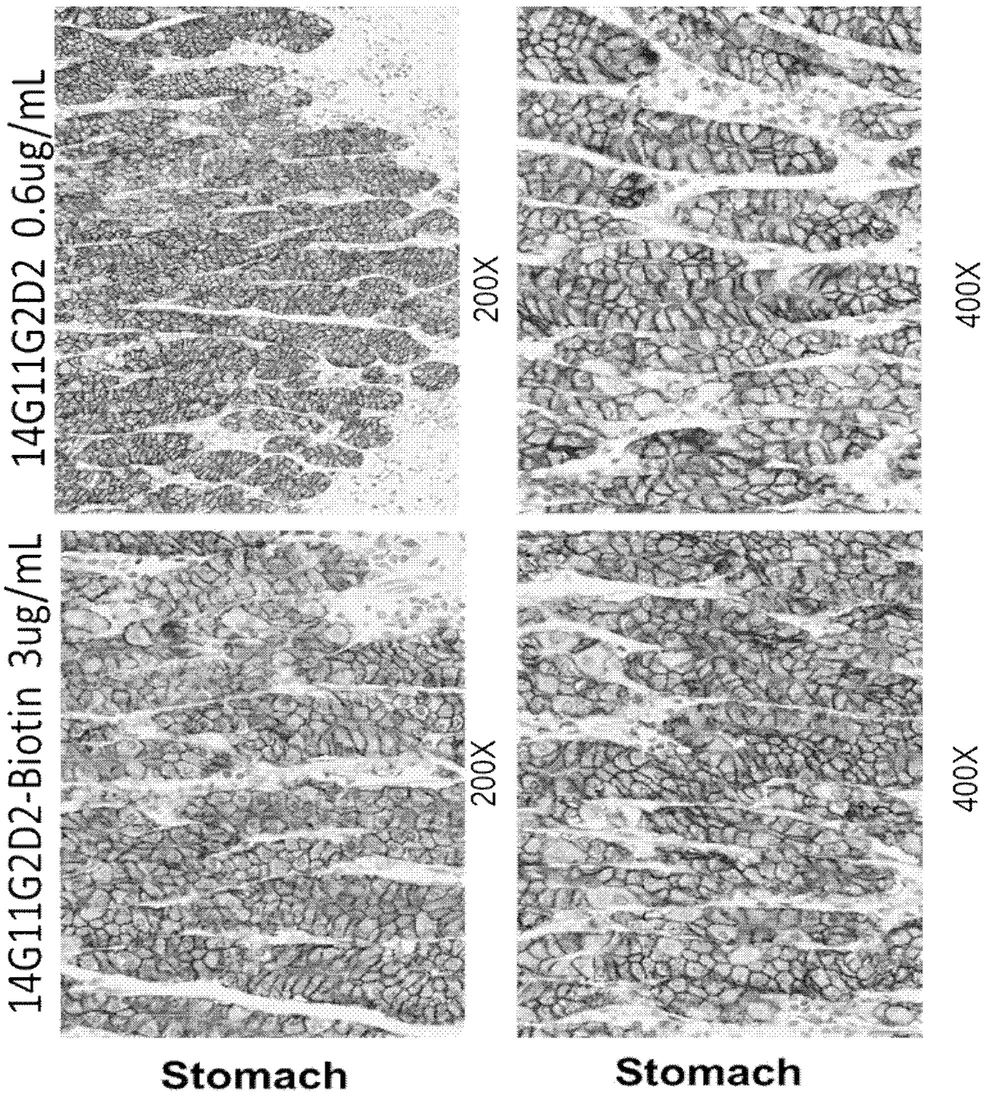
FIG. 10 shows IHC staining comparison between antibody 14G11G2D2- and antibody conjugate 14G11G2D2-biotin on stomach sections.

As shown in FIG. 10, 14G11G2D2-Biotin exhibited identical staining pattern with 14G11G2D2 with respect to intensity and specificity.

What is claimed is:

1. An isolated antibody or an antigen binding fragment thereof that specifically bind to CLDN18.2, comprising:

a) a heavy chain CDR1 comprising the amino acid sequence of $X_1X_2YX_3H$ (SEQ ID NO: 8), a heavy chain CDR2 comprising the amino acid sequence of $WIYPX_4GX_5X_6X_7X_8YX_9EKFKG$ (SEQ ID NO: 12), and a heavy chain CDR3 comprising the amino acid sequence of $NYX_{10}STFGY$ (SEQ ID NO: 24); and b) a light chain CDR1 comprising the amino acid sequence of RSSQNIVHSNGNTYLE (SEQ ID NO: 2), a light chain CDR2 comprising the amino acid sequence of $KX_{11}SNRFS$ (SEQ ID NO: 25), and a light chain CDR3 comprising the amino acid sequence of FQGSHVPFT (SEQ ID NO: 6);

wherein $X_1$ is R or T, $X_2$ is N or Y, $X_3$ is F or I, $X_4$ is G or R, $X_5$ is F or G, $X_6$ is D or N, $X_7$ is I or T, $X_8$ is E or V, $X_9$ is S or N, $X_{10}$ is G or R, and $X_{11}$ is V or I, and wherein the antibody or antigen binding fragment thereof comprises:

a) a heavy chain CDR1 comprising the amino acid sequence of SEQ ID NO: 1, a heavy chain CDR2 comprising the amino acid sequence of SEQ ID NO: 3, a heavy chain CDR3 comprising the amino acid sequence of SEQ ID NO: 5, a light chain CDR1 comprising the amino acid sequence of SEQ ID NO: 2, a light chain CDR2 comprising the amino acid sequence of SEQ ID NO: 4, and a light chain CDR3 comprising the amino acid sequence of SEQ ID NO: 6; or b) a heavy chain CDR1 comprising the amino acid sequence of SEQ ID NO: 7, a heavy chain CDR2 comprising the amino acid sequence of SEQ ID NO: 9, a heavy chain CDR3 comprising the amino acid sequence of SEQ ID NO: 11, a light chain CDR1 comprising the amino acid sequence of SEQ ID NO: 2, a light chain CDR2 comprising the amino acid sequence of SEQ ID NO: 10, and a light chain CDR3 comprising the amino acid sequence of SEQ ID NO: 6.

2. The antibody or an antigen binding fragment thereof of claim 1, comprising:

a) a heavy chain variable region comprising the amino acid sequence of SEQ ID NO: 13, and a light chain variable region comprising the amino acid sequence of SEQ ID NO: 14; or b) a heavy chain variable region comprising the amino acid sequence of SEQ ID NO: 15, and a light chain variable region comprising the amino acid sequence of SEQ ID NO: 16.

3. The antibody or antigen-binding fragment thereof of claim 1, further comprising an immunoglobulin constant region, and wherein the antibody or antigen-binding fragment thereof comprises a heavy chain constant region of IgG, and/or a light chain constant region.

4. The antibody or antigen-binding fragment thereof of claim 3, wherein the heavy chain constant region comprises an amino acid sequence of SEQ ID NO: 17 or a sequence having at least 80% sequence identity thereof, and/or the light chain constant region comprises an amino acid sequence of SEQ ID NO: 18 or a sequence having at least 80% sequence identity thereof.

5. The antibody or an antigen-binding fragment thereof of claim 1, which is a monoclonal antibody, a bispecific antibody, a multi-specific antibody, a recombinant antibody, a chimeric antibody, a humanized antibody, a labeled antibody, a bivalent antibody, an anti-idiotypic antibody, a fusion protein, a dimerized or polymerized antibody, or a modified antibody, or which is a diabody, a Fab, a Fab', a $F(ab')_2$, a Fd, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), or an scFv dimer (bivalent diabody).

6. The antibody or antigen-binding fragment thereof of claim 1, which is linked to one or more moieties, wherein the moiety comprises a radioactive isotope, a lanthanide, a chemluminescent label, a chromophoric moiety, colloidal gold particles, a fluorescent label, an enzyme-substrate label, a digoxigenin label, biotin/avidin, a hapten, a DNA molecule for detection or particle labels.

7. A method for diagnosing a CLDN18.2-associated disease or condition in a subject, comprising:

a) contacting a sample obtained from the subject with the antibody or antigen-binding fragment thereof of claim 1 under conditions that allow specific binding of the antibody or antigen-binding fragment thereof to CLDN18.2; and b) determining presence or expression level of CLDN18.2 in the sample;

wherein the subject is diagnosed as having a CLDN18.2-associated disease or condition when the presence of CLDNI 8.2 is found or when the expression level of CLDN18.2 reaches a threshold level.

8. A method for determining the eligibility of a subject having or at risk of a CLDN18.2-associated disease or condition for treatment with a CLDN18.2-targeting agent, comprising:

a) contacting a sample obtained from the subject with the antibody or antigen-binding fragment thereof of claim 2 under conditions that allow specific binding of the antibody or antigen-binding fragment thereof to CLDN18.2;

b) determining presence or expression level of CLDN18.2 in the sample;

wherein the subject is determined as eligible for treatment with a CLDN18.2-targeting agent when the presence of CLDN18.2 is found or when the expression level of CLDN18.2 reaches a threshold level, or wherein the subject is determined as not eligible for treatment with a CLDN18.2-targeting agent when the presence of CLDN18.2 is not found or when the expression level of CLDN18.2 is below a threshold level.

9. A method of predicting therapeutic effectiveness of a CLDN18.2-targeting agent in treating a CLDN18.2-associated disease or condition in a subject, comprising:

a) contacting a sample obtained from the subject with the antibody or antigen-binding fragment thereof of claim 2 under condition that allow specific binding of the antibody or antigen-binding fragment thereof to CLDN18.2;

b) determining presence or expression level of human CLDN18.2 in the sample;

c) predicting the therapeutic effectiveness of the CLDN18.2-targeting agent, wherein the CLDN18.2-targeting agent is predicted to be effective in treating the subject when the presence of CLDN18.2 is found or when the expression level of CLDN18.2 reaches a threshold level, or wherein the CLDN18.2-targeting agent is predicted to be not effective in treating the subject when the presence of CLDN18.2 is not found or when the expression level of CLDN18.2 is below the threshold level.

10. A method of treating a subject having or at risk of a CLDN18.2-associated disease or condition, comprising:

a) selecting a subject that is suitable for the treatment, comprising:

i) contacting a sample obtained from the subject with the antibody or antigen-binding fragment thereof of claim 1 under conditions that allow specific binding of the antibody or antigen-binding fragment thereof to CLDN18.2;

ii) determining the presence or expression level of human CLDN18.2 in the sample;

iii) selecting the subject as suitable for the treatment of the CLDN18.2-associated disease or condition when the presence of CLDNI 8.2 is found or when the expression level of CLDN18.2 in the sample reaches a threshold level;

b) administering a therapeutically effective amount of CLDNI 8.2-targeting agent to the selected subject.

11. A method of treating a subject having or at risk of cancer, comprising:

a) selecting a subject that is suitable for the treatment, comprising:

i) contacting a sample obtained from the subject with the antibody or antigen-binding fragment thereof of claim 1 under conditions that allow specific binding of the antibody or antigen-binding fragment thereof to CLDN18.2;

ii) determining the presence or expression level of human CLDN18.2 in the sample;

iii) selecting the subject as not suitable for the treatment with a CLDN18.2-targeting agent when the presence of CLDN18.2 is not found or when the expression level of CLDN18.2 in the sample is below a threshold level;

b) administering to the selected subject a Standard-of-Care Therapeutic other than a CLDN18.2-targeting agent.

12. The method of claim 7, wherein the sample is a cell sample or a tissue sample.

13. The method of claim 7, wherein the CLDN18.2 is cell surface or membrane-bound CLDN18.2, and wherein the presence or expression level of CLDN18.2 is determined by immunohistochemistry (IHC), Immunocytochemistry (ICC), immunofluorescence (IF), enzyme immunoassay (EIA), Enzyme-Linked Immunosorbant Assay (ELISA), or immunoblotting, and wherein the expression level is quantified based on percentage of positively-stained cells in the sample or staining intensity for CLDN18.2 in the sample.

14. The method of claim 7, wherein the CLDN18.2-associated disease or condition is cancer.

15. The method of claim 14, wherein the cancer is primary cancer or metastatic cancer.

16. The method of claim 14, wherein the cancer is gastric cancer, lung cancer, bronchial cancer, bone cancer, liver and bile duct cancer, pancreatic cancer, breast cancer, liver cancer, ovarian cancer, testicle cancer, kidney cancer, bladder cancer, head and neck cancer, spine cancer, brain cancer, cervix cancer, uterine cancer, endometrial cancer, colon cancer, colorectal cancer, rectal cancer, anal cancer, esophageal cancer, gastrointestinal cancer, skin cancer, prostate cancer, pituitary cancer, stomach cancer, vagina cancer, thyroid cancer, glioblastoma, astrocytoma, melanoma, myelodysplastic syndrome, sarcoma, teratoma, cholangiocarcinoma, and/or adenocarcinoma.

17. The method of claim 8, wherein the CLDN18.2-targeting agent is capable of inducing cytotoxicity to CLDN18.2-expressing cells, and wherein the CLDN18.2-targeting agent is a therapeutic anti-CLDN18.2 antibody or an CLDN18.2-binding molecule, a CLDN18.2-targeting cell therapy, a chemical compound targeting CLDN18.2, or a therapeutic nucleic acid targeting CLDN18.2.

18. The method of claim 7, wherein the subject is receiving or has received anti-cancer-therapy, or suffers from cancer recurrence.

19. A kit comprising the isolated antibody or antigen-binding fragment thereof of claim 1.

20. The kit of claim 19, further comprising a set of reagents for detecting a complex of the antibody or antigen-binding fragment thereof bound to CLDN18.2, and wherein the set of reagents comprises a secondary antibody that binds to the antibody or antigen-binding fragment thereof, optionally the secondary antibody is detectably labeled.

21. The kit of claim 19, wherein the antibody or the antigen binding fragment thereof is detectably labeled, or the antibody or the antigen binding fragment thereof is conjugated with an indirectly detectable moiety.

* * * * *

SEQUENCE LISTING

```
<160> NUMBER OF SEQ ID NOS: 27

<210> SEQ ID NO 1
<211> LENGTH: 5
<212> TYPE: PRT
<213> ORGANISM: Mus musculus

<400> SEQUENCE: 1

Arg Asn Tyr Phe His
1               5


<210> SEQ ID NO 2
<211> LENGTH: 16
<212> TYPE: PRT
<213> ORGANISM: Mus musculus

<400> SEQUENCE: 2

Arg Ser Ser Gln Asn Ile Val His Ser Asn Gly Asn Thr Tyr Leu Glu
1               5                   10                  15


<210> SEQ ID NO 3
<211> LENGTH: 17
<212> TYPE: PRT
<213> ORGANISM: Mus musculus

<400> SEQUENCE: 3

Trp Ile Tyr Pro Gly Gly Phe Asp Ile Glu Tyr Ser Glu Lys Phe Lys
1               5                   10                  15

Gly


<210> SEQ ID NO 4
<211> LENGTH: 7
<212> TYPE: PRT
<213> ORGANISM: Mus musculus

<400> SEQUENCE: 4

Lys Val Ser Asn Arg Phe Ser
1               5


<210> SEQ ID NO 5
<211> LENGTH: 8
<212> TYPE: PRT
<213> ORGANISM: Mus musculus

<400> SEQUENCE: 5

Asn Tyr Gly Ser Thr Phe Gly Tyr
1               5
```

<210> SEQ ID NO 6
<211> LENGTH: 9
<212> TYPE: PRT
<213> ORGANISM: Mus musculus

<400> SEQUENCE: 6

Phe Gln Gly Ser His Val Pro Phe Thr
1 5

<210> SEQ ID NO 7
<211> LENGTH: 5
<212> TYPE: PRT
<213> ORGANISM: Mus musculus

<400> SEQUENCE: 7

Thr Tyr Tyr Ile His
1 5

<210> SEQ ID NO 8
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa at location 1 can be Arg or Thr, Xaa at location 2 can be Asn or Tyr.
<220> FEATURE:
<221> NAME/KEY: misc_feature
<222> LOCATION: (4)..(4)
<223> OTHER INFORMATION: Xaa at location 4 can be Phe or Ile.

<400> SEQUENCE: 8

Xaa Xaa Tyr Xaa His
1 5

<210> SEQ ID NO 9
<211> LENGTH: 17
<212> TYPE: PRT
<213> ORGANISM: Mus musculus

<400> SEQUENCE: 9

Trp Ile Tyr Pro Arg Gly Gly Asn Thr Val Tyr Asn Glu Lys Phe Lys
1 5 10 15

Gly

<210> SEQ ID NO 10
<211> LENGTH: 7
<212> TYPE: PRT
<213> ORGANISM: Mus musculus

<400> SEQUENCE: 10

Lys Ile Ser Asn Arg Phe Ser
1 5

<210> SEQ ID NO 11
<211> LENGTH: 8
<212> TYPE: PRT
<213> ORGANISM: Mus musculus

<400> SEQUENCE: 11

Asn Tyr Arg Ser Thr Phe Gly Tyr
1 5

<210> SEQ ID NO 12
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa at location 5 can be Gly or Arg.
<220> FEATURE:
<221> NAME/KEY: misc_feature
<222> LOCATION: (7)..(10)
<223> OTHER INFORMATION: Xaa at location 7 can be Phe or Gly, Xaa at location 8 can be Asp or Asn, Xaa at location 9 can be Ile or Thr, Xaa at location 10 can be Glu or Val.
<220> FEATURE:
<221> NAME/KEY: misc_feature
<222> LOCATION: (12)..(12)
<223> OTHER INFORMATION: Xaa at location 12 can be Ser or Asn.

<400> SEQUENCE: 12

```
Trp Ile Tyr Pro Xaa Gly Xaa Xaa Xaa Xaa Tyr Xaa Glu Lys Phe Lys
1               5                   10                  15

Gly
```

<210> SEQ ID NO 13
<211> LENGTH: 117
<212> TYPE: PRT
<213> ORGANISM: Mus musculus

<400> SEQUENCE: 13

```
Gln Val Gln Leu Gln Gln Ser Gly Pro Glu Leu Val Arg Pro Gly Ala
1               5                   10                  15

Ser Val Lys Ile Ser Cys Lys Ala Ser Gly Tyr Arg Phe Thr Arg Asn
            20                  25                  30

Tyr Phe His Trp Val Lys Gln Arg Pro Gly Gln Gly Leu Glu Trp Ile
        35                  40                  45

Gly Trp Ile Tyr Pro Gly Gly Phe Asp Ile Glu Tyr Ser Glu Lys Phe
    50                  55                  60

Lys Gly Lys Ala Thr Leu Thr Thr Asp Thr Ser Ser Ser Thr Ala Tyr
65                  70                  75                  80

Met Leu Leu Thr Ser Leu Thr Ser Glu Asp Ser Ala Val Tyr Tyr Cys
                85                  90                  95

Ala Ile Asn Tyr Gly Ser Thr Phe Gly Tyr Trp Gly Gln Gly Thr Leu
            100                 105                 110

Val Thr Val Ser Val
        115
```

<210> SEQ ID NO 14
<211> LENGTH: 112
<212> TYPE: PRT
<213> ORGANISM: Mus musculus

<400> SEQUENCE: 14

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
```

```
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110


<210> SEQ ID NO 15
<211> LENGTH: 117
<212> TYPE: PRT
<213> ORGANISM: Mus musculus

<400> SEQUENCE: 15

Gln Val Gln Leu Gln Gln Ser Gly Pro Glu Leu Met Lys Pro Gly Ala
1               5                   10                  15

Ser Leu Gln Ile Ser Cys Lys Ala Ser Gly Tyr Phe Phe Thr Thr Tyr
            20                  25                  30

Tyr Ile His Trp Val Lys Gln Arg Pro Gly Gln Gly Leu Glu Trp Ile
        35                  40                  45

Gly Trp Ile Tyr Pro Arg Gly Gly Asn Thr Val Tyr Asn Glu Lys Phe
    50                  55                  60

Lys Gly Lys Ala Thr Leu Thr Ser Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Asn Tyr Arg Ser Thr Phe Gly Tyr Trp Gly Gln Gly Thr Leu
            100                 105                 110

Val Thr Val Ser Ala
        115


<210> SEQ ID NO 16
<211> LENGTH: 112
<212> TYPE: PRT
<213> ORGANISM: Mus musculus

<400> SEQUENCE: 16

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110


<210> SEQ ID NO 17
<211> LENGTH: 324
<212> TYPE: PRT
<213> ORGANISM: Mus musculus

<400> SEQUENCE: 17
```

Ala Lys Thr Thr Pro Pro Ser Val Tyr Pro Leu Ala Pro Gly Ser Ala
1 5 10 15

Ala Gln Thr Asn Ser Met Val Thr Leu Gly Cys Leu Val Lys Gly Tyr
20 25 30

Phe Pro Glu Pro Val Thr Val Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Pro Ser Ser Thr Trp Pro Ser Gln Thr Val
65 70 75 80

Thr Cys Asn Val Ala His Pro Ala Ser Ser Thr Lys Val Asp Lys Lys
85 90 95

Ile Val Pro Arg Asp Cys Gly Cys Lys Pro Cys Ile Cys Thr Val Pro
100 105 110

Glu Val Ser Ser Val Phe Ile Phe Pro Pro Lys Pro Lys Asp Val Leu
115 120 125

Thr Ile Thr Leu Thr Pro Lys Val Thr Cys Val Val Val Asp Ile Ser
130 135 140

Lys Asp Asp Pro Glu Val Gln Phe Ser Trp Phe Val Asp Asp Val Glu
145 150 155 160

Val His Thr Ala Gln Thr Lys Pro Arg Glu Glu Gln Ile Asn Ser Thr
165 170 175

Phe Arg Ser Val Ser Glu Leu Pro Ile Met His Gln Asp Trp Leu Asn
180 185 190

Gly Lys Glu Phe Lys Cys Arg Val Asn Ser Ala Ala Phe Pro Ala Pro
195 200 205

Ile Glu Lys Thr Ile Ser Lys Thr Lys Gly Arg Pro Lys Ala Pro Gln
210 215 220

Val Tyr Thr Ile Pro Pro Pro Lys Glu Gln Met Ala Lys Asp Lys Val
225 230 235 240

Ser Leu Thr Cys Met Ile Thr Asn Phe Phe Pro Glu Asp Ile Thr Val
245 250 255

Glu Trp Gln Trp Asn Gly Gln Pro Ala Glu Asn Tyr Lys Asn Thr Gln
260 265 270

Pro Ile Met Asp Thr Asp Gly Ser Tyr Phe Val Tyr Ser Lys Leu Asn
275 280 285

Val Gln Lys Ser Asn Trp Glu Ala Gly Asn Thr Phe Thr Cys Ser Val
290 295 300

Leu His Glu Gly Leu His Asn His His Thr Glu Lys Ser Leu Ser His
305 310 315 320

Ser Pro Gly Lys

<210> SEQ ID NO 18
<211> LENGTH: 107
<212> TYPE: PRT
<213> ORGANISM: Mus musculus

<400> SEQUENCE: 18

Arg Ala Asp Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 19
<211> LENGTH: 10
<212> TYPE: PRT
<213> ORGANISM: Homo sapiens

<400> SEQUENCE: 19

Asp Gln Trp Ser Thr Gln Asp Leu Tyr Asn
1               5                   10

<210> SEQ ID NO 20
<211> LENGTH: 261
<212> TYPE: PRT
<213> ORGANISM: Homo sapiens

<400> SEQUENCE: 20

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
260

<210> SEQ ID NO 21
<211> LENGTH: 261
<212> TYPE: PRT
<213> ORGANISM: Homo sapiens

<400> SEQUENCE: 21

Met Ser Thr Thr Thr Cys Gln Val Val Ala Phe Leu Leu Ser Ile Leu
1 5 10 15

Gly Leu Ala Gly Cys Ile Ala Ala Thr Gly Met Asp Met Trp Ser Thr
20 25 30

Gln Asp Leu Tyr Asp Asn Pro Val Thr Ser Val Phe Gln Tyr Glu Gly
35 40 45

Leu Trp Arg Ser Cys Val Arg Gln Ser Ser Gly Phe Thr Glu Cys Arg
50 55 60

Pro Tyr Phe Thr Ile Leu Gly Leu Pro Ala Met Leu Gln Ala Val Arg
65 70 75 80

Ala Leu Met Ile Val Gly Ile Val Leu Gly Ala Ile Gly Leu Leu Val
85 90 95

Ser Ile Phe Ala Leu Lys Cys Ile Arg Ile Gly Ser Met Glu Asp Ser
100 105 110

Ala Lys Ala Asn Met Thr Leu Thr Ser Gly Ile Met Phe Ile Val Ser
115 120 125

Gly Leu Cys Ala Ile Ala Gly Val Ser Val Phe Ala Asn Met Leu Val
130 135 140

Thr Asn Phe Trp Met Ser Thr Ala Asn Met Tyr Thr Gly Met Gly Gly
145 150 155 160

Met Val Gln Thr Val Gln Thr Arg Tyr Thr Phe Gly Ala Ala Leu Phe
165 170 175

Val Gly Trp Val Ala Gly Gly Leu Thr Leu Ile Gly Gly Val Met Met
180 185 190

Cys Ile Ala Cys Arg Gly Leu Ala Pro Glu Glu Thr Asn Tyr Lys Ala
195 200 205

Val Ser Tyr His Ala Ser Gly His Ser Val Ala Tyr Lys Pro Gly Gly
210 215 220

Phe Lys Ala Ser Thr Gly Phe Gly Ser Asn Thr Lys Asn Lys Lys Ile
225 230 235 240

Tyr Asp Gly Gly Ala Arg Thr Glu Asp Glu Val Gln Ser Tyr Pro Ser
245 250 255

Lys His Asp Tyr Val
260

<210> SEQ ID NO 22
<211> LENGTH: 115
<212> TYPE: PRT
<213> ORGANISM: Mus musculus

<400> SEQUENCE: 22

Gln Ile Gln Leu Val Gln Ser Gly Pro Glu Leu Lys Lys Phe Gly Glu
1 5 10 15

Thr Val Lys Ile Ser Cys Lys Ala Ser Gly Tyr Thr Phe Thr Asp Tyr
20 25 30

Ser Ile His Trp Val Lys Gln Ala Pro Gly Lys Gly Leu Lys Trp Met
35 40 45

Gly Trp Ile Asn Thr Glu Thr Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Thr Gly Phe Asp Tyr Trp Gly Gln Gly Thr Thr Leu Thr
            100                 105                 110

Val Ser Ser
        115

<210> SEQ ID NO 23
<211> LENGTH: 112
<212> TYPE: PRT
<213> ORGANISM: Mus musculus

<400> SEQUENCE: 23

Asp Ile Val Met Thr Gln Ala Ala Phe Ser Ile Pro Val Thr Leu Gly
1               5                   10                  15

Thr Ser Ala Ser Ile Ser Cys Arg Ser Ser Lys Asn Leu Leu His Ser
            20                  25                  30

Asp Gly Ile Thr Tyr Leu Tyr Trp Tyr Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asn Arg Phe Ser Gly Ser Glu Ser Gly Thr Asp Phe Thr Leu Arg Ile
65                  70                  75                  80

Ser Arg Val Glu Ala Glu Asp Val Gly Val Tyr Tyr Cys Val Gln Val
                85                  90                  95

Leu Glu Leu Pro Phe Thr Phe Gly Gly Gly Thr Lys Leu Glu Ile Lys
            100                 105                 110

<210> SEQ ID NO 24
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa at location 3 can be Gly or Arg.

<400> SEQUENCE: 24

Asn Tyr Xaa Ser Thr Phe Gly Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa at location 2 can be Val or Ile.

<400> SEQUENCE: 25

Lys Xaa Ser Asn Arg Phe Ser
1               5

-continued

```
<210> SEQ ID NO 26
<211> LENGTH: 58
<212> TYPE: PRT
<213> ORGANISM: Homo sapiens

<400> SEQUENCE: 26

Ala Thr Cys Met Asp Gln Trp Ser Thr Gln Asp Leu Tyr Asn Asn Pro
1               5                   10                  15

Val Thr Ala Val Phe Asn Tyr Gln Gly Leu Trp Arg Ser Cys Val Arg
            20                  25                  30

Glu Ser Ser Gly Phe Thr Glu Cys Arg Gly Tyr Phe Thr Leu Leu Gly
        35                  40                  45

Leu Pro Ala Met Leu Gln Ala Val Arg Ala
    50                  55


<210> SEQ ID NO 27
<211> LENGTH: 49
<212> TYPE: PRT
<213> ORGANISM: Homo sapiens

<400> SEQUENCE: 27

Asp Met Trp Ser Thr Gln Asp Leu Tyr Asp Asn Pro Val Thr Ser Val
1               5                   10                  15

Phe Gln Tyr Glu Gly Leu Trp Arg Ser Cys Val Arg Gln Ser Ser Gly
            20                  25                  30

Phe Thr Glu Cys Arg Pro Tyr Phe Thr Ile Leu Gly Leu Pro Ala Met
        35                  40                  45

Leu
```